US011845736B2

(12) United States Patent
Rao et al.

(10) Patent No.: US 11,845,736 B2
(45) Date of Patent: Dec. 19, 2023

(54) PRODRUGS OF MDMA, MDA, AND DERIVATIVES THEREOF

(71) Applicant: EmpathBio, Inc., Encinitas, CA (US)

(72) Inventors: Srinivas Rao, Encinitas, CA (US); Glenn Short, Scituate, MA (US); Robert B. Perni, Marlborough, MA (US); Tanweer A. Khan, Bridgewater, MA (US); Alan C. Gibbs, Wyndmoor, PA (US)

(73) Assignee: EmpathBio, Inc., Encinitas, CA (US)

( * ) Notice: Subject to any disclaimer, the term of this patent is extended or adjusted under 35 U.S.C. 154(b) by 0 days.

(21) Appl. No.: 17/959,256

(22) Filed: Oct. 3, 2022

(65) Prior Publication Data

US 2023/0227420 A1    Jul. 20, 2023

Related U.S. Application Data

(60) Provisional application No. 63/251,430, filed on Oct. 1, 2021.

(51) Int. Cl.
*C07D 317/58* (2006.01)
*C07D 411/12* (2006.01)
*C07F 9/30* (2006.01)

(52) U.S. Cl.
CPC .......... *C07D 317/58* (2013.01); *C07D 411/12* (2013.01); *C07F 9/30* (2013.01)

(58) Field of Classification Search
None
See application file for complete search history.

(56) References Cited

U.S. PATENT DOCUMENTS

| | | |
|---|---|---|
| 3,907,864 A | 9/1975 | Biel et al. |
| 4,017,636 A | 4/1977 | Jones et al. |
| 4,937,360 A | 6/1990 | Liu et al. |
| 5,061,727 A | 10/1991 | Bloom et al. |
| 5,932,749 A | 8/1999 | Li et al. |
| 9,907,812 B2 | 3/2018 | Bapat et al. |
| 2003/0171303 A1 | 9/2003 | Gallop et al. |
| 2003/0207884 A1 | 11/2003 | Haap et al. |
| 2005/0130244 A1 | 6/2005 | Zheng et al. |
| 2006/0035863 A1 | 2/2006 | Barbeau |
| 2006/0205779 A1 | 9/2006 | Mu et al. |
| 2006/0205946 A1 | 9/2006 | Ji et al. |
| 2007/0027208 A1 | 2/2007 | Caron et al. |
| 2008/0045588 A1 | 2/2008 | Gant et al. |
| 2008/0146567 A1 | 6/2008 | Kolczewski et al. |
| 2008/0293695 A1 | 11/2008 | Bristol et al. |
| 2009/0111741 A1 | 4/2009 | Aldrich et al. |
| 2010/0137428 A1 | 6/2010 | Bozzoli et al. |
| 2018/0243241 A1 | 8/2018 | Popp et al. |
| 2021/0145851 A1 | 5/2021 | Stamets |
| 2021/0332012 A1 | 10/2021 | Olson et al. |
| 2022/0151986 A1 | 5/2022 | Liechti et al. |
| 2022/0267252 A1 | 8/2022 | Trachsel et al. |
| 2022/0354822 A1 | 11/2022 | Barrow et al. |
| 2023/0096116 A1 | 3/2023 | Fawaz et al. |
| 2023/0097530 A1 | 3/2023 | Short et al. |
| 2023/0109467 A1 | 4/2023 | Anzalone et al. |
| 2023/0129723 A1 | 4/2023 | Short et al. |

FOREIGN PATENT DOCUMENTS

| | | |
|---|---|---|
| CN | 101822841 A | 9/2010 |
| EP | 2687854 A1 | 1/2014 |
| WO | WO-2005038049 A2 | 4/2005 |
| WO | WO-2007090733 A1 | 8/2007 |
| WO | WO-2008033351 A2 | 3/2008 |
| WO | WO-2009049233 A1 | 4/2009 |
| WO | WO-2009095479 A2 | 8/2009 |
| WO | WO-2012177986 A2 | 12/2012 |
| WO | WO-2014013063 A1 | 1/2014 |
| WO | WO-2017147375 A1 | 8/2017 |
| WO | WO-2020077217 A1 | 4/2020 |
| WO | WO-2020101543 A1 | 5/2020 |
| WO | WO-2020252384 A1 | 12/2020 |
| WO | WO-2021252538 A2 | 12/2021 |
| WO | WO-2022006192 A1 | 1/2022 |
| WO | WO-2022010937 A1 | 1/2022 |
| WO | WO-2022032147 A1 | 2/2022 |
| WO | WO-2022053696 A1 | 3/2022 |
| WO | WO-2022061242 A1 | 3/2022 |
| WO | WO-2022106947 A1 | 5/2022 |
| WO | WO-2022150525 A1 | 7/2022 |
| WO | WO-2022182602 A2 | 9/2022 |
| WO | WO-2022235530 A1 | 11/2022 |
| WO | WO-2022256720 A2 | 12/2022 |
| WO | WO-2023056102 A1 | 4/2023 |
| WO | WO-2023056472 A1 | 4/2023 |

OTHER PUBLICATIONS

Baker, et al., Critical evaluation of methodology commonly used in sample collection, storage and preparation for the analysis of pharmaceuticals and illicit drugs in surface water and wastewater by solid phase extraction and liquid chromatography-mass spectrometry, Journal of Chromatography A, 2011, pp. 8036-8059.

Baker, et al., Drugs of abuse in wastewater and suspended particulate matter—Further developments in sewage epidemiology, Environment International, 2012, pp. 28-38.

Baker, et al., Multi-residue analysis of drugs of abuse in wastewater and surface water by solid-phase extraction and liquid chromatography-positive electrospray ionisation tandem mass spectrometry, Journal of Chromatography A, 2011, pp. 1620-1631.

Baker, et al., Multi-residue determination of the sorption of illicit drugs and pharmaceuticals to wastewater suspended particulate matter using pressurized liquid extraction, solid phase extraction and liquid chromatography coupled with tandem mass spectrometry, Journal of Chromatography A, Nov. 2011, pp. 7901-7913.

(Continued)

*Primary Examiner* — Samantha L Shterengarts
(74) *Attorney, Agent, or Firm* — COOLEY LLP

(57) ABSTRACT

The present disclosure provides prodrug compounds of MDMA, MDA, and derivatives thereof having an improved pharmacokinetic profile suitable for the treatment of various neurological diseases.

25 Claims, No Drawings

(56) References Cited

OTHER PUBLICATIONS

Castrignano, et al., Enantiomeric profiling of chiral drug biomarkers in wastewater with the usage of chiral liquid chromatography coupled with tandem mass spectrometry, Journal of chromatography A, Mar. 2016, pp. 84-99.

Castrignano, et al., Enantiomeric profiling of chiral illicit drugs in a pan—European study, Water Research, Mar. 2017, 56 pages.

Chen, et al., Investigation of the relationship between phenol ionization and affinity of norepinephrine for adrenergic receptors using ring-fluorinated analogs, Medicinal Chemistry Research, 1994, pp. 589-597.

Chen, et al., Syntheses of 2,5- and 2,6-difluoronorepinephrine, 2,5-difluoroepinephrine, and 2,6-difluorophenylephrine: effect of disubstitution with fluorine on adrenergic activity, Journal of Medicinal Chemistry, 1993, pp. 3947-3955.

Collins, et al., Identification and characterization of N-tert-butoxycarbonyl-MDMA: a new MDMA precursor, Drug Testing and Analysis, Mar. 2017, pp. 399-404.

Corkery, et al., Deaths in the Lesbian, Gay, Bisexual and Transgender United Kingdom Communities Associated with GHB and Precursors, Current drug metabolism, Nov. 2018, pp. 1086-1099.

DeLuca, et al., Searching the Internet for drug-related web sites: analysis of online available information on ecstasy (MDMA), American Journal on Addictions, Nov. 2007, 5 pages.

Filler, et al., Fluorine-containing catecholamines. Synthesis of DL-2,5,6-trifluorodopa, Journal of Fluorine Chemistry, 1981, pp. 483-495.

Ladd, et al., Improved synthesis of fluoroveratroles and fluorophenethylamines via organolithium reagents, Journal of Organic Chemistry, 1981, pp. 203-206.

Leapman, et al., Application of parallel recorded EELS to analysis of beam-sensitive organic compounds, Biomed. Eng. Instrum., Proceedings—Annual Meeting, Electron Microscopy Society of America, 1988, pp. 632-633.

Leapman, et al., Applications of electron energy loss spectroscopy in biology: detection of calcium and fluorine, Proceedings—Annual Meeting, Electron Microscopy Society of America, 1982, pp. 412-415.

Milhazes, et al., Electrochemical and spectroscopic characterisation of amphetamine-like drugs: Application to the screening of 3,4-methylenedioxymethamphetamine (MDMA) and its synthetic precursors, Analytica Chimica Acta, 2007, pp. 231-241.

Mustafa, et al., Review Paper: MDMA and the Brain: A Short Review on the Role of Neurotransmitters in Neurotoxicity, Basic and Clinical Neuroscience, 2020, pp. 381-388.

Nie, et al., Synthesis of fluorodopamines: effect of aryl fluoro substituents on affinities for adrenergic and dopaminergic receptors, Medicinal Chemistry Research, Jan. 1996, pp. 318-332.

Pubchem, Substance Record for SID 406789554, Jul. 18, 2020, 6 pages.

Pubchem, Substance Record for SID 439624087, Jan. 15, 2021, 6 pages.

Pubchem, SID 243280603, Modify Date: Jun. 24, 2015 [retrieved on Dec. 27, 2022]., Retrieved from the Internet [URL: https://pubchem.ncbi.nlm.nih.gov/substance/243280603].

Pubchem, Substance Record for SID 38492237, Dec. 5, 2007, 5 pages.

Strajhar, et al., Effects of lisdexamfetamine on plasma steroid concentrations compared with d-amphetamine in healthy subjects: A randomized, double-blind, placebo-controlled study, The Journal of steroid biochemistry and molecular biology, Feb. 2019, pp. 212-225.

Sun, et al., Facile and universal immobilization of L-lysine inspired by mussels, J. Mater. Chem., 2012, Journal of Materials Chemistry, 2012, pp. 10035-41.

Thomsen, et al., In Vitro Drug Metabolism by Human Carboxylesterase 1: Focus on Angiotensin-Converting Enzyme Inhibitors, Drug Metabolism and Disposition, Jan. 2014, pp. 126-133.

United States Patent and Trademark Office, International Search Report and Written Opinion for International Application No. PCT/US2022/045587 dated Feb. 1, 2023, 25 pages.

United States Patent and Trademark Office, Invitation to Pay Fees for Application No. PCT/US2022/045587 dated Nov. 18, 2022, 3 pages.

Weinstock, et al., Ecstasy pill testing: harm minimization gone too far?, Addiction, 2001, pp. 1139-1148.

Weinstock, et al., Synthesis and renal vasodilator activity of some dopamine agonist 1-aryl-2,3,4,5-tetrahydro-1H-3-benzazepine-7,8-diols: halogen and methyl analogs of fenoldopam, Journal of Medicinal Chemistry, 1986, pp. 2315-2325.

Wu, et al., Estimation of tamoxifen metabolite concentrations in the blood of breast cancer patients through CYP2D6 genotype activity score, Breast Cancer Research and Treatment, 2012, pp. 677-683.

Barreiro, et al., A High-Resolution Magic Angle Spinning NMR Study of the Enantiodiscrimination of 3,4-Methylenedioxymethamphetamine (MDMA) by an Immobilized Polysaccharide-Based Chiral Phase, PLoS ONE, Sep. 2016, pp. 1-11.

Clouting, The Commercial Chemistry of MDMA: From Research to Patient Access, MAPS Bulletin Special Edition, Spring 2020, pp. 8-10.

Crean, et al., Oral Administration of (±)3,4-Methylenedioxymethamphetamine and (+) Methamphetamine Alters Temperature and Activity in Rhesus Macaques, Pharmacol Biochem Behav, Authors Manuscript PMC, May 2008, pp. 1-18.

Curry et al., Separating the agony from ecstasy: R(−)-3,4-methylenedioxymethamphetamine has prosocial and therapeutic-like effects without signs of neurotoxicity in mice, Neuropharmacology, Jan. 2018, pp. 196-206.

Dunlap et al., Dark Classics in Chemical Neuroscience: 3,4-Methylenedioxymethamphetamine (MDMA), ACS Chem Neurosci. 2018 Oct. 2018, pp. 2408-2427.

Eiden, et al., VMAT2: a dynamic regulator of brain monoaminergic neuronal function interacting with drugs of abuse, Ann N Y Acad Sci., Jan. 2011, pp. 86-98.

Fallon et al., Stereospecific analysis and enantiomeric disposition of 3, 4-methylenedioxymethamphetamine (Ecstasy) in humans, Clinical Chemistry, Jul. 1999, pp. 1058-1069.

Fantegrossi, et al., 3, 4-Methylenedioxymethamphetamine (MDMA, ecstasy) and its stereoisomers as reinforcers in rhesus monkeys: serotonergic involvement, Psychopharmacology, Jun. 2002, pp. 56-64.

Fantegrossi et al., Pharmacological characterization of the effects of 3, 4-methylenedioxymethamphetamine (ecstasy) and its enantiomers on lethality, core temperature, and locomotor activity in singly housed and crowded mice, Psychopharmacology, Mar. 2003, pp. 202-211.

Fantegrossi, In vivo pharmacology of MDMA and its enantiomers in rhesus monkeys, Experimental and clinical psychopharmacology, Feb. 2008, 1 page.

Felim et al., Synthesis and in vitro cytotoxicity profile of the R-enantiomer of 3, 4-dihydroxymethamphetamine (R-(−)-HHMA): comparison with related catecholamines, Chem. Res. Toxicol., Jan. 2010, pp. 211-219.

Fitzgerald, et al., Stereoselective pharmacokinetics of 3, 4-methylenedioxymethamphetamine in the rat, Chirality, 1990, pp. 241-248.

Forsling, et al., The effect of 3,4-methylenedioxymethamphetamine (MDMA, 'ecstasy') and its metabolites on neurohypophysial hormone release from the isolated rat hypothalamus, British Journal of Pharmacology, Feb. 2002, pp. 649-656.

Hagele, et al., Enantioselective separation of Novel Psychoactive Substances using a Lux® AMP 3 µm column and HPLC-UV. Journal of Pharmaceutical and Biomedical Analysis, Feb. 2020, 2 pages.

Han, et al., Comparison of the monoamine transporters from human and mouse in their sensitivities to psychostimulant drugs, BMC Pharmacology, Dec. 2006, pp. 1-7.

Heather, The Synthesis and Chemical Profiling of 3,4-Methylenedioxymethamphetamine (MDMA) and Analogues, Thesis, University of Technology Sydney, Oct. 2020, 232 pages.

(56) References Cited

OTHER PUBLICATIONS

Hensley, et al., Simultaneous determination of amphetamine, methamphetamine, methylenedioxyamphetamine (MDA), methylenedioxymethamphetamine (MDMA), and methylenedioxyethylamphetamine (MDEA) enantiomers by GC-MS, Journal of Analytical Toxicology, Oct. 1999, pp. 518-523.
Herr, et al., Re-evaluation of the discriminative stimulus effects of lysergic acid diethylamide with male and female Sprague-Dawley rats, Behavioral Pharmacology, Sep. 2020, pp. 776-786.
Hiramatsu, et al., Enantiomeric differences in the effects of 3, 4-methylenedioxymethamphetamine on extracellular monoamines and metabolites in the striatum of freely-moving rats: an in vivo microdialysis study, Neuropharmacology, Mar. 1990, pp. 269-275.
Huot et al., Characterization of 3,4-Methylenedioxymethamphetamine (MDMA) Enantiomers In Vitro and in the MPTP-Lesioned Primate: R-MDMA Reduces Severity of Dyskinesia, Whereas S-MDMA Extends Duration of ON-Time, The Journal of Neuroscience, May 2011, pp. 7190-7198.
International Search Report and Written Opinion for Application No. PCT/US2022/042353, dated Dec. 8, 2022, and received Dec. 13, 2022, 9 pages.
International Search Report and Written Opinion for International Application No. PCT/US2022/043833 dated Jan. 12, 2023, 13 pages.
International Search Report and Written Opinion for International Application No. PCT/US2022/082468, dated Jun. 6, 2023, 11 pages.
Invitation to Pay for International Application No. PCT/US2022/082468 dated Mar. 16, 2023, 2 pages.
Johnson et al., Effects of enantiomers of MDA, MDMA and related analogues on [3H] serotonin and [3H] dopamine release from superfused rat brain slices, European Journal of Pharmacology, 1986, pp. 269-276.
Kilpatrick, et al., National estimates of exposure to traumatic events and PTSD prevalence using DSM-IV and DSM-5 criteria, Journal of Traumatic Stress, Oct. 2013, pp. 537-547.
Kozma, et al., Optical resolution of N-methylamphetamine via diastereoisomeric salt formation with 2R, 3R-O, O'-di-p-toluoyltartaric acid, Chirality, 1999, pp. 373-375.
Levine et al. (editor), Principles of Forensic Toxicology, Springer, Fifth Edition, 2020, 680 pages.
Liabres et al., Molecular basis of the selective binding of MDMA enantiomers to the alpha4beta2 nicotinic receptor subtype: synthesis, pharmacological evaluation and mechanistic studies, European Journal of Medicinal Chemistry, Jun. 2014, pp. 35-46.
Lourenco et al., Chiral separation of 3, 4-methylenedioxymethamphetamine (MDMA) enantiomers using batch chromatography with peak shaving recycling and its effects on oxidative stress status in rat liver, Journal of Pharmaceutical and Biomedical Analysis, Jan. 2013, pp. 13-17.
Madry, et al., Evaluation of drug incorporation into hair segments and nails by enantiomeric analysis following controlled single MDMA intakes, Analytical and Bioanalytical Chemistry, Jan. 2016, pp. 545-556.
Martins, et al., Simultaneous enantioselective determination of amphetamine and congeners in hair specimens by negative chemical ionization gas chromatography—mass spectrometry, Journal of Chromatography B, Oct. 2005, pp. 57-62.
Martins, et al., Time-resolved hair analysis of MDMA enantiomers by GC/MS-NCI, Forensic Science International, Oct. 2007, pp. 150-155.
Mas, et al., Cardiovascular and neuroendocrine effects and pharmacokinetics of 3, 4-methylenedioxymethamphetamine in humans, Journal of Pharmacology and Experimental Therapeutics, Jul. 1999, pp. 136-145.
Matsushima, et al., Optical isomer analysis of 3, 4-methylenedioxyamphetamine analogues and their stereoselective disposition in rats, Journal of Analytical Toxicology, Jan. 1998, pp. 33-39.

Murnane, et al., Discriminative stimulus effects of psychostimulants and hallucinogens in S (+)-3, 4-methylenedioxymethamphetamine (MDMA) and R (−)-MDMA trained mice, Journal of Pharmacology and Experimental Therapeutics, Nov. 2009, pp. 717-723.
Murnane, et al., Endocrine and neurochemical effects of 3, 4-methylenedioxymethamphetamine and its stereoisomers in rhesus monkeys, Journal of Pharmacology and Experimental Therapeutics, Aug. 2010, pp. 642-650.
Murnane, et al., The neuropharmacology of prolactin secretion elicited by 3, 4-methylenedioxymethamphetamine (ecstasy): a concurrent microdialysis and plasma analysis study, Hormones and behavior, Feb. 2012, pp. 181-190.
Nair et al., Fully Validated, Multi-Kilogram cGMP Synthesis of MDMA, ACS Omega, Dec. 2021, pp. 900-907.
Nenajdenko et al., A new convenient approach to chiral β-aryl (heteroaryl) alkylamines, Tetrahedron: Asymmetry, Oct. 2001, pp. 2517-2527.
Nichols, et al., Derivatives of 1-(1,3-benzodioxol-5-yl)-2-butanamine: representatives of a novel therapeutic class, Journal of Medicinal Chemistry, Oct. 1986, pp. 2009-2015.
Organic Chemistry Portal Amino Protecting Groups Stability, 1999, pp. 1-3.
Peters, et al., Concentrations and ratios of amphetamine, methamphetamine, MDA, MDMA, and MDEA enantiomers determined in plasma samples from clinical toxicology and driving under the influence of drugs cases by GC-NICI-MS, Journal of Analytical Toxicology, Nov. 2003, pp. 552-559.
Peters, et al., Drug testing in blood: validated negative-ion chemical ionization gas chromatographic-mass spectrometric assay for determination of amphetamine and methamphetamine enantiomers and its application to toxicology cases, Clinical Chemistry, Sep. 2002, pp. 1472-1485.
Peters, et al., Negative-ion chemical ionization gas chromatography-mass spectrometry assay for enantioselective measurement of amphetamines in oral fluid: application to a controlled study with MDMA and driving under the influence cases, Clinical chemistry, Apr. 2007 A, pp. 702-710.
Pitts et al., (±)-MDMA and its enantiomers: potential therapeutic advantages of R(−)-MDMA, Psychopharmacology, Feb. 2018, pp. 377-392.
Pizarro, et al., Stereochemical analysis of 3, 4-methylenedioxymethamphetamine and its main metabolites in human samples including the catechol-type metabolite (3, 4-dihydroxymethamphetamine), Drug Metabolism and Disposition, Sep. 2004, pp. 1001-1007.
Pizarro et al., Synthesis and Capillary Electrophoretic Analysis of Enantiomerically Enriched Reference Standards of MDMA and its Main Metabolites, Bioorganic & Medicinal Chemistry, Apr. 2002, pp. 1085-1092.
Pubchem, SID 235735835, Feb. 13, 2015, 8 pages.
Pubchem, Substance Record for SID 104098418, Jan. 2011, 6 pages.
Pubchem, Substance Record for SID 117678335, Apr. 2011, 6 pages.
Pubill, et al., Neuronal nicotinic receptors as new targets for amphetamine-induced oxidative damage and neurotoxicity, Pharmaceuticals, Jun. 2011, pp. 822-847.
Rasmussen et al., Chiral separation and quantification of R/S-amphetamine, R/S-methamphetamine, R/S-MDA, R/S-MDMA, and R/S-MDEA in whole blood by GC-EI-MS, Journal of Chromatography B, Oct. 2006, pp. 136-141.
Rickli, et al., Pharmacological profile of novel psychoactive benzofurans, British Journal of Pharmacology, Jul. 2015, pp. 3412-3425.
Rothman, et al., Amphetamine-type central nervous system stimulants release norepinephrine more potently than they release dopamine and serotonin, Synapse, Jan. 2001, pp. 32-41.
Rudnick, et al., The molecular mechanism of ecstasy [3, 4-methylenedioxy-methamphetamine (MDMA)]: serotonin transporters are targets for MDMA-induced serotonin release, Proceedings of the National Academy of Sciences, Mar. 1992, pp. 1817-1821.
Schwaninger, et al., Development and validation of LC-HRMS and GC-NICI-MS methods for stereoselective determination of MDMA

(56) References Cited

OTHER PUBLICATIONS and its phase I and II metabolites in human urine, Journal of Mass Spectrometry, Jul. 2011, pp. 603-614.

Schwaninger, et al., Stereoselective urinary MDMA (ecstasy) and metabolites excretion kinetics following controlled MDMA administration to humans, Biochemical pharmacology, Jan. 2012, pp. 131-138.

Setola, et al., 3,4-methylenedioxymethamphetamine (MDMA, Ecstasy) induces fenfluramine-like proliferative actions on human cardiac valvular interstitial cells in vitro, Molecular Pharmacology, Jun. 2003, pp. 1223-1229.

Steele, et al., Stereochemical effects of 3,4-methylenedioxymethamphetamine (MDMA) and related amphetamine derivatives on inhibition of uptake of [3H] monoamines into synaptosomes from different regions of rat brain, Biochemical Pharmacology, Jul. 1987, pp. 2297-2303.

Thomas, et al., Characterization of 3,4-methylenedioxypyrovalerone discrimination in female Sprague-Dawley rats, Behavioural Pharmacology, Jul. 2021, pp. 524-532.

Tournier, et al., Interaction of drugs of abuse and maintenance treatments with human P-glycoprotein (ABCB1) and breast cancer resistance protein (ABCG2), International Journal of Neuropsychopharmacology, Aug. 2010, pp. 905-915.

United States Patent and Trademark Office, International Search Report and Written Opinion for International Application No. PCT/US2022/077432 dated Dec. 15, 2022, 14 pages.

Verrico, et al., MDMA (Ecstasy) and human dopamine, norepinephrine, and serotonin transporters: implications for MDMA-induced neurotoxicity and treatment, Psychopharmacology, Jan. 2007, pp. 489-503.

Verweij, Impurities in illicit drug preparations; 3,4-methylenedioxyamphetamine and 3-4-methylenedioxymethylamphetamine, Forensic. Sci. Rev., 1992, pp. 1-6.

Young, et al., MDMA (N-methyl-3,4-methylenedioxyamphetamine) and its Stereoisomers: Similarities and Differences in Behavioral Effects in an Automated Activity Apparatus in Mice, Pharmacol Biochem Behav., Jan. 2008, pp. 318-331.

PRODRUGS OF MDMA, MDA, AND DERIVATIVES THEREOF

CROSS-REFERENCE TO RELATED APPLICATION

This application claims the benefit of priority to U.S. Provisional Application No. 63/251,430, filed Oct. 1, 2021, which is hereby incorporated by reference in its entirety.

BACKGROUND OF THE INVENTION

Field of the Invention

The present invention relates novel prodrugs of MDMA, MDA and derivatives thereof, as well as to methods employing such compounds for the treatment of post-traumatic stress disorder (PTSD), eating disorders, depression (including major depressive disorders (MDD) or treatment-resistant depression (TRD)), and anxiety disorders including generalized anxiety disorder.

Description of Related Art 3,4-methylenedioxymethamphetamine (MDMA), also known as Ecstasy, is considered the prototype of a class of compounds called entactogens, which means "to touch within," their main characteristic being their ability to increase feelings of love, empathy, and closeness towards others. Structurally, MDMA is a ring-substituted phenethylamine with a chiral molecular center that gives rise to two stereoisomers: (S)(+)-MDMA and (R)(−)-MDMA. Typically, the effects of (S)-MDMA resemble those of psychostimulants and are primarily mediated by dopaminergic and noradrenergic pathways, including increases in motor activity and euphoria, whereas (R)-MDMA induces qualitative effects similar to classical psychedelics, such as ego-dissolution and perceptive alterations, mediated by serotonergic pathways, including direct 5-HT2A receptor agonism (Murnane et al., 2009). The molecular mechanisms for these differences are supported by preclinical evidence and point to a higher therapeutic index for the R-enantiomer.

To this point, harnessing the biological active of MDMA in an effective therapeutic treatment has been somewhat limited. This is due at least in part to a problematic pharmacokinetic profile related to non-proportional dose-dependency upon administration in humans. Studies have demonstrated that MDMA is metabolized to three main metabolites identified as MDA, HMMA and HMA, which are found in the plasma in different proportions, depending on the concentration of the drug administered. At doses around 50-100 mg, HMMA predominates, while at doses between 125-150 mg MDMA predominates, indicating a possible saturation of its own metabolic pathways. The main hepatic enzymes involved in MDMA metabolism, as identified from in vitro experiments in human liver microsomes, are CYP1A2, CYP2D6 and CTP3A4. Furthermore, stereochemistry appears to play a role in the non-renal pharmacokinetics of MDMA, with the S-enantiomer having a shorter half-life, lower peak plasma concentrations and increased clearance (Green et al., 2003).

For two doses of racemic MDMA and MDA, the following PK measurements were observed in healthy human subjects:

125 mg MDMA: Cmax 236.4 ng/ml; Tmax at 2.4 hours; elimination half-life 8.6 hours; $AUC_{0-24}$ 2623 $ng/ml*h^{-1}$ 125 mg MDA: Cmax 13.7 ng/ml; Tmax at 7 hours; $AUC_{0-24}$ 215 $ng/ml*h^{-1}$ 75 mg MDMA: Cmax 130.9 ng/ml; Tmax 1.8 hours; elimination half-life 7.7 hours; $AUC_{0-24}$ 1331 $ng/ml*h^{-1}$ 75 mg MDA: Cmax 7.8 ng/ml; Tmax at 5 hours; $AUC_{0-24}$ 122 $ng/ml*h^{-1}$ In reference to MDA pharmacokinetics, the MDA formation rate constant has been estimated for both MDMA doses of being about 0.75 h. Elimination half-life of MDA was in a range of 16 to 28 h (Mas, 1999).

Accordingly, novel approaches that improve the pharmacokinetics of MDMA and MDA are needed in order to take advantage of the wide ranging pharmacologic properties of these compounds in treating various diseases and conditions.

SUMMARY

MDA and MDMA prodrugs are herein disclosed that reduce $C_{max}$ while maintaining AUC over an extended period after dosing. Several methodologies have been developed. Since primary and secondary amines have intrinsically different reactivities, MDA and MDMA require different pro-moieties. As set forth in the Detailed Description, two "enacarbil" analogues were initially synthesized as well as 3-5 amino acid analogues.

To address these and other issues, in one aspect, the present disclosure provides. a compound of Formula (I):

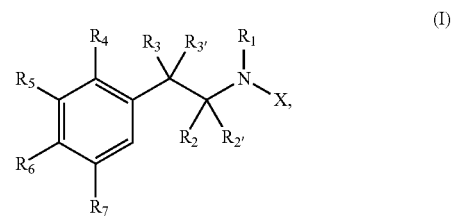

or a pharmaceutically acceptable salt thereof;
wherein,
$R_1$ is H or alkyl;
$R_2$ and $R_{2'}$ are each independently H, halogen, alkyl, —OH, or —O-alkyl, or $R_2$ and $R_{2'}$ together with the atom to which they are attached form a cycloalkyl ring;
$R_3$ and $R_{3'}$ are each independently hydrogen, alkyl, —OH, —O-alkyl, or —O-cycloalkyl, or
$R_3$ and $R_{3'}$ together with the atom to which they are attached form an oxo;
$R_4$, $R_5$, $R_6$ and $R_7$ are each independently hydrogen, halogen, —OH, —O-alkyl, —O-cycloalkyl, alkylene-$OR_8$, —SH, —S-alkyl, —S-cycloalkyl, or alkylene-$SR_8$, or $R_5$ and $R_6$ together with the atoms to which they are attached form a 5- to 8-membered heterocyclyl ring;
$R_8$ is H, alkyl, cycloalkyl, or alkylenecycloalkyl;
X is a cleavable promoiety having the structure

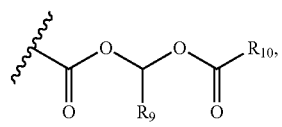

wherein:

R$_9$ and R$_{10}$ are each independently alkyl or phenyl. In some embodiments, R$_9$ and R$_{10}$ are each alkyl, e.g., C$_{1-5}$ alkyl.

In some embodiments, the compound of the present disclosure has the following structure:

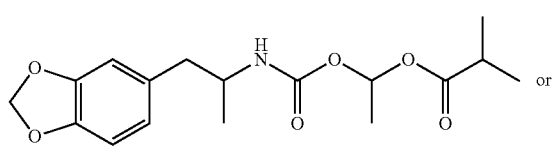

or

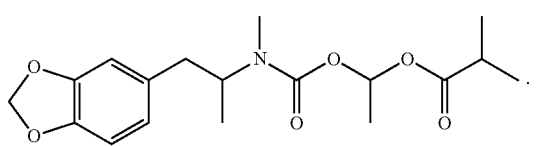

In another aspect, the present disclosure provides a compound of Formula (II):

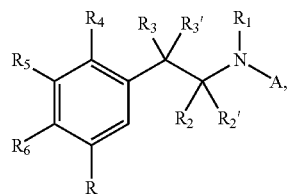

or a pharmaceutically acceptable salt thereof;
wherein,
R$_1$ is H or alkyl;
R$_2$ and R$_{2'}$ are each independently H, halogen, alkyl, —OH, or —O-alkyl, or R$_2$ and R$_{2'}$ together with the atom to which they are attached form a cycloalkyl ring;
R$_3$ and R$_{3'}$ are each independently hydrogen, alkyl, —OH, —O-alkyl, or —O-cycloalkyl, or
R$_3$ and R$_{3'}$ together with the atom to which they are attached form an oxo;
R$_4$, R$_5$, R$_6$ and R$_7$ are each independently hydrogen, halogen, —OH, —O-alkyl, —O-cycloalkyl, alkylene-OR$_8$, —SH, —S-alkyl, —S-cycloalkyl, or alkylene-SR$_8$, or R$_5$ and R$_6$ together with the atoms to which they are attached form a 5- to 8-membered heterocyclyl ring;
R$_8$ is H, alkyl, cycloalkyl, or alkylenecycloalkyl; and
A is a cleavable promoiety having the structure

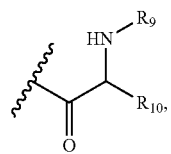

wherein:

R$_9$ is H, alkyl or acyl; and
R$_{10}$ is H, aryl, or —(CH$_2$)$_m$—R$_{11}$,
wherein m is an integer from 1-5; and
R$_{11}$ is amino, guanidino, thioalkyl, or aryl.

In some embodiments, A is:

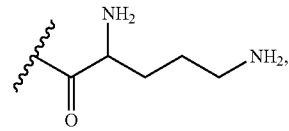

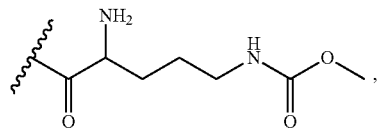

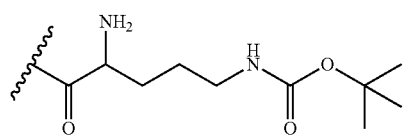

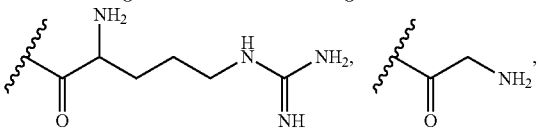

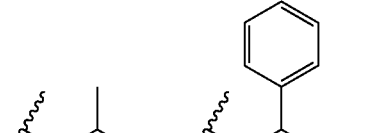

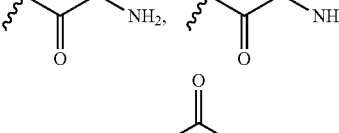

In some embodiments, the compound of the present disclosure has the following structure:

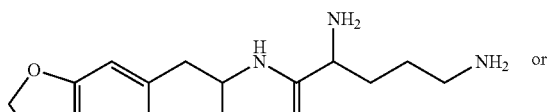

or

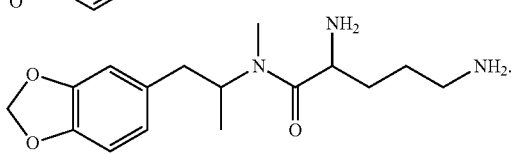

In yet another aspect, the present disclosure provides a compound of Formula (III):

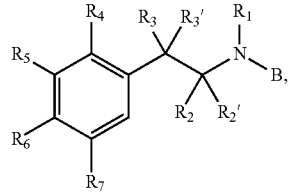

or a pharmaceutically acceptable salt thereof;
wherein,
R$_1$ is H or alkyl;
R$_2$ and R$_{2'}$ are each independently H, halogen, alkyl, —OH, or —O-alkyl, or R$_2$ and R$_{2'}$ together with the atom to which they are attached form a cycloalkyl ring;
R$_3$ and R$_{3'}$ are each independently hydrogen, alkyl, —OH, —O-alkyl, or —O-cycloalkyl, or
R$_3$ and R$_{3'}$ together with the atom to which they are attached form an oxo;
R$_4$, R$_5$, R$_6$ and R$_7$ are each independently hydrogen, halogen, —OH, —O-alkyl, —O-cycloalkyl, alkylene-OR$_8$, —SH, —S-alkyl, —S-cycloalkyl, or alkylene-SR$_8$, or R$_5$ and R$_6$ together with the atoms to which they are attached form a 5- to 8-membered heterocyclyl ring;
R$_8$ is H, alkyl, cycloalkyl, or alkylenecycloalkyl; and
B is

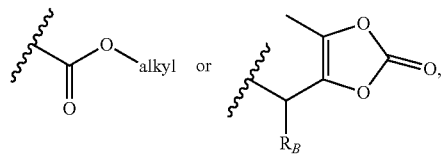

wherein R$_B$ is H or alkyl. In some embodiments, each alkyl is independently a C$_{1-5}$ alkyl.

In some embodiments, the compound of Formula (III) has the following structure:

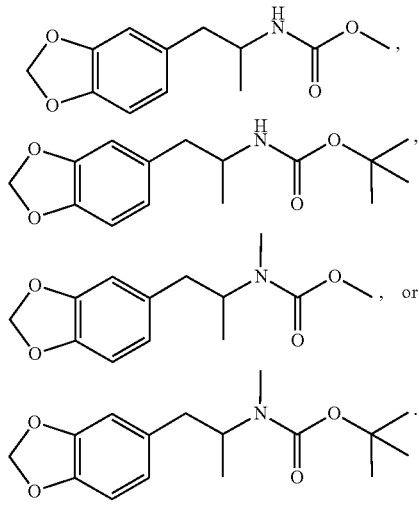

In some embodiments, the compound of Formula (III) has the following structure:

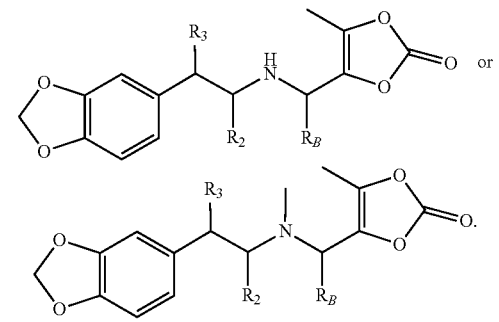

In some embodiments, the compound of Formula (III) has the following structure:

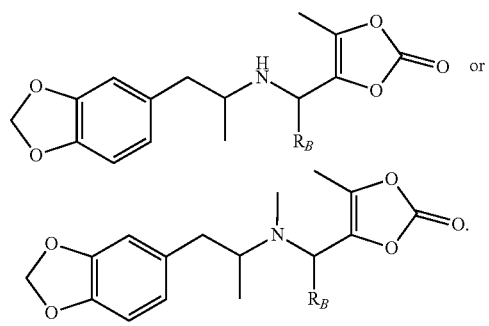

In some embodiments, the compound of Formula (III) has the following structure:

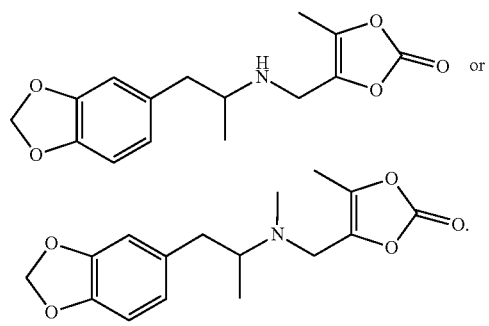

In some embodiments, the compound of Formula (III) has the following structure:

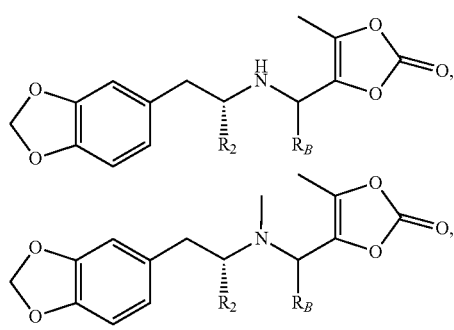

-continued

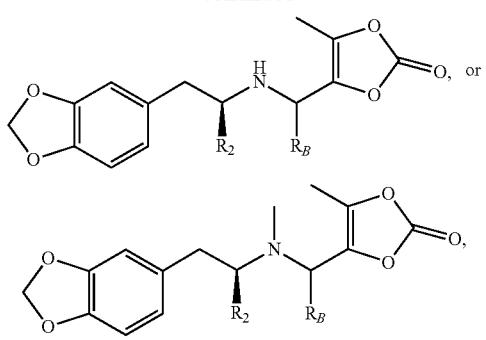

In some embodiments, the compound of Formula (III) has the following structure:

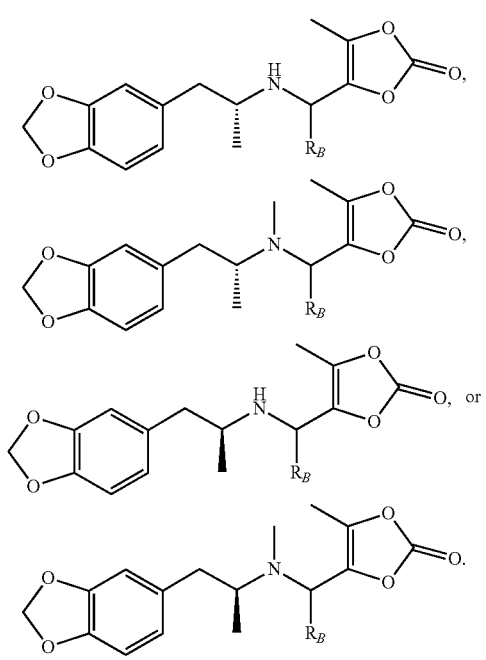

In some embodiments, the compound of Formula (III) has the following structure:

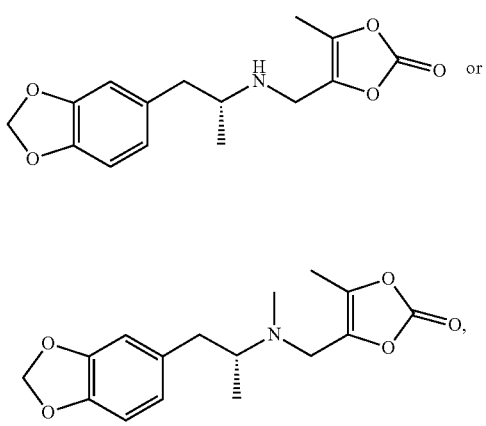

In some embodiments, the compound of Formula (III) has the following structure:

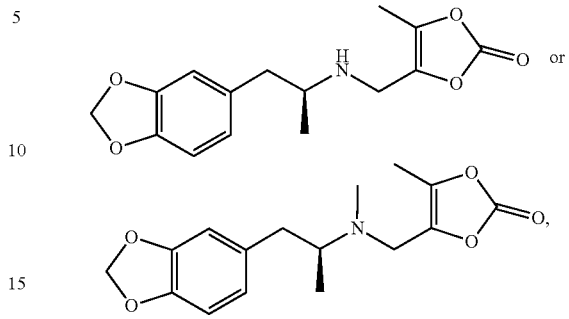

In some embodiments, the pharmaceutical composition of the present disclosure provides an in vivo plasma level characterized by a Cmax of free amine of about 100 ng/mL to about 500 ng/mL, after oral administration of from about 80 mg to about 125 mg of a compound of Formula (I) and release of promoiety X.

In some embodiments, the pharmaceutical composition of the present disclosure provides an in vivo plasma level characterized by an $AUC_{(0-24)}$ of free amine of about 1000 h*ng/mL to about 6000 h*ng/mL, after oral administration of from about 80 mg to about 125 mg of a compound of Formula (I) and release of promoiety X.

In some embodiments, the pharmaceutical composition of the present disclosure provides an in vivo $T_{1/2}$ of free amine of about 5 h to about 15 h, after oral administration of from about 80 mg to about 125 mg of a compound of Formula (I) and release of promoiety X.

In some embodiments, a pharmaceutical composition is provided that comprises a compound of the present disclosure (e.g., a compound of Formula I, II, or III) and one or more pharmaceutically acceptable excipients.

In some embodiments, the present disclosure provides a method of treating a neurological disease or condition in a subject in need thereof, the method comprising, administering to the subject a therapeutically effective amount of a compound or pharmaceutical composition disclosed herein.

Definitions

While the following terms are believed to be well understood by one of ordinary skill in the art, the following definitions are set forth to facilitate explanation of the presently disclosed subject matter.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkoxy" refers to a group of the formula —$OR_a$ where $R_a$ is an alkyl, alkenyl or alkynl as defined above containing one to twelve carbon atoms. Unless stated otherwise specifically in the specification, an alkoxy group can be optionally substituted.

"Aryl" refers to a hydrocarbon ring system comprising hydrogen, 6 to 18 carbon atoms and at least one aromatic ring, and which is attached to the rest of the molecule by a single bond. For purposes of this disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the "aryl" can be optionally substituted.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Carbocyclic rings include aryls and cycloalkyl, cycloalkenyl, and cycloalkynyl as defined herein. Unless stated otherwise specifically in the specification, a carbocyclyl group can be optionally substituted.

"Carbocyclylalkyl" refers to a radical of the formula —$R_b$—$R_d$ where $R_b$ is an alkylene, alkenylene, or alkynylene group as defined above and $R_d$ is a carbocyclyl radical as defined above. Unless stated otherwise specifically in the specification, a carbocyclylalkyl group can be optionally substituted.

"Cycloalkyl" refers to a stable non-aromatic monocyclic or polycyclic fully saturated hydrocarbon consisting solely of carbon and hydrogen atoms, which can include fused or bridged ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Heterocyclyl," "heterocyclic ring" or "heterocycle" refers to a stable saturated, unsaturated, or aromatic 3- to 20-membered ring which includes two to nineteen carbon atoms and from one to six heteroatoms including nitrogen, oxygen or sulfur, and which is attached to the rest of the molecule by a single bond. Heterocyclcl or heterocyclic rings include heteroaryls, heterocyclylalkyls, heterocyclylalkenyls, and hetercyclylalkynyls. Unless stated otherwise specifically in the specification, the heterocyclyl can be a monocyclic, bicyclic, tricyclic or tetracyclic ring system, which can include fused or bridged ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group can be optionally substituted.

"Heteroaryl" refers to a 5- to 20-membered ring system comprising hydrogen atoms, one to nineteen carbon atoms, one to six heteroatoms including nitrogen, oxygen or sulfur, at least one aromatic ring, and which is attached to the rest of the molecule by a single bond. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"Heterocyclylalkyl" refers to a radical of the formula —$R_b$—$R_e$ where $R_b$ is an alkylene, alkenylene, or alkynylene group as defined above and $R_e$ is a heterocyclyl radical as defined above. Unless stated otherwise specifically in the specification, a heterocycloalkylalkyl group can be optionally substituted.

The term "substituted" used herein means any of the groups described herein (e.g., alkyl, alkenyl, alkynyl, alkoxy, aryl, aralkyl, carbocyclyl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, reference to prodrugs of MDMA, MDA, and derivatives thereof includes their (R) and (S) stereoisomers and mixtures thereof, including the racemic mixture. Compounds related to prodrugs of MDMA, as one aspect of the present disclosure, may include compounds which are structurally related to MDMA, but which have modified properties, for example, where the entactogenic effects of MDMA are retained without some of its known adverse effects. Similarly, compounds related to prodrugs, MDA, as one aspect of the present disclosure, may include compounds which are structurally related to MDA, but which have modified properties, for example, where the entactogenic effects of MDA are retained without some of its known adverse effects.

As used herein, the term "promoiety" refers to a functional group used to modify the structure of a pharmacologically active agent (e.g., MDMA, MDA or derivative thereof) to improve physicochemical, biopharmaceutical or pharmacokinetic properties. The promoiety is generally a covalently bonded group that is chemically and/or enzymatically labile in vitro or in vivo. In some embodiments, the active agent-promoiety is pharmacologically inactive or significantly less active than the active agent. Upon cleavage of the promoiety, e.g., by an enzymatic and/or chemical transformation, the active agent is released and able to provide the intended pharmacologic response.

As used herein, the term "free amine" refers to a compound where the promoiety group ("X" is Formula I, "A" in Formula II, and "B" is Formula III) has been cleaved in vitro or in vivo (e.g., by an enzyme in a metabolic reaction) to release the parent amine compound from a prodrug compound of Formula I, II, or III. Accordingly, the free amine compound provided after release of promoiety X, A, or B from a compound of Formula I, II, or III, respectively, can have the structure:

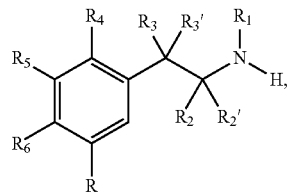

wherein $R_1$, $R_2$, $R_{2'}$, $R_3$, $R_{3'}$, $R_4$, $R_5$, $R_6$, and $R_7$ are as defined herein.

As used herein, the symbol

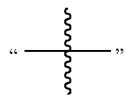

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

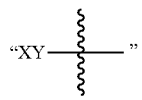

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

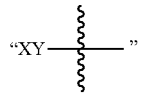

infers that when $R^3$ is "XY", the point of attachment bond is the same bond as the bond by which $R^3$ is depicted as being bonded to $CH_3$.

DETAILED DESCRIPTION

Compounds of the Disclosure

The present disclosure provides compounds that are prodrugs of MDMA, MDA, and derivatives thereof, as well as pharmaceutical compositions thereof.

In some embodiments, the present disclosure provides a compound of Formula (I):

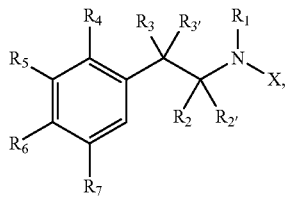

or a pharmaceutically acceptable salt thereof;
wherein:
$R_1$ is H or alkyl;
$R_2$ and $R_{2'}$ are each independently H, halogen, alkyl, —OH, or —O-alkyl, or $R_2$ and $R_{2'}$ together with the atom to which they are attached form a cycloalkyl ring;
$R_3$ and $R_{3'}$ are each independently hydrogen, alkyl, —OH, —O-alkyl, or —O-cycloalkyl, or
$R_3$ and $R_{3'}$ together with the atom to which they are attached form an oxo;
$R_4$, $R_5$, $R_6$ and $R_7$ are each independently hydrogen, halogen, —OH, —O-alkyl, —O-cycloalkyl, alkylene-$OR_8$, —SH, —S-alkyl, —S-cycloalkyl, or alkylene-$SR_8$, or $R_5$ and $R_6$ together with the atoms to which they are attached form a 5- to 8-membered heterocyclyl ring;
$R_8$ is H, alkyl, cycloalkyl, or alkylenecycloalkyl;
X is a cleavable promoiety having the structure

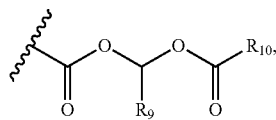

wherein:
$R_9$ and $R_{10}$ are each independently alkyl or aryl.

In some embodiments of Formula (I), $R_1$ is H, alkyl, or cycloalkyl. In some embodiments, $R_1$ is H, $C_1$-$C_6$ alkyl, or $C_3$-$C_6$ cycloalkyl. In some embodiments, $R_1$ is H or $C_1$-$C_6$ alkyl. In some embodiments, $R_1$ is H. In some embodiments, $R_1$ is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl. In some embodiments, $R_1$ is methyl, ethyl, or isopropyl. In some embodiments, $R_1$ is methyl or ethyl. In some embodiments $R_1$ is methyl. In some embodiments, $R_1$ is ethyl. In some embodiments, $R_1$ is isopropyl. In some embodiments, $R_1$ is cyclopropyl.

In some embodiments of Formula (I), $R_2$ and $R_{2'}$ are each independently H, halogen, alkyl, —OH, or —O-alkyl. In some embodiments, $R_2$ and $R_{2'}$ are each independently H, halogen, $C_1$-$C_6$ alkyl, —OH, or —O—$C_1$-$C_6$ alkyl. In some embodiments, $R_2$ and $R_{2'}$ are each independently H or alkyl. In some embodiments, $R_2$ and $R_{2'}$ are each independently H or $C_1$-$C_6$ alkyl. In some embodiments, the halogen is F. In some embodiments, the alkyl is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl.

In some embodiments, $R_2$ and $R_{2'}$ together with the atom to which they are attached form an oxo or a cycloalkyl ring. In some embodiments, $R_2$ and $R_{2'}$ together with the atom to which they are attached form an oxo. In some embodiments, $R_2$ and $R_{2'}$ together with the atom to which they are attached form a cycloalkyl ring. In some embodiments, the cycloalkyl ring is a $C_{3-6}$ cycloalkyl ring. In some embodiments, the cycloalkyl ring is a cyclopropyl. In some embodiments, $R_2$ is alkyl and $R_{2'}$ is H. In some embodiments, $R_2$ is alkyl and $R_{2'}$ is absent. In some embodiments, $R_2$ is H and $R_{2'}$ is alkyl. In some embodiments, $R_2$ is H and $R_{2'}$ is F. In some embodiments, $R_2$ is H and $R_{2'}$ is —OH. In some embodiments, $R_2$ is H and $R_{2'}$ is —OCH$_3$. In some embodiments, $R_2$ is F and $R_{2'}$ is F. In some embodiments, $R_2$ is alkyl and $R_{2'}$ is alkyl. In some embodiments, the alkyl is methyl.

In some embodiments of Formula (I), $R_3$ and $R_{3'}$ are each independently H, halogen, alkyl, —OH, —O-alkyl or —O-cycloalkyl. In some embodiments, $R_3$ and $R_{3'}$ are each independently H, halogen, $C_1$-$C_6$ alkyl, —OH, —O—$C_1$-$C_6$ alkyl, or —O—$C_{3-6}$ cycloalkyl. In some embodiments, $R_3$ and $R_{3'}$ are each independently H or alkyl. In some embodiments, $R_3$ and $R_{3'}$ are each H. In some embodiments, $R_3$ and $R_{3'}$ are each independently H or $C_1$-$C_6$ alkyl. In some embodiments, the halogen is F. In some embodiments, the alkyl is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl.

In some embodiments, $R_3$ and $R_{3'}$ together with the atom to which they are attached form an oxo or a cycloalkyl ring. In some embodiments, $R_3$ and $R_{3'}$ together with the atom to which they are attached form an oxo. In some embodiments, $R_3$ and $R_{3'}$ together with the atom to which they are attached form a cycloalkyl ring. In some embodiments, the cycloalkyl ring is a $C_{3-6}$ cycloalkyl ring. In some embodiments, the cycloalkyl ring is a cyclopropyl. In some embodiments, $R_3$ is H and $R_{3'}$ is alkyl. In some embodiments, $R_3$ is H and $R_{3'}$ is F. In some embodiments, $R_3$ is H and $R_{3'}$ is —OH. In some embodiments, $R_3$ is H and $R_{3'}$ is —OCH$_3$. In some embodiments, $R_3$ is F and $R_{3'}$ is F. In some embodiments, $R_3$ is alkyl and $R_{3'}$ is alkyl. In some embodiments, the alkyl is methyl. In some embodiments, $R_3$ is H and $R_{3'}$ is absent.

In some embodiments of Formula (I), $R_4$, $R_5$, $R_6$ and $R_7$ are each independently hydrogen, halogen, alkyl, —OH, —O-alkyl, —O-cycloalkyl, alkylene-$OR_8$, —SH, —S-alkyl, —S-cycloalkyl, or alkylene-$SR_8$. In some embodiments, $R_4$, $R_5$, $R_6$ and $R_7$ are each independently hydrogen, halogen, —OH, —O-alkyl, —O-cycloalkyl, alkylene-$OR_8$, —SH, —S-alkyl, —S-cycloalkyl, or alkylene-$SR_8$. In some embodiments, $R_4$, $R_5$, $R_6$ and $R_7$ are each independently hydrogen, halogen, —OH, —O—$C_1$-$C_6$ alkyl, —O—$C_3$-$C_6$ cycloalkyl, alkylene-$OR_8$, —SH, —S—$C_1$-$C_6$ alkyl, —S—$C_3$-$C_6$ cycloalkyl, or alkylene-$SR_8$. In some embodiments, $R_4$, $R_5$, $R_6$ and $R_7$ are each independently hydrogen, halogen, —OH, —O-alkyl, —O-cycloalkyl, or alkylene-$OR_8$. In some embodiments, $R_4$, $R_5$, $R_6$ and $R_7$ are each independently hydrogen, halogen, —OH, —O—$C_1$-$C_6$ alkyl, —O—$C_3$-$C_6$ cycloalkyl, or alkylene-$OR_8$. In some embodiments, $R_4$, $R_5$, $R_6$ and $R_7$ are each independently H, halogen, alkyl, —OH, —O-alkyl or —O-cycloalkyl. In some embodiments, $R_4$, $R_5$, $R_6$ and $R_7$ are each independently H, halogen, $C_1$-$C_6$ alkyl, —OH, —O—$C_1$-$C_6$ alkyl, or —O—$C_{3-6}$ cycloalkyl. In some embodiments, $R_4$, $R_5$, $R_6$ and $R_7$ are each independently hydrogen, halogen, —OH, or —O-alkyl. In some embodiments, $R_4$, $R_5$, $R_6$ and $R_7$ are each independently alkylene-$OR_8$, —SH, —S-alkyl, —S-cycloalkyl, or alkylene-$SR_8$. In some embodiments, $R_4$, $R_5$, $R_6$ and $R_7$ are each independently H or —O-alkyl. In some embodiments, $R_4$, $R_5$, $R_6$ and $R_7$ are each independently H or —O—$C_1$-$C_6$ alkyl. In some embodiments, the halogen is F. In some embodiments, the alkyl is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl. In some embodiments, the alkyl is —O—$C_1$-$C_6$ alkyl. In some embodiments, the —O—$C_1$-$C_6$ alkyl is —O-methyl, —O-ethyl, or —O-isopropyl. In some embodiments, the —O—$C_1$-$C_6$ alkyl is —O— methyl or —O-ethyl. In some embodiments, the —O—$C_1$-$C_6$ alkyl is —O-methyl. In some embodiments, the —O—$C_1$-$C_6$ alkyl is ethyl. In some embodiments, the —O—$C_1$-$C_6$ alkyl is —O— isopropyl. In some embodiments, alkylene is a $C_{1-6}$ alkylene. In some embodiments, alkylene is a $C_{1-3}$ alkylene. In some embodiments, alkylene is a methylene or ethylene. In some embodiments, alkylene is methylene.

In some embodiments of Formula (I), $R_8$ is H, alkyl, cycloalkyl, or alkylenecycloalkyl. In some embodiments, $R_8$ is H, alkyl, or alkylenecycloalkyl. In some embodiments, $R_8$ is H or alkyl. In some embodiments, the alkyl is a $C_{1-6}$ alkyl. In some embodiments, the alkylenecycloalkyl is a $C_{1-3}$alkylene-$C_{3-6}$cycloalkyl.

In some embodiments of Formula (I), at least one of $R_4$, $R_5$, $R_6$ and $R_7$ is not H. In some embodiments, at least two of $R_4$, $R_5$, $R_6$ and $R_7$ are not H. In some embodiments, two of $R_4$, $R_5$, $R_6$ and $R_7$ are not H. In some embodiments, $R_5$ and $R_6$ are not H.

In some embodiments of Formula (I), $R_5$ and $R_6$ together with the atoms to which they are attached form a 5- to 8-membered heterocyclyl ring. In some embodiments of Formula (I), $R_5$ and $R_6$ together with the atoms to which they are attached form a 5- or 6-membered heterocyclyl ring. In some embodiments of Formula (I), $R_5$ and $R_6$ together with the atoms to which they are attached form a 5-membered heterocyclyl ring. In some embodiments of Formula (I), $R_5$ and $R_6$ together with the atoms to which they are attached form a 5-membered heterocyclyl ring. In some embodiments, the heterocyclyl ring has one or two oxygen atoms. In some embodiments, the heterocyclyl ring has two oxygen atoms. In some embodiments, the heterocyclic ring is

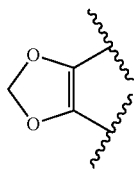 or 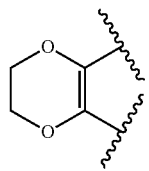.

In some embodiments, the heterocyclic ring is

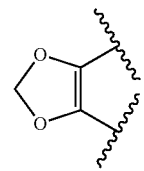

In some embodiments of Formula (I), $R_4$ and $R_7$ are each independently H, halogen (e.g., F, Cl, or Br), or alkyl (e.g., methyl or ethyl) and $R_5$ and $R_6$ are each independently —OH, —O-alkyl, —O-cycloalkyl, alkylene-$OR_8$, —SH, —S-alkyl, —S-cycloalkyl, or alkylene-$SR_8$. In some embodiments, $R_4$ and $R_7$ are each independently H, halogen (e.g., F, Cl, or Br), or alkyl (e.g., methyl or ethyl) and $R_5$ and $R_6$ are each independently —OH, —O-alkyl, —O-cycloalkyl, or alkylene-$OR_8$. In some embodiments, $R_4$ and $R_7$ are each independently H, halogen (e.g., F, Cl, or Br), or alkyl (e.g., methyl or ethyl) and $R_5$ and $R_6$ are each independently —OH, —O—$C_1$-$C_6$ alkyl, —O—$C_3$-$C_6$ cycloalkyl, or alkylene-$OR_8$. In some embodiments, $R_4$ and $R_7$ are each H.

In some embodiments of Formula (I), $R_4$ and $R_7$ are each independently H, halogen (e.g., F, Cl, or Br), or alkyl (e.g., methyl or ethyl) and $R_5$ and $R_6$ together with the atoms to which they are attached form heterocyclyl ring. In some embodiments of Formula (I), $R_4$ and $R_7$ are each independently H, halogen (e.g., F, Cl, or Br), or alkyl (e.g., methyl or ethyl) and $R_5$ and $R_6$ together with the atoms to which they are attached form a 5- or 6-membered heterocyclyl ring. In some embodiments, the heterocyclyl ring has one or two oxygen atoms. In some embodiments, the heterocyclyl ring has two oxygen atoms. In some embodiments, the heterocyclic ring is or

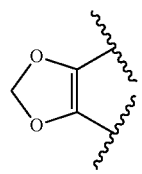 or 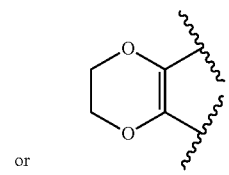.

In some embodiments, the heterocyclic ring is

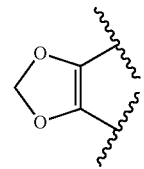.

In some embodiments, $R_4$ and $R_7$ are each H.

In some embodiments, X is a cleavable promoiety that is cleaved at a pH of from about 1 to about 5. In some embodiments, X is a cleavable promoiety that is cleaved at a pH of from about 2 to about 4. In some embodiments, X is a cleaved at pH 2. In some embodiments, X is a cleaved at pH 3. In some embodiments, X is a cleaved at pH 4.

In some embodiments of Formula (I), X is a cleavable promoiety having the structure

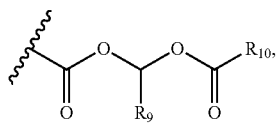

wherein $R_9$ and $R_{10}$ are each independently alkyl or phenyl. In some embodiments of Formula (I), X is a cleavable promoiety having the structure

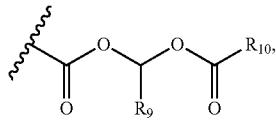

wherein $R_9$ and $R_{10}$ are each independently alkyl. In some embodiments, the alkyl is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl. In some embodiments, $R_9$ and $R_{10}$ are each independently methyl or isopropyl. In some embodiments, $R_9$ and $R_{10}$ are each methyl. In some embodiments, $R_9$ and $R_{10}$ are each ethyl. In some embodiments, $R_9$ and $R_{10}$ are each isopropyl.

In some embodiments, the present disclosure provides a compound of Formula (Ia):

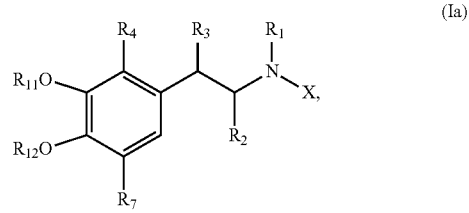

(Ia)

wherein $R_1$, $R_2$, $R_3$, $R_4$, $R_7$, and X are as defined above in Formula (I); and $R_{11}$ and $R_{12}$ are each independently H, alkyl, cycloalkyl, or $R_{11}$ and $R_{12}$ together with the atoms to which they are attached form a 5- to 8-membered heterocyclyl ring.

In some embodiments of Formula (Ia), $R_{11}$ and $R_{12}$ are each independently H, alkyl, alkylenecycloalkyl, or cycloalkyl. In some embodiments, $R_{11}$ and $R_{12}$ are each independently H, $C_{1-5}$ alkyl, $C_{1-3}$alkylene-$C_{3-6}$cycloalkyl, or $C_{3-6}$ cycloalkyl. In some embodiments, $R_{11}$ and $R_{12}$ are each independently H or $C_{1-5}$ alkyl.

In some embodiments of Formula (Ia), $R_{11}$ and $R_{12}$ together with the atoms to which they are attached form a 5- to 8-membered heterocyclyl ring. In some embodiments, $R_{11}$ and $R_{12}$ together with the atoms to which they are attached form a 5- or 6-membered heterocyclyl ring. In some embodiments, $R_{11}$ and $R_{12}$ together with the atoms to which they are attached form a 5-membered heterocyclyl ring. In some embodiments, the heterocyclic ring is

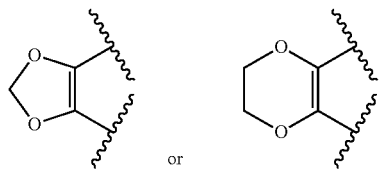

or

In some embodiments, the heterocyclic ring is

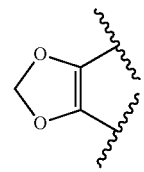

.

In some embodiments, the compound of the present disclosure is a compound of Formula (Ib):

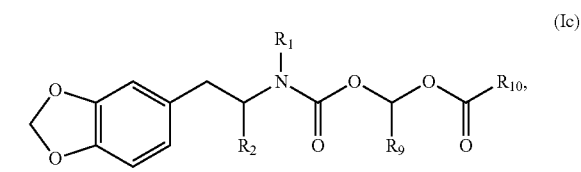

(Ib)

wherein $R_1$, $R_2$, $R_3$, $R_4$, $R_7$, and X are as defined above in Formula (I); and n is 1 or 2.

In some embodiments of Formula (I), n is 1. In some embodiments, n is 2.

In some embodiments, the compound of the present disclosure is a compound of Formula (Ic):

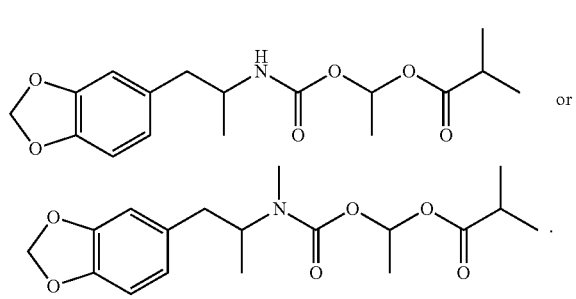

(Ic)

wherein $R_1$, $R_2$, $R_9$ and $R_{10}$ are as defined above in Formula (I). In some embodiments, $R_1$ is H or alkyl; and $R_2$, $R_9$, and $R_{10}$ are each independently Me or iPr.

In some embodiments, the compound of the present disclosure is:

In some embodiments, the present disclosure provides a compound of Formula (II):

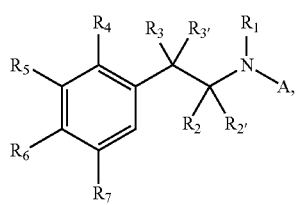

(II)

or a pharmaceutically acceptable salt thereof;
wherein:
$R_1$ is H or alkyl;
$R_2$ and $R_{2'}$ are each independently H, halogen, alkyl, —OH, or —O-alkyl, or $R_2$ and $R_{2'}$ together with the atom to which they are attached form a cycloalkyl ring;
$R_3$ and $R_{3'}$ are each independently hydrogen, alkyl, —OH, —O-alkyl, or —O-cycloalkyl, or
$R_3$ and $R_{3'}$ together with the atom to which they are attached form an oxo;
$R_4$, $R_5$, $R_6$ and $R_7$ are each independently hydrogen, halogen, —OH, —O-alkyl, —O-cycloalkyl, alkylene-$OR_8$, —SH, —S-alkyl, —S-cycloalkyl, or alkylene-$SR_8$, or $R_5$ and $R_6$ together with the atoms to which they are attached form a 5- to 8-membered heterocyclyl ring;
$R_8$ is H, alkyl, cycloalkyl, or alkylenecycloalkyl; and
A is a cleavable promoiety having the structure

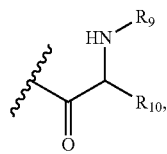

wherein:
$R_9$ is H, alkyl or acyl; and
$R_{10}$ is H, aryl, or —$(CH_2)_m$—$R_{11}$, wherein:
m is an integer from 1-5; and
$R_{11}$ is amino, guanidino, thioalkyl, or aryl.

In some embodiments of Formula (II), $R_1$ is H, alkyl, or cycloalkyl. In some embodiments, $R_1$ is H, $C_1$-$C_6$ alkyl, or $C_3$-$C_6$ cycloalkyl. In some embodiments, $R_1$ is H or $C_1$-$C_6$ alkyl. In some embodiments, $R_1$ is H. In some embodiments, $R_1$ is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl. In some embodiments, $R_1$ is methyl, ethyl, or isopropyl. In some embodiments, $R_1$ is methyl or ethyl. In some embodiments $R_1$ is methyl. In some embodiments, $R_1$ is ethyl. In some embodiments, $R_1$ is isopropyl. In some embodiments, $R_1$ is cyclopropyl.

In some embodiments of Formula (II), $R_2$ and $R_{2'}$ are each independently H, halogen, alkyl, —OH, or —O-alkyl. In some embodiments, $R_2$ and $R_{2'}$ are each independently H, halogen, $C_1$-$C_6$ alkyl, —OH, or —O—$C_1$-$C_6$ alkyl. In some embodiments, $R_2$ and $R_{2'}$ are each independently H or alkyl. In some embodiments, $R_2$ and $R_{2'}$ are each independently H or $C_1$-$C_6$ alkyl. In some embodiments, the halogen is F. In some embodiments, the alkyl is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl.

In some embodiments, $R_2$ and $R_{2'}$ together with the atom to which they are attached form an oxo or a cycloalkyl ring. In some embodiments, $R_2$ and $R_{2'}$ together with the atom to which they are attached form an oxo. In some embodiments, $R_2$ and $R_{2'}$ together with the atom to which they are attached form a cycloalkyl ring. In some embodiments, the cycloalkyl ring is a $C_{3-6}$ cycloalkyl ring. In some embodiments, the cycloalkyl ring is a cyclopropyl. In some embodiments, $R_2$ is alkyl and $R_{2'}$ is H. In some embodiments, $R_2$ is alkyl and $R_{2'}$ is absent. In some embodiments, $R_2$ is H and $R_{2'}$ is alkyl. In some embodiments, $R_2$ is H and $R_{2'}$ is F. In some embodiments, $R_2$ is H and $R_{2'}$ is —OH. In some embodiments, $R_2$ is H and $R_{2'}$ is —$OCH_3$. In some embodiments, $R_2$ is F and $R_{2'}$ is F. In some embodiments, $R_2$ is alkyl and $R_{2'}$ is alkyl. In some embodiments, the alkyl is methyl.

In some embodiments of Formula (II), $R_3$ and $R_{3'}$ are each independently H, halogen, alkyl, —OH, —O-alkyl or —O-cycloalkyl. In some embodiments, $R_3$ and $R_{3'}$ are each independently H, halogen, $C_1$-$C_6$ alkyl, —OH, —O—$C_1$-$C_6$ alkyl, or —O—$C_{3-6}$ cycloalkyl. In some embodiments, $R_3$ and $R_{3'}$ are each independently H or alkyl. In some embodiments, $R_3$ and $R_{3'}$ are each H. In some embodiments, $R_3$ and $R_{3'}$ are each independently H or $C_1$-$C_6$ alkyl. In some embodiments, the halogen is F. In some embodiments, the alkyl is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl.

In some embodiments, $R_3$ and $R_{3'}$ together with the atom to which they are attached form an oxo or a cycloalkyl ring. In some embodiments, $R_3$ and $R_{3'}$ together with the atom to which they are attached form an oxo. In some embodiments, $R_3$ and $R_{3'}$ together with the atom to which they are attached form a cycloalkyl ring. In some embodiments, the cycloalkyl ring is a $C_{3-6}$ cycloalkyl ring. In some embodiments, the cycloalkyl ring is a cyclopropyl. In some embodiments, $R_3$ is H and $R_{3'}$ is alkyl. In some embodiments, $R_3$ is H and $R_{3'}$ is F. In some embodiments, $R_3$ is H and $R_{3'}$ is —OH. In some embodiments, $R_3$ is H and $R_{3'}$ is —$OCH_3$. In some embodiments, $R_3$ is F and $R_{3'}$ is F. In some embodiments, $R_3$ is alkyl and $R_{3'}$ is alkyl. In some embodiments, the alkyl is methyl. In some embodiments, $R_3$ is H and $R_{3'}$ is absent.

In some embodiments of Formula (II), $R_4$, $R_5$, $R_6$ and $R_7$ are each independently hydrogen, halogen, alkyl, —OH, —O-alkyl, —O-cycloalkyl, alkylene-$OR_8$, —SH, —S-alkyl, —S-cycloalkyl, or alkylene-$SR_8$. In some embodiments, $R_4$, $R_5$, $R_6$ and $R_7$ are each independently hydrogen, halogen, —OH, —O-alkyl, —O-cycloalkyl, alkylene-$OR_8$, —SH, —S-alkyl, —S-cycloalkyl, or alkylene-$SR_8$. In some embodiments, $R_4$, $R_5$, $R_6$ and $R_7$ are each independently hydrogen, halogen, —OH, —O—$C_1$-$C_6$ alkyl, —O—$C_3$-$C_6$ cycloalkyl, alkylene-$OR_8$, —SH, —S—$C_1$-$C_6$ alkyl, —S—$C_3$-$C_6$ cycloalkyl, or alkylene-$SR_8$. In some embodiments, $R_4$, $R_8$, $R_6$ and $R_7$ are each independently hydrogen, halogen, —OH, —O-alkyl, —O-cycloalkyl, or alkylene-$OR_8$. In some embodiments, $R_4$, $R_5$, $R_6$ and $R_7$ are each independently hydrogen, halogen, —OH, —O—$C_1$-$C_6$ alkyl, —O—$C_3$-$C_6$ cycloalkyl, or alkylene-$OR_8$. In some embodiments, $R_4$, $R_8$, $R_6$ and $R_7$ are each independently H, halogen, alkyl, —OH, —O-alkyl or —O-cycloalkyl. In some embodiments, $R_4$, $R_5$, $R_6$ and $R_7$ are each independently H, halogen, $C_1$-$C_6$ alkyl, —OH, —O—$C_1$-$C_6$ alkyl, or —O—$C_{3-6}$ cycloalkyl. In some embodiments, $R_4$, $R_5$, $R_6$ and $R_7$ are each independently hydrogen, halogen, —OH, or —O-alkyl. In some embodiments, $R_4$, $R_5$, $R_6$ and $R_7$ are each independently alkylene-$OR_8$, —SH, —S-alkyl, —S-cycloalkyl, or alkylene-$SR_8$. In some embodiments, $R_4$, $R_5$, $R_6$ and $R_7$ are each independently H or —O-alkyl. In some embodiments, $R_4$, $R_5$, $R_6$ and $R_7$ are each independently H or —O—$C_1$-$C_6$ alkyl. In some embodiments, the halogen is F. In some embodiments, the alkyl is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl. In some embodiments, the alkyl is —O—$C_1$-$C_6$ alkyl. In some embodiments, the —O—$C_1$-$C_6$ alkyl is —O-methyl, —O-ethyl, or —O-isopropyl. In some embodiments, the —O—$C_1$-$C_6$ alkyl is —O— methyl or —O-ethyl. In some embodiments, the —O—$C_1$-$C_6$ alkyl is —O-methyl. In some embodiments, the —O—$C_1$-$C_6$ alkyl is ethyl. In some embodiments, the —O—$C_1$-$C_6$ alkyl is —O— isopropyl. In some embodiments, alkylene is a $C_{1-6}$ alkylene. In some embodiments, alkylene is a $C_{1-3}$ alkylene. In some embodiments, alkylene is a methylene or ethylene. In some embodiments, alkylene is methylene.

In some embodiments of Formula (II), $R_8$ is H, alkyl, cycloalkyl, or alkylenecycloalkyl. In some embodiments, $R_8$ is H, alkyl, or alkylenecycloalkyl. In some embodiments, $R_8$ is H or alkyl. In some embodiments, the alkyl is a $C_{1-6}$ alkyl. In some embodiments, the alkylenecycloalkyl is a $C_{1-3}$alkylene-$C_{3-6}$cycloalkyl.

In some embodiments of Formula (II), at least one of $R_4$, $R_5$, $R_6$ and $R_7$ is not H. In some embodiments, at least two of $R_4$, $R_5$, $R_6$ and $R_7$ are not H. In some embodiments, two of $R_4$, $R_5$, $R_6$ and $R_7$ are not H. In some embodiments, $R_5$ and $R_6$ are not H.

In some embodiments of Formula (II), $R_5$ and $R_6$ together with the atoms to which they are attached form a 5- to 8-membered heterocyclyl ring. In some embodiments of Formula (II), $R_5$ and $R_6$ together with the atoms to which they are attached form a 5- or 6-membered heterocyclyl ring. In some embodiments of Formula (II), $R_5$ and $R_6$ together with the atoms to which they are attached form a 5-membered heterocyclyl ring. In some embodiments of Formula (II), $R_5$ and $R_6$ together with the atoms to which they are attached form a 5-membered heterocyclyl ring. In some embodiments, the heterocyclyl ring has one or two oxygen atoms. In some embodiments, the heterocyclyl ring has two oxygen atoms. In some embodiments, the heterocyclic ring is

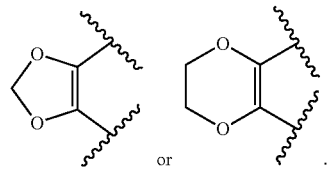 [SMILES: *C1=C(*)OCO1 ; *C1=C(*)OCCO1]

In some embodiments, the heterocyclic ring is

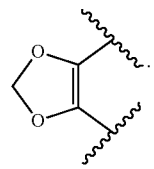 [SMILES: *C1=C(*)OCO1]

In some embodiments of Formula (II), $R_4$ and $R_7$ are each independently H, halogen (e.g., F, Cl, or Br), or alkyl (e.g., methyl or ethyl) and $R_5$ and $R_6$ are each independently —OH, —O-alkyl, —O-cycloalkyl, alkylene-$OR_8$, —SH, —S-alkyl, —S-cycloalkyl, or alkylene-$SR_8$. In some embodiments, $R_4$ and $R_7$ are each independently H, halogen (e.g., F, Cl, or Br), or alkyl (e.g., methyl or ethyl) and $R_5$ and $R_6$ are each independently —OH, —O-alkyl, —O-cycloalkyl, or alkylene-$OR_8$. In some embodiments, $R_4$ and $R_7$ are each independently H, halogen (e.g., F, Cl, or Br), or alkyl (e.g., methyl or ethyl) and $R_5$ and $R_6$ are each independently —OH, —O—$C_1$-$C_6$ alkyl, —O—$C_3$-$C_6$ cycloalkyl, or alkylene-$OR_8$. In some embodiments, $R_4$ and $R_7$ are each H.

In some embodiments of Formula (II), $R_4$ and $R_7$ are each independently H, halogen (e.g., F, Cl, or Br), or alkyl (e.g., methyl or ethyl) and $R_5$ and $R_6$ together with the atoms to which they are attached form heterocyclyl ring. In some embodiments of Formula (II), $R_4$ and $R_7$ are each independently H, halogen (e.g., F, Cl, or Br), or alkyl (e.g., methyl or ethyl) and $R_5$ and $R_6$ together with the atoms to which they are attached form a 5- or 6-membered heterocyclyl ring. In some embodiments, the heterocyclyl ring has one or two oxygen atoms. In some embodiments, the heterocyclyl ring has two oxygen atoms. In some embodiments, the heterocyclic ring is

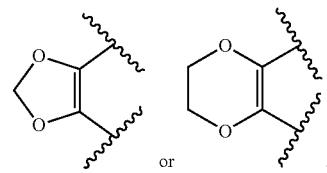

In some embodiments, the heterocyclic ring is

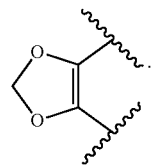 [SMILES: *C1=C(*)OCO1]

In some embodiments, $R_4$ and $R_7$ are each H.

In some embodiments, A is a cleavable promoiety that is cleaved at a pH of from about 7 to about 11. In some embodiments, A is a cleavable promoiety that is cleaved at a pH of from about 8 to about 10. In some embodiments, A is a cleavable promoiety that is cleaved at a pH of from about 8 to about 9. In some embodiments, A is a cleaved at pH 8. In some embodiments, A is a cleaved at pH 9.

In some embodiments of Formula (II), A is a cleavable promoiety having the structure

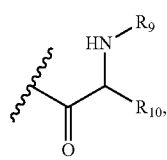

wherein $R_9$ is H or acyl and $R_{10}$ is as defined herein. In some embodiments of Formula (II), A is a cleavable promoiety having the structure

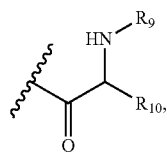

wherein $R_9$ is H or

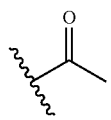

and $R_{10}$ is as defined herein. In some embodiments, $R_{10}$ is H, Ph or —(CH$_2$)$_m$—R$_{11}$, wherein $R_{11}$ is —NH$_2$,

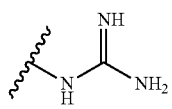

or —SCH$_3$ and m is an integer from 1-5. In some embodiments, m is an integer from 2-4.

In some embodiments, the promoiety A is a group capable of internal release. A specific example of an internally released protecting group utilizes ornithine. The prodrug in such a case can be stabilized to prevent cyclization and release by dosing a salt of the amine or by utilizing a slow release of a secondary protecting group such as a carbamate. Accordingly, in some embodiments, a promoiety A capable of internal release is:

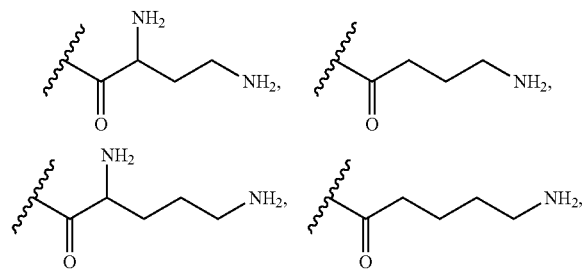

or a pharmaceutically acceptable salt or carbamate thereof.

In some embodiments of Formula (II), promoiety A is:

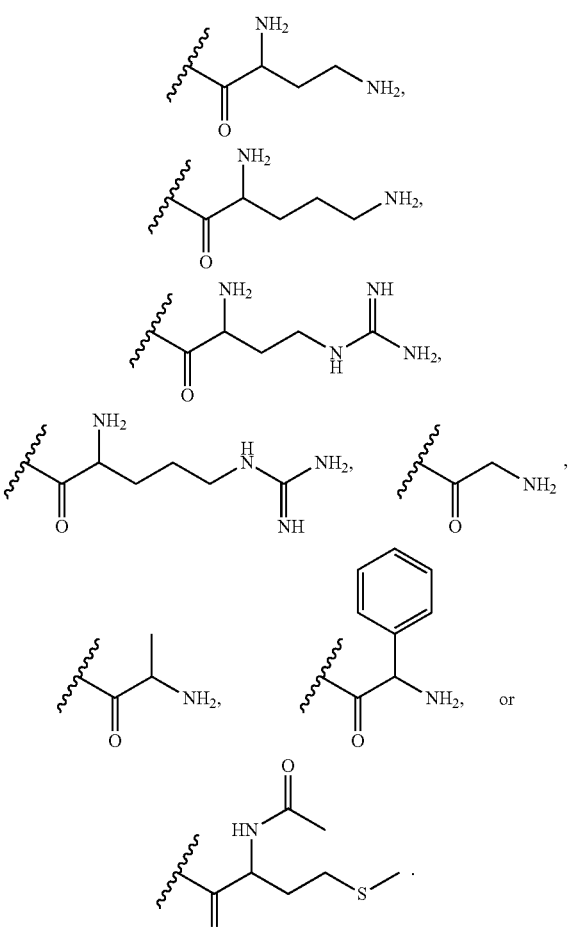

In some embodiments, promoiety A is

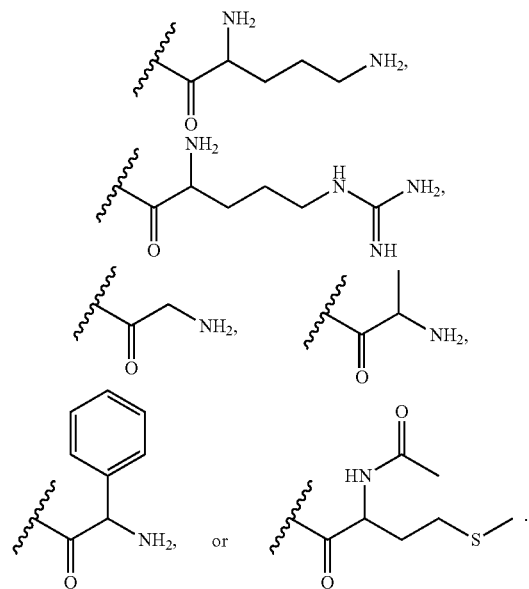

In some embodiments, promoiety A is

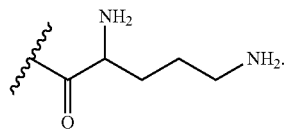 [SMILES: *C(=O)C(N)CCCN]

In some embodiments, the present disclosure provides a compound of Formula (IIa):

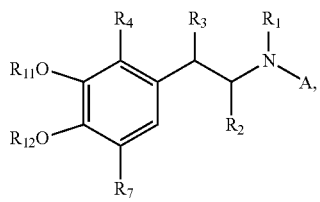

wherein $R_1$, $R_2$, $R_3$, $R_4$, $R_7$, and A are as defined above in Formula (II); and $R_{11}$ and $R_{12}$ are each independently H, alkyl, cycloalkyl, or $R_{11}$ and $R_{12}$ together with the atoms to which they are attached form a 5- to 8-membered heterocyclyl ring.

In some embodiments of Formula (IIa), $R_{11}$ and $R_{12}$ are each independently H, alkyl, alkylenecycloalkyl, or cycloalkyl. In some embodiments, $R_{11}$ and $R_{12}$ are each independently H, $C_{1-5}$ alkyl, $C_{1-3}$alkylene-$C_{3-6}$cycloalkyl, or $C_{3-6}$ cycloalkyl. In some embodiments, Rn and $R_{12}$ are each independently H or $C_{1-5}$ alkyl.

In some embodiments of Formula (IIa), $R_{11}$ and $R_{12}$ together with the atoms to which they are attached form a 5- to 8-membered heterocyclyl ring. In some embodiments, $R_{11}$ and $R_{12}$ together with the atoms to which they are attached form a 5- or 6-membered heterocyclyl ring. In some embodiments, $R_{11}$ and $R_{12}$ together with the atoms to which they are attached form a 5-membered heterocyclyl ring. In some embodiments, the heterocyclic ring is

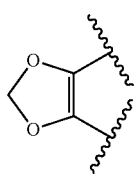 or 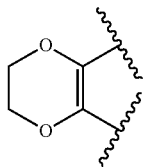.

In some embodiments, the heterocyclic ring is

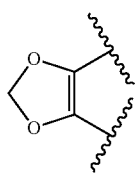.

In some embodiments, the compound of the present disclosure is a compound of Formula (IIb):

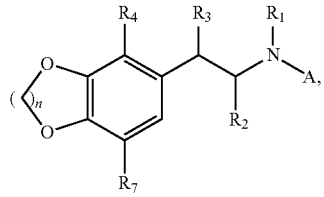

wherein $R_1$, $R_2$, $R_3$, $R_4$, $R_7$, and A are as defined above in Formula (II); and n is 1 or 2.

In some embodiments of Formula (II), n is 1. In some embodiments, n is 2.

In some embodiments, the compound of the present disclosure is a compound of Formula (IIc):

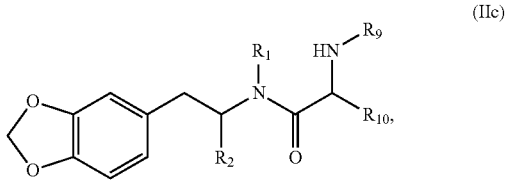

wherein $R_1$, $R_2$, $R_9$ and $R_{10}$ are as defined above in Formula (II). In some embodiments, $R_1$ is H or alkyl (e.g., Me, Et or iPr); $R_2$ is alkyl (e.g., Me, Et, or iPr); $R_9$ is H or —C(O)CH$_3$; and $R_{10}$ is H, Ph or —(CH$_2$)$_m$—$R_{11}$, wherein $R_{11}$ is —NH$_2$,

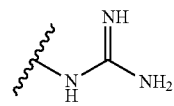

or —SCH$_3$ and m is an integer from 2-4.

In some embodiments, the compound of the present disclosure is:

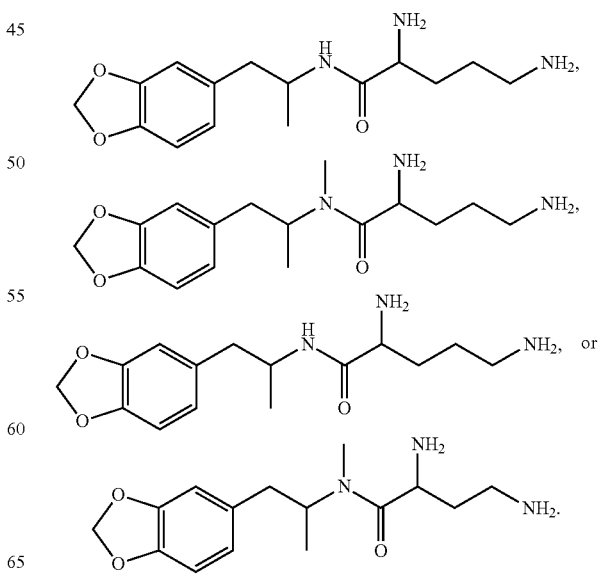

In some embodiments, the compound of the present disclosure is

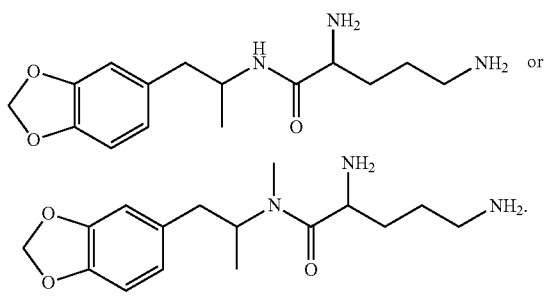

In some embodiments, the present disclosure provides a compound of Formula (III):

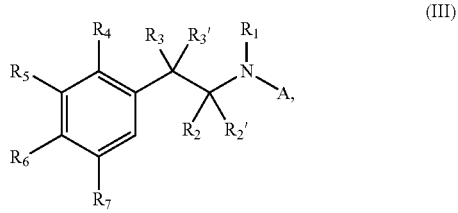

or a pharmaceutically acceptable salt thereof;
wherein:
$R_1$ is H or alkyl;
$R_2$ and $R_{2'}$ are each independently H, halogen, alkyl, —OH, or —O-alkyl, or $R_2$ and $R_{2'}$ together with the atom to which they are attached form a cycloalkyl ring;
$R_3$ and $R_{3'}$ are each independently hydrogen, alkyl, —OH, —O-alkyl, or —O-cycloalkyl, or
$R_3$ and $R_{3'}$ together with the atom to which they are attached form an oxo;
$R_4$, $R_5$, $R_6$ and $R_7$ are each independently hydrogen, halogen, —OH, —O-alkyl, —O— cycloalkyl, alkylene-$OR_8$, —SH, —S-alkyl, —S-cycloalkyl, or alkylene-$SR_8$, or $R_5$ and $R_6$ together with the atoms to which they are attached form a 5- to 8-membered heterocyclyl ring;
$R_8$ is H, alkyl, cycloalkyl, or alkylenecycloalkyl; and
B is

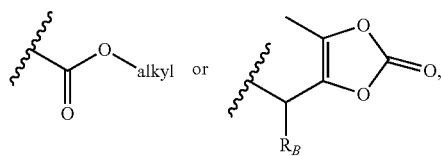

wherein $R_B$ is H or alkyl.

In some embodiments of Formula (III), $R_1$ is H, alkyl, or cycloalkyl. In some embodiments, $R_1$ is H, $C_1$-$C_6$ alkyl, or $C_3$-$C_6$ cycloalkyl. In some embodiments, $R_1$ is H or $C_1$-$C_6$ alkyl. In some embodiments, $R_1$ is H. In some embodiments, $R_1$ is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl. In some embodiments, $R_1$ is methyl, ethyl, or isopropyl. In some embodiments, $R_1$ is methyl or ethyl. In some embodiments $R_1$ is methyl. In some embodiments, $R_1$ is ethyl. In some embodiments, $R_1$ is isopropyl. In some embodiments, $R_1$ is cyclopropyl.

In some embodiments of Formula (III), $R_2$ and $R_{2'}$ are each independently H, halogen, alkyl, —OH, or —O-alkyl. In some embodiments, $R_2$ and $R_{2'}$ are each independently H, halogen, $C_1$-$C_6$ alkyl, —OH, or —O—$C_1$-$C_6$ alkyl. In some embodiments, $R_2$ and $R_{2'}$ are each independently H or alkyl. In some embodiments, $R_2$ and $R_{2'}$ are each independently H or $C_1$-$C_6$ alkyl. In some embodiments, the halogen is F. In some embodiments, the alkyl is $C_1$-$C_6$ alkyl. In some embodiments, the $C_1$-$C_6$ alkyl is methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl.

In some embodiments, $R_2$ and $R_{2'}$ together with the atom to which they are attached form an oxo or a cycloalkyl ring. In some embodiments, $R_2$ and $R_{2'}$ together with the atom to which they are attached form an oxo. In some embodiments, $R_2$ and $R_{2'}$ together with the atom to which they are attached form a cycloalkyl ring. In some embodiments, the cycloalkyl ring is a $C_{3-6}$ cycloalkyl ring. In some embodiments, the cycloalkyl ring is a cyclopropyl. In some embodiments, $R_2$ is alkyl and $R_{2'}$ is H. In some embodiments, $R_2$ is alkyl and $R_{2'}$ is absent. In some embodiments, $R_2$ is H and $R_{2'}$ is alkyl. In some embodiments, $R_2$ is H and $R_{2'}$ is F. In some embodiments, $R_2$ is H and $R_{2'}$ is —OH. In some embodiments, $R_2$ is H and $R_{2'}$ is —$OCH_3$. In some embodiments, $R_2$ is F and $R_{2'}$ is F. In some embodiments, $R_2$ is alkyl and $R_{2'}$ is alkyl. In some embodiments, the alkyl is methyl.

In some embodiments of Formula (III), $R_3$ and $R_{3'}$ are each independently H, halogen, alkyl, —OH, —O-alkyl or —O-cycloalkyl. In some embodiments, $R_3$ and $R_{3'}$ are each independently H, halogen, $C_1$-$C_6$ alkyl, —OH, —O—$C_1$-$C_6$ alkyl, or —O—$C_{3-6}$ cycloalkyl. In some embodiments, $R_3$ and $R_{3'}$ are each independently H or alkyl. In some embodiments, $R_3$ and $R_{3'}$ are each H. In some embodiments, $R_3$ and $R_{3'}$ are each independently H or $C_1$-$C_6$ alkyl. In some embodiments, the halogen is F. In some embodiments, the alkyl is $C_1$-$C_6$ alkyl. In some embodiments, the $C_1$-$C_6$ alkyl is selected from the group consisting of methyl, ethyl, or isopropyl. In some embodiments, the $C_1$-$C_6$ alkyl is methyl or ethyl. In some embodiments, the $C_1$-$C_6$ alkyl is methyl. In some embodiments, the $C_1$-$C_6$ alkyl is ethyl. In some embodiments, the $C_1$-$C_6$ alkyl is isopropyl.

In some embodiments, $R_3$ and $R_{3'}$ together with the atom to which they are attached form an oxo or a cycloalkyl ring. In some embodiments, $R_3$ and $R_{3'}$ together with the atom to which they are attached form an oxo. In some embodiments, $R_3$ and $R_{3'}$ together with the atom to which they are attached form a cycloalkyl ring. In some embodiments, the cycloalkyl ring is a $C_{3-6}$ cycloalkyl ring. In some embodiments, the cycloalkyl ring is a cyclopropyl. In some embodiments, $R_3$ is H and $R_{3'}$ is alkyl. In some embodiments, $R_3$ is H and $R_{3'}$ is F. In some embodiments, $R_3$ is H and $R_{3'}$ is —OH. In some embodiments, $R_3$ is H and $R_{3'}$ is —$OCH_3$. In some embodiments, $R_3$ is F and $R_{3'}$ is F. In some embodiments, $R_3$ is alkyl and $R_{3'}$ is alkyl. In some embodiments, the alkyl is methyl. In some embodiments, $R_3$ is H and $R_{3'}$ is absent.

In some embodiments of Formula (III), $R_4$, $R_5$, $R_6$ and $R_7$ are each independently hydrogen, halogen, alkyl, —OH, —O-alkyl, —O-cycloalkyl, alkylene-$OR_8$, —SH, —S-alkyl, —S-cycloalkyl, or alkylene-$SR_8$. In some embodiments, $R_4$, $R_5$, $R_6$ and $R_7$ are each independently hydrogen, halogen, —OH, —O-alkyl, —O-cycloalkyl, alkylene-OR$_8$, —SH, —S-alkyl, —S-cycloalkyl, or alkylene-SR$_8$. In some embodiments, R$_4$, R$_5$, R$_6$ and R$_7$ are each independently hydrogen, halogen, —OH, —O—C$_1$-C$_6$ alkyl, —O—C$_3$-C$_6$ cycloalkyl, alkylene-OR$_8$, —SH, —S—C$_1$-C$_6$ alkyl, —S—C$_3$-C$_6$ cycloalkyl, or alkylene-SR$_8$. In some embodiments, R$_4$, R$_5$, R$_6$ and R$_7$ are each independently hydrogen, halogen, —OH, —O-alkyl, —O-cycloalkyl, or alkylene-OR$_8$. In some embodiments, R$_4$, R$_5$, R$_6$ and R$_7$ are each independently hydrogen, halogen, —OH, —O—C$_1$-C$_6$ alkyl, —O—C$_3$-C$_6$ cycloalkyl, or alkylene-OR$_8$. In some embodiments, R$_4$, R$_5$, R$_6$ and R$_7$ are each independently H, halogen, alkyl, —OH, —O-alkyl or —O-cycloalkyl. In some embodiments, R$_4$, R$_5$, R$_6$ and R$_7$ are each independently H, halogen, C$_1$-C$_6$ alkyl, —OH, —O—C$_1$-C$_6$ alkyl, or —O—C$_{3-6}$ cycloalkyl. In some embodiments, R$_4$, R$_5$, R$_6$ and R$_7$ are each independently hydrogen, halogen, —OH, or —O-alkyl. In some embodiments, R$_4$, R$_5$, R$_6$ and R$_7$ are each independently alkylene-OR$_8$, —SH, —S-alkyl, —S-cycloalkyl, or alkylene-SR$_8$. In some embodiments, R$_4$, R$_5$, R$_6$ and R$_7$ are each independently H or —O-alkyl. In some embodiments, R$_4$, R$_5$, R$_6$ and R$_7$ are each independently H or —O—C$_1$-C$_6$ alkyl. In some embodiments, the halogen is F. In some embodiments, the alkyl is C$_1$-C$_6$ alkyl. In some embodiments, the C$_1$-C$_6$ alkyl is selected from the group consisting of methyl, ethyl, or isopropyl. In some embodiments, the C$_1$-C$_6$ alkyl is methyl or ethyl. In some embodiments, the C$_1$-C$_6$ alkyl is methyl. In some embodiments, the C$_1$-C$_6$ alkyl is ethyl. In some embodiments, the C$_1$-C$_6$ alkyl is isopropyl. In some embodiments, the alkyl is —O—C$_1$-C$_6$ alkyl. In some embodiments, the —O—C$_1$-C$_6$ alkyl is —O-methyl, —O-ethyl, or —O-isopropyl. In some embodiments, the —O—C$_1$-C$_6$ alkyl is —O-methyl or —O-ethyl. In some embodiments, the —O—C$_1$-C$_6$ alkyl is —O-methyl. In some embodiments, the —O—C$_1$-C$_6$ alkyl is ethyl. In some embodiments, the —O—C$_1$-C$_6$ alkyl is —O-isopropyl. In some embodiments, alkylene is a C$_{1-6}$ alkylene. In some embodiments, alkylene is a C$_{1-3}$ alkylene. In some embodiments, alkylene is a methylene or ethylene. In some embodiments, alkylene is methylene.

In some embodiments of Formula (III), R$_8$ is H, alkyl, cycloalkyl, or alkylenecycloalkyl. In some embodiments, R$_8$ is H, alkyl, or alkylenecycloalkyl. In some embodiments, R$_8$ is H or alkyl. In some embodiments, the alkyl is a C$_{1-6}$ alkyl. In some embodiments, the alkylenecycloalkyl is a C$_{1-3}$alkylene-C$_{3-6}$cycloalkyl.

In some embodiments of Formula (III), at least one of R$_4$, R$_5$, R$_6$ and R$_7$ is not H. In some embodiments, at least two of R$_4$, R$_5$, R$_6$ and R$_7$ are not H. In some embodiments, two of R$_4$, R$_5$, R$_6$ and R$_7$ are not H. In some embodiments, R$_5$ and R$_6$ are not H.

In some embodiments of Formula (III), R$_5$ and R$_6$ together with the atoms to which they are attached form a 5- to 8-membered heterocyclyl ring. In some embodiments of Formula (III), R$_5$ and R$_6$ together with the atoms to which they are attached form a 5- or 6-membered heterocyclyl ring. In some embodiments of Formula (III), R$_5$ and R$_6$ together with the atoms to which they are attached form a 5-membered heterocyclyl ring. In some embodiments of Formula (III), R$_5$ and R$_6$ together with the atoms to which they are attached form a 5-membered heterocyclyl ring. In some embodiments, the heterocyclyl ring has one or two oxygen atoms. In some embodiments, the heterocyclyl ring has two oxygen atoms. In some embodiments, the heterocyclic ring is

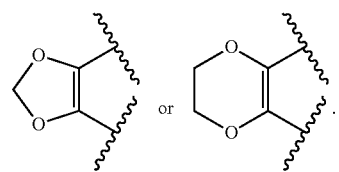 [SMILES: *C1=C(*)OCO1 ; *C1=C(*)OCCO1]

In some embodiments, the heterocyclic ring is

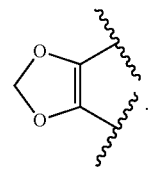 [SMILES: *C1=C(*)OCO1]

In some embodiments of Formula (III), R$_4$ and R$_7$ are each independently H, halogen (e.g., F, Cl, or Br), or alkyl (e.g., methyl or ethyl) and R$_5$ and R$_6$ are each independently —OH, —O-alkyl, —O-cycloalkyl, alkylene-OR$_8$, —SH, —S-alkyl, —S-cycloalkyl, or alkylene-SR$_8$. In some embodiments, R$_4$ and R$_7$ are each independently H, halogen (e.g., F, Cl, or Br), or alkyl (e.g., methyl or ethyl) and R$_5$ and R$_6$ are each independently —OH, —O-alkyl, —O-cycloalkyl, or alkylene-OR$_8$. In some embodiments, R$_4$ and R$_7$ are each independently H, halogen (e.g., F, Cl, or Br), or alkyl (e.g., methyl or ethyl) and R$_5$ and R$_6$ are each independently —OH, —O—C$_1$-C$_6$ alkyl, —O—C$_3$-C$_6$ cycloalkyl, or alkylene-OR$_8$. In some embodiments, R$_4$ and R$_7$ are each H.

In some embodiments of Formula (III), R$_4$ and R$_7$ are each independently H, halogen (e.g., F, Cl, or Br), or alkyl (e.g., methyl or ethyl) and R$_5$ and R$_6$ together with the atoms to which they are attached form heterocyclyl ring. In some embodiments of Formula (III), R$_4$ and R$_7$ are each independently H, halogen (e.g., F, Cl, or Br), or alkyl (e.g., methyl or ethyl) and R$_5$ and R$_6$ together with the atoms to which they are attached form a 5- or 6-membered heterocyclyl ring. In some embodiments, the heterocyclyl ring has one or two oxygen atoms. In some embodiments, the heterocyclyl ring has two oxygen atoms. In some embodiments, the heterocyclic ring is

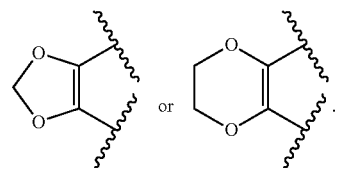 [SMILES: *C1=C(*)OCO1 ; *C1=C(*)OCCO1]

In some embodiments, the heterocyclic ring is

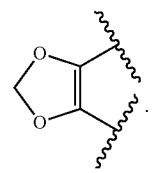

In some embodiments, R$_4$ and R$_7$ are each H.

In some embodiments, B is a cleavable promoiety that is cleaved at a pH of from about 7 to about 11. In some embodiments, B is a cleavable promoiety that is cleaved at a pH of from about 8 to about 10. In some embodiments, B is a cleavable promoiety that is cleaved at a pH of from about 8 to about 9. In some embodiments, B is a cleaved at pH 8. In some embodiments, A is a cleaved at pH 9.

In some embodiments of Formula (III), B is a cleavable promoiety having the structure

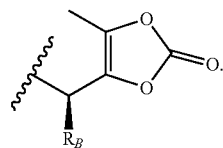

In some embodiments of Formula (III), B is a cleavable promoiety having the structure

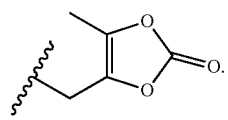 [SMILES: *Cc1oc(=O)oc1C]

In some embodiments of Formula (III), B is a cleavable promoiety having the structure.

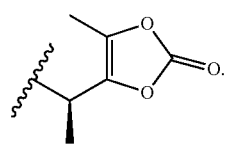 [SMILES: *[C@H](C)c1oc(=O)oc1C]

In some embodiments of Formula (III), B is a cleavable promoiety having the structure

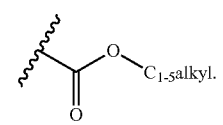

In some embodiments, B is a cleavable promoiety having the structure

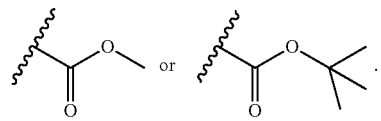

In some embodiments, B is a cleavable promoiety having the structure

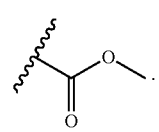

In some embodiments, the present disclosure provides a compound of Formula (IIIa):

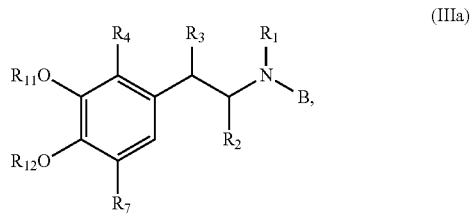

(IIIa)

wherein $R_1$, $R_2$, $R_3$, $R_4$, $R_7$, and B are as defined above in Formula (III); and $R_{11}$ and $R_{12}$ are each independently H, alkyl, cycloalkyl, or $R_1$ and $R_{12}$ together with the atoms to which they are attached form a 5- to 8-membered heterocyclyl ring.

In some embodiments, the present disclosure provides a compound of Formula (IIIa1):

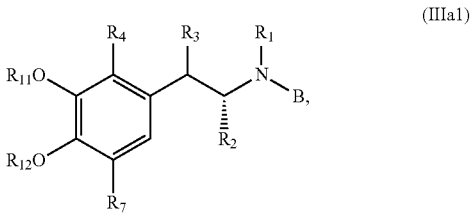

(IIIa1)

wherein $R_1$, $R_2$, $R_3$, $R_4$, $R_7$, and B are as defined above in Formula (III); and $R_{11}$ and $R_{12}$ are each independently H, alkyl, cycloalkyl, or $R_{11}$ and $R_{12}$ together with the atoms to which they are attached form a 5- to 8-membered heterocyclyl ring.

In some embodiments, the present disclosure provides a compound of Formula (IIIa2):

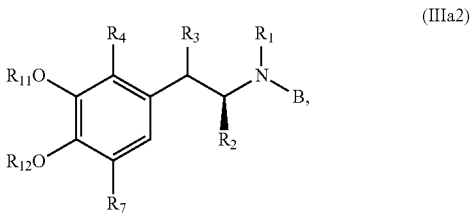

(IIIa2)

wherein $R_1$, $R_2$, $R_3$, $R_4$, $R_7$, and B are as defined above in Formula (III); and $R_{11}$ and $R_{12}$ are each independently H, alkyl, cycloalkyl, or $R_{11}$ and $R_{12}$ together with the atoms to which they are attached form a 5- to 8-membered heterocyclyl ring.

In some embodiments of Formula (IIIa), $R_{11}$ and $R_{12}$ are each independently H, alkyl, alkylenecycloalkyl, or cycloalkyl. In some embodiments, $R_{11}$ and $R_{12}$ are each independently H, $C_{1-5}$ alkyl, $C_{1-3}$alkylene-$C_{3-6}$cycloalkyl, or $C_{3-6}$ cycloalkyl. In some embodiments, Rn and $R_{12}$ are each independently H or $C_{1-5}$ alkyl.

In some embodiments of Formula (IIIa), $R_{11}$ and $R_{12}$ together with the atoms to which they are attached form a 5- to 8-membered heterocyclyl ring. In some embodiments, Rn and $R_{12}$ together with the atoms to which they are attached form a 5- or 6-membered heterocyclyl ring. In some embodiments, $R_{11}$ and $R_{12}$ together with the atoms to which they are attached form a 5-membered heterocyclyl ring. In some embodiments, the heterocyclic ring is

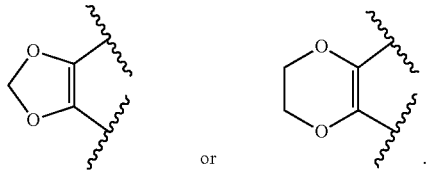 [SMILES: *C1=C(*)OCO1 ; *C1=C(*)OCCO1]

or

In some embodiments, the heterocyclic ring is

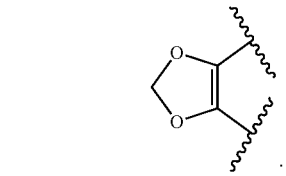 [SMILES: *C1=C(*)OCO1]

In some embodiments, the compound of the present disclosure is a compound of Formula (IIIb):

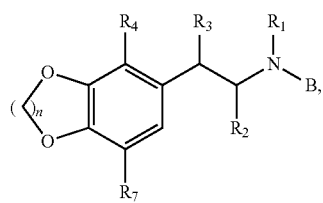

(IIIb)

wherein $R_1$, $R_2$, $R_3$, $R_4$, $R_7$, and B are as defined above in Formula (III); and n is 1 or 2.

In some embodiments, the compound of the present disclosure is a compound of Formula (IIIb1):

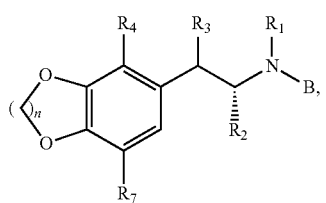

(IIIb1)

wherein $R_1$, $R_2$, $R_3$, $R_4$, $R_7$, an B are as defined above in Formula (III); and n is 1 or 2.

In some embodiments, the compound of the present disclosure is a compound of Formula (IIIb2):

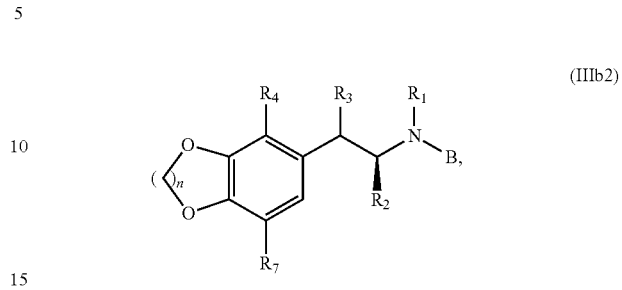

(IIIb2)

wherein $R_1$, $R_2$, $R_3$, $R_4$, $R_7$, and B are as defined above in Formula (III); and n is 1 or 2.

In some embodiments of Formula (III), n is 1. In some embodiments, n is 2.

In some embodiments, the compound of the present disclosure is a compound of Formula (IIIc):

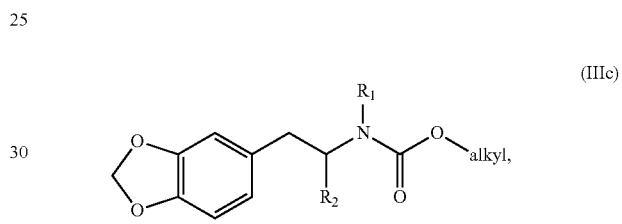

(IIIc)

wherein $R_1$ and $R_2$ are as defined above in Formula (III). In some embodiments, $R_1$ is H or alkyl (e.g., Me or iPr); and $R_2$ is alkyl (e.g., Me or iPr). In some embodiments, $R_1$ is H or Me; and $R_2$ is Me or iPr.

In some embodiments, the compound of the present disclosure is:

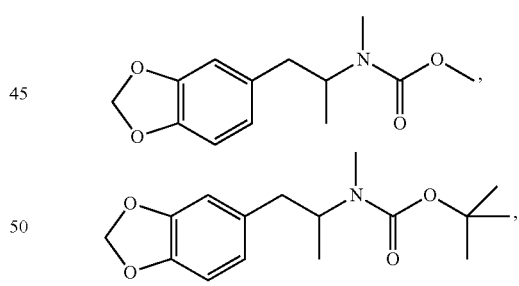

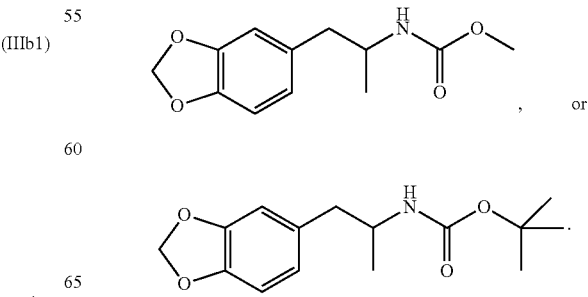

In some embodiments, the compound of the present disclosure is a compound of Formula (IIId):

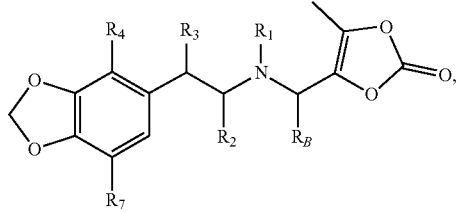
(IIId)

wherein $R_1$, $R_2$, $R_3$, $R_4$, and $R_7$ are as defined above in Formula (III); and $R_B$ is H or alkyl. In some embodiments, $R_1$ is H or alkyl (e.g., Me or iPr); and $R_2$ is alkyl (e.g., Me or iPr). In some embodiments, $R_1$ is H or Me; and $R_2$ is Me or iPr.

In some embodiments, the compound of the present disclosure is a compound of Formula (IIId1):

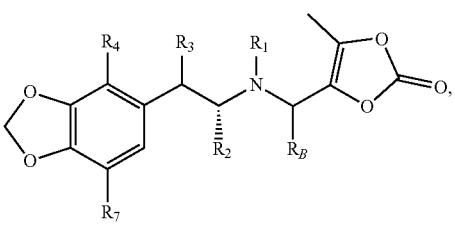
(IIId1)

wherein $R_1$, $R_2$, $R_3$, $R_4$, and $R_7$ are as defined above in Formula (III); and $R_B$ is H or alkyl. In some embodiments, $R_1$ is H or alkyl (e.g., Me or iPr); and $R_2$ is alkyl (e.g., Me or iPr). In some embodiments, $R_1$ is H or Me; and $R_2$ is Me or iPr.

In some embodiments, the compound of the present disclosure is a compound of Formula (IIId1a):

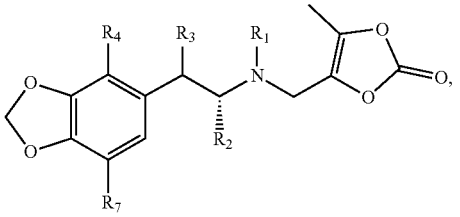
(IIId1a)

wherein $R_1$, $R_2$, $R_3$, $R_4$, and $R_7$ are as defined above in Formula (III). In some embodiments, $R_1$ is H or alkyl (e.g., Me or iPr); and $R_2$ is alkyl (e.g., Me or iPr). In some embodiments, $R_1$ is H or Me; and $R_2$ is Me or iPr.

In some embodiments, the compound of the present disclosure is a compound of Formula (IIId1b):

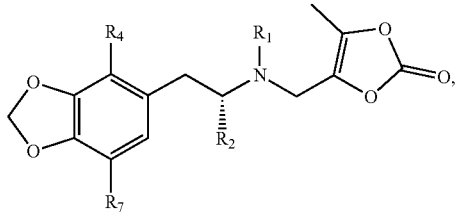
(IIId1b)

wherein $R_1$, $R_2$, $R_4$, and $R_7$ are as defined above in Formula (III). In some embodiments, $R_1$ is H or alkyl (e.g., Me or iPr); and $R_2$ is alkyl (e.g., Me or iPr). In some embodiments, $R_1$ is H or Me; and $R_2$ is Me or iPr.

In some embodiments, the compound of the present disclosure is a compound of Formula (IIId2):

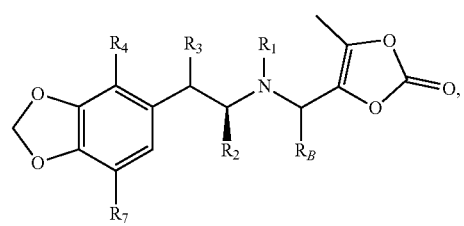
(IIId2)

wherein $R_1$, $R_2$, $R_3$, $R_4$, and $R_7$ are as defined above in Formula (III); and $R_B$ is H or alkyl. In some embodiments, $R_1$ is H or alkyl (e.g., Me or iPr); and $R_2$ is alkyl (e.g., Me or iPr). In some embodiments, $R_1$ is H or Me; and $R_2$ is Me or iPr.

In some embodiments, the compound of the present disclosure is a compound of Formula (IIId2a):

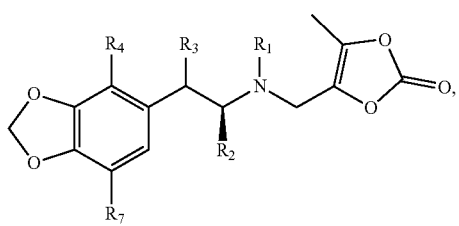
(IIId2a)

wherein $R_1$, $R_2$, $R_3$, $R_4$, and $R_7$ are as defined above in Formula (III). In some embodiments, $R_1$ is H or alkyl (e.g., Me or iPr); and $R_2$ is alkyl (e.g., Me or iPr). In some embodiments, $R_1$ is H or Me; and $R_2$ is Me or iPr.

In some embodiments, the compound of the present disclosure is a compound of Formula (IIId2b):

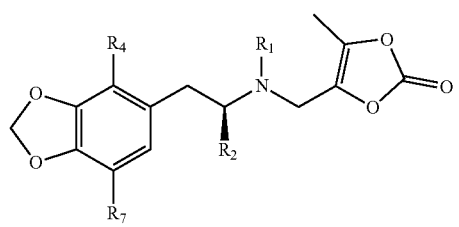
(IIId2b)

wherein $R_1$, $R_2$, $R_4$, and $R_7$ are as defined above in Formula (III). In some embodiments, $R_1$ is H or alkyl (e.g., Me or iPr); and $R_2$ is alkyl (e.g., Me or iPr). In some embodiments, $R_1$ is H or Me; and $R_2$ is Me or iPr.

In some embodiments, the compound of Formula (III) is:

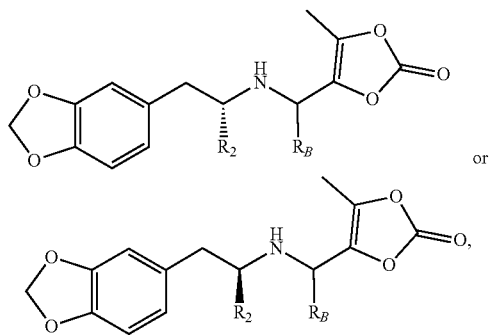

wherein $R_2$ is as defined above in Formula (III); and $R_B$ is H or alkyl.

In some embodiments, the compound of Formula (III) is:

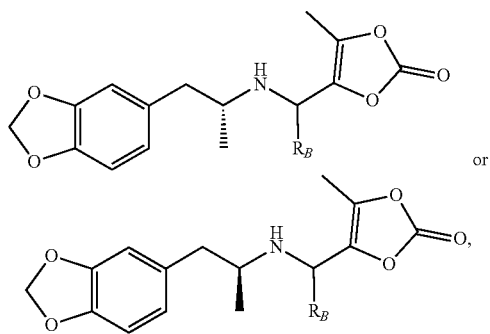

wherein $R_B$ is H or alkyl.

In some embodiments, the compound of Formula (III) is:

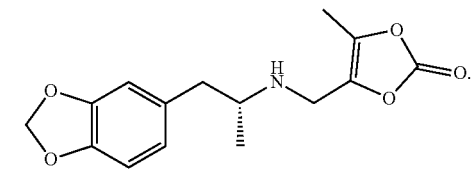 [SMILES: Cc1oc(=O)oc1CN[C@H](C)Cc1ccc2c(c1)OCO2]

In some embodiments, the compound of Formula (III) is:

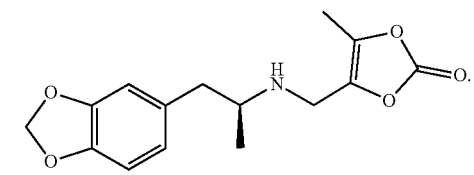

In some embodiments, $R_B$ is H or $C_{1-5}$alkyl. In some embodiments, $R_B$ is H or Me. In some embodiments, $R_B$ is H. In some embodiments, $R_B$ is methyl.

It is contemplated that each of the therapeutic agents may be administered per se as well as in various forms including pharmaceutically acceptable esters, prodrugs, salts, solvates, enantiomers, stereoisomers, active metabolites, co-crystals, and other physiologically functional derivatives thereof. In some embodiments, the prodrugs disclosed herein comprise a mixture of enantiomers, including a racemic mixture thereof. In some embodiments, the prodrugs disclosed herein are enantiomerically pure. In some embodiments, the enantiomeric excess is from 0% (racemic) to 100% (enantiomerically pure), e.g., 0%, 1%, 5%, 10%, 15%, 20%, 25%, 30%, 35%, 40%, 45%, 50%, 55%, 60%, 65%, 70%, 75%, 80%, 85%, 90%, 95%, 99%, or 100%, including all ranges and values therebetween. In some embodiments, the enantiomeric excess is greater than 90%. In some embodiments, the enantiomeric excess is greater than 95%. In some embodiments, the enantiomeric excess is greater than 90%. In some embodiments, the enantiomeric excess is greater than 99%.

Pharmaceutical Compositions of the Present Disclosure

In various embodiments, the present disclosure provides a pharmaceutical composition comprising a compound disclosed herein (e.g., a compound of Formula (I), Formula (Ia), Formula (Ib), Formula (Ic), Formula (II), Formula (IIa), Formula (IIb), Formula (IIc), Formula (III), Formula (IIIa), Formula (IIIb), Formula (IIIc), or Formula (IIId)) or a pharmaceutically acceptable salt thereof, and one or more pharmaceutically acceptable excipients.

In some embodiments, the pharmaceutically acceptable salt is a salt of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid, (−L) malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, propionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid.

The pharmaceutically acceptable excipients and adjuvants are added to the composition or formulation for a variety of purposes. In some embodiments, a pharmaceutical composition comprising one or more compounds disclosed herein, or a pharmaceutically acceptable salt thereof, further comprises a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{th}$ Edition (Lippincott Williams & Wilkins, 2005).

For the purposes of this disclosure, the compounds disclosed herein can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

Pharmacokinetics

The administration of pharmaceutical compositions comprising prodrugs of MDMA, MDA, and/or derivatives thereof disclosed herein can result in a measurable modification of the pharmacokinetic profile (e.g., circulating drug concentration) of free MDMA, MDA and/or derivative thereof relative to the administration of each as a free amine drug.

Formula (I)

Accordingly, in some embodiments of Formula (I), a pharmaceutical composition of the present disclosure provides an in vivo plasma level characterized by a Cmax of free amine of about 100 ng/mL to about 500 ng/mL, e.g., 100 ng/mL to about 500 ng/mL, about 100 ng/mL to about 450 ng/mL, 100 ng/mL to about 400 ng/mL, 100 ng/mL to about 350 ng/mL, 100 ng/mL to about 300 ng/mL or 100 ng/mL to about 250 ng/mL, after oral administration of from about 80 mg to about 125 mg of a compound of Formula (I) and release of promoiety X.

In some embodiments of Formula (I), the pharmaceutical composition of the present disclosure provides an in vivo plasma level characterized by an AUC$_{(0-24)}$ of free amine of about 1000 h*ng/mL to about 6000 h*ng/mL, e.g., 1000 h*ng/mL to about 6000 h*ng/mL, 1000 h*ng/mL to about 5500 h*ng/mL, 1000 h*ng/mL to about 5000 h*ng/mL, 1000 h*ng/mL to about 4500 h*ng/mL, 1000 h*ng/mL to about 4000 h*ng/mL, 1000 h*ng/mL to about 3500 h*ng/mL, or 1000 h*ng/mL to about 3000 h*ng/mL, after oral administration of from about 80 mg to about 125 mg of a compound of Formula (I) and release of promoiety X.

In some embodiments of Formula (I), the pharmaceutical composition of the present disclosure provides an in vivo T$_{1/2}$ of free amine of about 5 h to about 15 h, e.g., about 5 h to about 13 h, about 5 h to about 12 h, about 5 h to about 11 h, about 5 h to about 10 h, about 6 h to about 13 h, about 6 h to about 12 h, about 6 h to about 11 h, or about 6 h to about 10 h, after oral administration of from about 80 mg to about 125 mg of a compound of Formula (I) and release of promoiety X.

In some embodiments of Formula (I), a pharmaceutical composition of the present disclosure provides an in vivo plasma level characterized by a Cmax of free amine that is about 50%, 55%, 60%, 65%, 70%, 75%, 80%, 85%, 90% or 95% of the Cmax achieved upon administration of a 125 mg dose of MDA to a human subject.

In some embodiments of Formula (I), when R$_1$ is H, the composition provides a Cmax of free amine within a range of about 50-90% of about 12 ng/mL to about 15 ng/mL, e.g., about 5.5 ng/mL, about 6 ng/mL, about 6.5 ng/mL, about 7 ng/mL, about 7.5 ng/mL, about 8 ng/mL, about 8.5 ng/mL, about 9 ng/mL, about 9.5 ng/mL, about 10 ng/mL, about 10.5 ng/mL, about 11 ng/mL, about 11.5 ng/mL, about 12 ng/mL, about 12.5 ng/mL, about 13 ng/mL, or about 13.5 ng/mL, achieved following oral administration of about a 125 mg dose of MDA to a human subject.

In some embodiments of Formula (I), a pharmaceutical composition of the present disclosure provides an in vivo plasma level characterized by a Cmax of free amine that is about 50%, 55%, 60%, 65%, 70%, 75%, 80%, 85%, 90% or 95% of the Cmax achieved upon administration of a 75 mg dose of MDA to a human subject.

In some embodiments of Formula (I), when R$_1$ is H, the composition provides a Cmax of free amine within a range of about 50-90% of about 7 ng/mL to about 8.5 ng/mL, e.g., about 3.2 ng/mL, about 3.5 ng/mL, about 3.8 ng/mL, about 4.1 ng/mL, about 4.4 ng/mL, about 4.7 ng/mL, about 5.0 ng/mL, about 5.3 ng/mL, about 5.6 ng/mL, about 5.9 ng/mL, about 6.2 ng/mL, about 6.5 ng/mL, about 6.8 ng/mL, about 7.1 ng/mL, about 7.4 ng/mL, or about 7.7 ng/mL, achieved following oral administration of about a 75 mg dose of MDA to a human subject.

In some embodiments of Formula (I), when R$_1$ is methyl, the composition provides a Cmax of free amine within a range of about 50-90% of about 220 ng/mL to about 250 ng/mL, e.g., about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, or about 230 ng/mL, achieved following oral administration of a 125 mg dose of MDMA to a human subject.

In some embodiments of Formula (I), when R$_1$ is methyl, the composition provides a Cmax of free amine within a range of about 50-90% of about 120 ng/mL to about 140 ng/mL, e.g., about 50 ng/mL, about 60 ng/mL, about 70 ng/mL, about 80 ng/mL, about 90 ng/mL, about 100 ng/mL, about 110 ng/mL, about 120 ng/mL, or about 130 ng/mL, achieved following oral administration of a 75 mg dose of MDMA to a human subject.

In some embodiments of Formula (I), when R$_1$ is methyl, the composition provides a T$_{1/2}$ of free amine within a range of about 105-150% of about 8 h to about 9 h, e.g., about 8.4 h, about 8.8 h, about 9.2 h, about 9.6 h, about 10 h, about 10.4 h, about 10.8 h, about 11.2 h, about 11.6 h, about 12 h, about 12.4 h, about 12.8 h, about 13.2 h, or about 13.6 h, achieved following oral administration of a 125 mg dose of MDMA to a human subject.

In some embodiments of Formula (I), when R$_1$ is methyl, the composition provides a T$_{1/2}$ of free amine within a range of about 105-150% of about 7 h to about 9 h, e.g., about 7.4 h, about 7.6 h, about 8 h, about 8.4 h, about 8.8 h, about 9.2 h, about 9.6 h, about 10 h, about 10.4 h, about 10.8 h, about 11.2 h, about 11.6 h, about 12 h, about 12.4 h, about 12.8 h, about 13.2 h, or about 13.6 h, achieved following oral administration of a 75 mg dose of MDMA to a human subject.

Formula (II)

In some embodiments of Formula (II), a pharmaceutical composition of the present disclosure provides an in vivo plasma level characterized by a Cmax of free amine of about 100 ng/mL to about 500 ng/mL, e.g., 100 ng/mL to about 500 ng/mL, about 100 ng/mL to about 450 ng/mL, 100 ng/mL to about 400 ng/mL, 100 ng/mL to about 350 ng/mL, 100 ng/mL to about 300 ng/mL or 100 ng/mL to about 250 ng/mL, after oral administration of from about 80 mg to about 125 mg of a compound of Formula (II) and release of promoiety A.

In some embodiments of Formula (II), the pharmaceutical composition of the present disclosure provides an in vivo plasma level characterized by an $AUC_{(0-24)}$ of free amine of about 1000 h*ng/mL to about 6000 h*ng/mL, e.g., 1000 h*ng/mL to about 6000 h*ng/mL, 1000 h*ng/mL to about 5500 h*ng/mL, 1000 h*ng/mL to about 5000 h*ng/mL, 1000 h*ng/mL to about 4500 h*ng/mL, 1000 h*ng/mL to about 4000 h*ng/mL, 1000 h*ng/mL to about 3500 h*ng/mL, or 1000 h*ng/mL to about 3000 h*ng/mL, after oral administration of from about 80 mg to about 125 mg of a compound of Formula (II) and release of promoiety A.

In some embodiments of Formula (II), the pharmaceutical composition of the present disclosure provides an in vivo $T_{1/2}$ of free amine of about 5 h to about 15 h, e.g., about 5 h to about 13 h, about 5 h to about 12 h, about 5 h to about 11 h, about 5 h to about 10 h, about 6 h to about 13 h, about 6 h to about 12 h, about 6 h to about 11 h, or about 6 h to about 10 h, after oral administration of from about 80 mg to about 125 mg of a compound of Formula (II) and release of promoiety A.

In some embodiments of Formula (II), a pharmaceutical composition of the present disclosure provides an in vivo plasma level characterized by a Cmax of free amine that is about 50%, 55%, 60%, 65%, 70%, 75%, 80%, 85%, 90% or 95% of the Cmax achieved upon administration of a 75-125 mg dose of MDA to a human subject.

In some embodiments of Formula (II), when $R_1$ is H, the composition provides a Cmax of free amine within a range of about 50-90% of about 12 ng/mL to about 15 ng/mL, e.g., about 5.5 ng/mL, about 6 ng/mL, about 6.5 ng/mL, about 7 ng/mL, about 7.5 ng/mL, about 8 ng/mL, about 8.5 ng/mL, about 9 ng/mL, about 9.5 ng/mL, about 10 ng/mL, about 10.5 ng/mL, about 11 ng/mL, about 11.5 ng/mL, about 12 ng/mL, about 12.5 ng/mL, about 13 ng/mL, or about 13.5 ng/mL, achieved following oral administration of about a 125 mg dose of MDA to a human subject.

In some embodiments of Formula (II), when $R_1$ is H, the composition provides a Cmax of free amine within a range of about 50-90% of about 7 ng/mL to about 8.5 ng/mL, e.g., about 3.2 ng/mL, about 3.5 ng/mL, about 3.8 ng/mL, about 4.1 ng/mL, about 4.4 ng/mL, about 4.7 ng/mL, about 5.0 ng/mL, about 5.3 ng/mL, about 5.6 ng/mL, about 5.9 ng/mL, about 6.2 ng/mL, about 6.5 ng/mL, about 6.8 ng/mL, about 7.1 ng/mL, about 7.4 ng/mL, or about 7.7 ng/mL, achieved following oral administration of about a 75 mg dose of MDA to a human subject.

In some embodiments of Formula (II), a pharmaceutical composition of the present disclosure provides an in vivo plasma level characterized by a Cmax of free amine that is about 50%, 55%, 60%, 65%, 70%, 75%, 80%, 85%, 90% or 95% of the Cmax achieved upon administration of a 75-125 mg dose of MDMA to a human subject.

In some embodiments of Formula (II), when $R_1$ is methyl, the composition provides a Cmax of free amine within a range of about 50-90% of about 220 ng/mL to about 250 ng/mL, e.g., about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, or about 230 ng/mL, achieved following oral administration of a 125 mg dose of MDMA to a human subject.

In some embodiments of Formula (II), when $R_1$ is methyl, the composition provides a Cmax of free amine within a range of about 50-90% of about 120 ng/mL to about 140 ng/mL, e.g., about 50 ng/mL, about 60 ng/mL, about 70 ng/mL, about 80 ng/mL, about 90 ng/mL, about 100 ng/mL, about 110 ng/mL, about 120 ng/mL, or about 130 ng/mL, achieved following oral administration of a 75 mg dose of MDMA to a human subject.

In some embodiments of Formula (II), when $R_1$ is methyl, the composition provides a $T_{1/2}$ of free amine within a range of about 105-150% of about 8 h to about 9 h, e.g., about 8.4 h, about 8.8 h, about 9.2 h, about 9.6 h, about 10 h, about 10.4 h, about 10.8 h, about 11.2 h, about 11.6 h, about 12 h, about 12.4 h, about 12.8 h, about 13.2 h, or about 13.6 h, achieved following oral administration of a 125 mg dose of MDMA to a human subject.

In some embodiments of Formula (II), when $R_1$ is methyl, the composition provides a $T_{1/2}$ of free amine within a range of about 105-150% of about 7 h to about 9 h, e.g., about 7.4 h, about 7.6 h, about 8 h, about 8.4 h, about 8.8 h, about 9.2 h, about 9.6 h, about 10 h, about 10.4 h, about 10.8 h, about 11.2 h, about 11.6 h, about 12 h, about 12.4 h, about 12.8 h, about 13.2 h, or about 13.6 h, achieved following oral administration of a 75 mg dose of MDMA to a human subject.

Formula (III)

In some embodiments of Formula (III), a pharmaceutical composition of the present disclosure provides an in vivo plasma level characterized by a Cmax of free amine of about 100 ng/mL to about 500 ng/mL, e.g., 100 ng/mL to about 500 ng/mL, about 100 ng/mL to about 450 ng/mL, 100 ng/mL to about 400 ng/mL, 100 ng/mL to about 350 ng/mL, 100 ng/mL to about 300 ng/mL or 100 ng/mL to about 250 ng/mL, after oral administration of from about 80 mg to about 125 mg of a compound of Formula (III) and release of promoiety B.

In some embodiments of Formula (III), the pharmaceutical composition of the present disclosure provides an in vivo plasma level characterized by an $AUC_{(0-24)}$ of free amine of about 1000 h*ng/mL to about 6000 h*ng/mL, e.g., 1000 h*ng/mL to about 6000 h*ng/mL, 1000 h*ng/mL to about 5500 h*ng/mL, 1000 h*ng/mL to about 5000 h*ng/mL, 1000 h*ng/mL to about 4500 h*ng/mL, 1000 h*ng/mL to about 4000 h*ng/mL, 1000 h*ng/mL to about 3500 h*ng/mL, or 1000 h*ng/mL to about 3000 h*ng/mL, after oral administration of from about 80 mg to about 125 mg of a compound of Formula (III) and release of promoiety B.

In some embodiments of Formula (III), the pharmaceutical composition of the present disclosure provides an in vivo $T_{1/2}$ of free amine of about 5 h to about 15 h, e.g., about 5 h to about 13 h, about 5 h to about 12 h, about 5 h to about 11 h, about 5 h to about 10 h, about 6 h to about 13 h, about 6 h to about 12 h, about 6 h to about 11 h, or about 6 h to about 10 h, after oral administration of from about 80 mg to about 125 mg of a compound of Formula (III) and release of promoiety B.

In some embodiments of Formula (III), a pharmaceutical composition of the present disclosure provides an in vivo plasma level characterized by a Cmax of free amine that is about 50%, 55%, 60%, 65%, 70%, 75%, 80%, 85%, 90% or 95% of the Cmax achieved upon administration of a 75-125 mg dose of MDA to a human subject.

In some embodiments of Formula (III), when $R_1$ is H, the composition provides a Cmax of free amine within a range of about 50-90% of about 12 ng/mL to about 15 ng/mL, e.g., about 5.5 ng/mL, about 6 ng/mL, about 6.5 ng/mL, about 7 ng/mL, about 7.5 ng/mL, about 8 ng/mL, about 8.5 ng/mL, about 9 ng/mL, about 9.5 ng/mL, about 10 ng/mL, about 10.5 ng/mL, about 11 ng/mL, about 11.5 ng/mL, about 12 ng/mL, about 12.5 ng/mL, about 13 ng/mL, or about 13.5 ng/mL, achieved following oral administration of about a 125 mg dose of MDA to a human subject.

In some embodiments of Formula (III), when $R_1$ is H, the composition provides a Cmax of free amine within a range of about 50-90% of about 7 ng/mL to about 8.5 ng/mL, e.g., about 3.2 ng/mL, about 3.5 ng/mL, about 3.8 ng/mL, about 4.1 ng/mL, about 4.4 ng/mL, about 4.7 ng/mL, about 5.0 ng/mL, about 5.3 ng/mL, about 5.6 ng/mL, about 5.9 ng/mL, about 6.2 ng/mL, about 6.5 ng/mL, about 6.8 ng/mL, about 7.1 ng/mL, about 7.4 ng/mL, or about 7.7 ng/mL, achieved following oral administration of about a 75 mg dose of MDA to a human subject.

In some embodiments of Formula (III), a pharmaceutical composition of the present disclosure provides an in vivo plasma level characterized by a Cmax of free amine that is about 50%, 55%, 60%, 65%, 70%, 75%, 80%, 85%, 90% or 95% of the Cmax achieved upon administration of a 75-125 mg dose of MDMA to a human subject.

In some embodiments of Formula (III), when $R_1$ is methyl, the composition provides a Cmax of free amine within a range of about 50-90% of about 220 ng/mL to about 250 ng/mL, e.g., about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, or about 230 ng/mL, achieved following oral administration of a 125 mg dose of MDMA to a human subject.

In some embodiments of Formula (III), when $R_1$ is methyl, the composition provides a Cmax of free amine within a range of about 50-90% of about 120 ng/mL to about 140 ng/mL, e.g., about 50 ng/mL, about 60 ng/mL, about 70 ng/mL, about 80 ng/mL, about 90 ng/mL, about 100 ng/mL, about 110 ng/mL, about 120 ng/mL, or about 130 ng/mL, achieved following oral administration of a 75 mg dose of MDMA to a human subject.

In some embodiments of Formula (III), when $R_1$ is methyl, the composition provides a $T_{1/2}$ of free amine within a range of about 105-150% of about 8 h to about 9 h, e.g., about 8.4 h, about 8.8 h, about 9.2 h, about 9.6 h, about 10 h, about 10.4 h, about 10.8 h, about 11.2 h, about 11.6 h, about 12 h, about 12.4 h, about 12.8 h, about 13.2 h, or about 13.6 h, achieved following oral administration of a 125 mg dose of MDMA to a human subject.

In some embodiments of Formula (III), when $R_1$ is methyl, the composition provides a $T_{1/2}$ of free amine within a range of about 105-150% of about 7 h to about 9 h, e.g., about 7.4 h, about 7.6 h, about 8 h, about 8.4 h, about 8.8 h, about 9.2 h, about 9.6 h, about 10 h, about 10.4 h, about 10.8 h, about 11.2 h, about 11.6 h, about 12 h, about 12.4 h, about 12.8 h, about 13.2 h, or about 13.6 h, achieved following oral administration of a 75 mg dose of MDMA to a human subject.

Methods of Treatment

In some embodiments, the present disclosure provides a method of treating or preventing neurological disorders in a subject in need thereof, the method comprising administering to the subject a therapeutically effective amount of a compound disclosed herein, e.g., a compound of Formula (I), Formula (Ia), Formula (Ib), Formula (Ic), Formula (II), Formula (IIa), Formula (IIB), Formula (IIc), Formula (III), Formula (IIIa), Formula (IIIb), Formula (IIIc), or Formula (IIId), a pharmaceutically acceptable salt thereof, or a pharmaceutical composition thereof.

In some embodiments, the neurological disorder is a mood disorder. In some embodiments, the mood disorder is clinical depression, postnatal depression or postpartum depression, perinatal depression, atypical depression, melancholic depression, psychotic major depression, cationic depression, seasonal affective disorder, dysthymia, double depression, depressive personality disorder, recurrent brief depression, major depressive disorder, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with neuroendocrine diseases and disorders, neurodegenerative diseases and disorders (e.g., epilepsy), movement disorders, tremor (e.g., Parkinson's Disease), or women's health disorders or conditions. In certain embodiments the mood disorder is depression. In some embodiments, the mood disorder is treatment-resistant depression or major depressive disorder. In some embodiments, the mood disorder is major depressive disorder. In some embodiments, the mood disorder is treatment-resistant depression.

In some embodiments, the present disclosure provides a method of treating or preventing PTSD, mood disorders, general anxiety disorder, addictive disorders, and/or drug dependence in a subject in need thereof, the method comprising administering to the subject a therapeutically effective amount of a compound disclosed herein, e.g., a compound of Formula (I), Formula (Ia), Formula (Ib), Formula (Ic), Formula (II), Formula (IIa), Formula (IIB), Formula (IIc), Formula (III), Formula (IIIa), Formula (IIIb), Formula (IIIc), or Formula (IIId), a pharmaceutically acceptable salt thereof, or a pharmaceutical composition thereof.

In one embodiment, the prodrug of the present disclosure is used to treat PTSD. In one embodiment, the prodrug of the present disclosure is used for induction and maintenance therapy to treat PTSD. In one embodiment, the prodrug of the present disclosure is used to treat PTSD with an improved safety profile when compared to treatment with the entactogenic, oneirophrenic or psychedelic compound (e.g. MDMA or related compound, psilocybin or dimethyltryptamine) alone. In one embodiment, the prodrug of the present disclosure is used for induction and maintenance therapy to treat PTSD with an improved safety profile when compared to treatment with the entactogenic, oneirophrenic or psychedelic compound (e.g. MDMA or related compound, psilocybin or dimethyltryptamine) alone.

In one embodiment, the prodrug of the present disclosure is used to treat behavioral or mood disorders. Examples of behavioral or mood disorders include anxiety, such as social anxiety in autistic subjects (e.g. autistic adults) and anxiety related to life-threatening illnesses, stress (where moderation thereof is measured, for example, by effects on amygdala responses). In some embodiments, the anxiety disorder is panic disorder, obsessive-compulsive disorder, or general anxiety disorder. Other examples include lack of motivation, attention, accuracy, speed of response, perseveration, and/or cognitive engagement. Further examples include depression (e.g., MDD or TRD), attention disorders, disorders of executive function and/or cognitive engagement, obsessive compulsive disorder, bipolar disorder, panic disorder, phobia, schizophrenia, psychopathy, antisocial personality disorder and/or neurocognitive disorders.

In one embodiment, the prodrug of the present disclosure is used to treat an addictive disorder. In some embodiments, the addictive disorder is alcohol abuse, substance abuse, smoking, or obesity. In some embodiments, the disorder is an eating disorder (anorexia nervosa, bulimia, nervosa, binge eating disorder, etc.) or an auditory disorder.

In some embodiments, the disorder is an impulsive disorder. In some embodiments, the impulsive disorder is attention deficit hyperactivity disorder (ADHD), attention deficit disorder (ADD), Tourette's syndrome or autism.

In some embodiments, the disorder is a compulsive disorder. In some embodiments, the compulsive disorder is obsessive compulsive disorder (OCD), gambling, or aberrant sexual behavior.

In some embodiments, the disorder is a personality disorder. In some embodiments, the personality disorder is conduct disorder, antisocial personality, or aggressive behavior.

NUMBERED EMBODIMENTS OF THE DISCLOSURE

1. A compound of Formula (I).

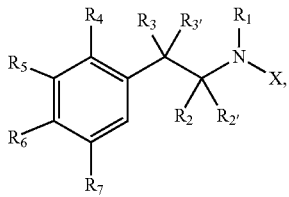
(I)

or a pharmaceutically acceptable salt or enantiomer thereof, wherein,

R₁ is H or alkyl;

R₂ and R₂' are each independently H, halogen, alkyl, —OH, or —O-alkyl, or R₂ and R₂' together with the atom to which they are attached form a cycloalkyl ring;

R₃ and R₃' are each independently hydrogen, alkyl, —OH, —O-alkyl, or —O-cycloalkyl, or R₃ and R₃' together with the atom to which they are attached form an oxo;

R₄, R₅, R₆ and R₇ are each independently hydrogen, halogen, —OH, —O-alkyl, —O— cycloalkyl, alkylene-OR₈, —SH, —S-alkyl, —S-cycloalkyl, or alkylene-SR₈, or R₅ and R₆ together with the atoms to which they are attached form a 5- to 8-membered heterocyclyl ring;

R₈ is H, alkyl, cycloalkyl, or alkylenecycloalkyl;

X is a cleavable promoiety having the structure

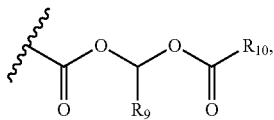

wherein:

R₉ and R₁₀ are each independently alkyl.

1a. The compound of embodiment 1, having the structure:

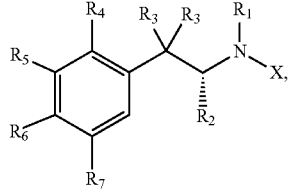

or a pharmaceutically acceptable salt thereof.

1b. The compound of embodiment 1, having the structure:

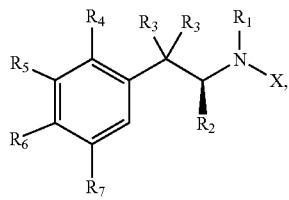

or a pharmaceutically acceptable salt thereof.

2. The compound of embodiment 1, wherein at least one of R₄, R₅, R₆ and R₇ is not H.
3. The compound of embodiment 1 or 2, wherein R₁ is H or C₁-C₆ alkyl.
4. The compound of embodiment 1 or 2, wherein R₁ is H.
5. The compound of embodiment 1 or 2, wherein R₁ is CH₃.
6. The compound of any one of embodiments 1-5, wherein R₂ and R₂' are each independently H, alkyl, or —OH.
7. The compound of any one of embodiments 1-5, wherein R₂ is alkyl and R₂' is H.
8. The compound of any one of embodiments 1-5, wherein R₂ and R₂' are each alkyl.
9. The compound of any one of embodiments 6-8, wherein the alkyl is methyl or isopropyl.
10. The compound of any one of embodiments 1-9, wherein R₃ and R₃' are each independently H, —OH, or —O-alkyl, or R₃ and R₃' together with the atom to which they are attached form an oxo.
10a. The compound of any one of embodiments 1-9, wherein R₃ and R₃' are each H.
11. The compound of any one of embodiments 1-10, wherein R₄ is H.
12. The compound of any one of embodiments 1-11, wherein R₇ is H.
13. The compound of any one of embodiments 1-12, wherein R₅ and R₆ are each independently halogen, —OH, —O-alkyl, —O-cycloalkyl, alkylene-OR₈, —SH, —S-alkyl, —S-cycloalkyl, or alkylene-SR₈.
14. The compound of any one of embodiments 1-12, wherein R₅ and R₆ together with the atoms to which they are attached form a 5- to 8-membered heterocyclyl ring.
15. The compound of any one of embodiments 1-14, wherein R₈ is alkyl.
16. The compound of any one of embodiments 1-15, wherein R₉ is C₁₋₅ alkyl.
17. The compound of any one of embodiments 1-16, wherein R₉ is methyl or isopropyl.
18. The compound of any one of embodiments 1-17, wherein R₁₀ is C₁₋₅ alkyl.

19. The compound of embodiment 18, wherein $R_{10}$ is methyl or isopropyl.

19a. The compound of embodiment 18, wherein $R_{10}$ is methyl, isopropyl, or tert-butyl.

20. The compound of any one of embodiments 1-12 and 14-19a, having the structure of Formula (Ib):

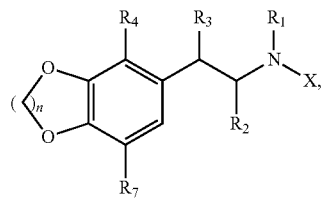

wherein n is 1 or 2.

20a. The compound of embodiment 20, having the structure:

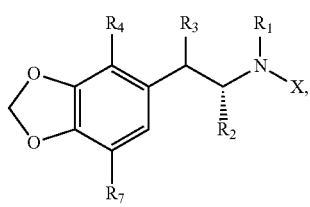

or a pharmaceutically acceptable salt thereof.

20b. The compound of embodiment 20, having the structure:

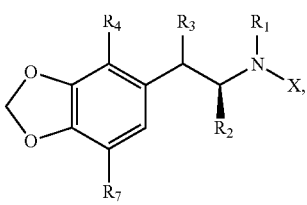

or a pharmaceutically acceptable salt thereof.

20c. The compound of any one of embodiments 20-20b, wherein $R_3$ is H.

21. The compound of any one of embodiments 1-12 and 14-20, wherein the compound is:

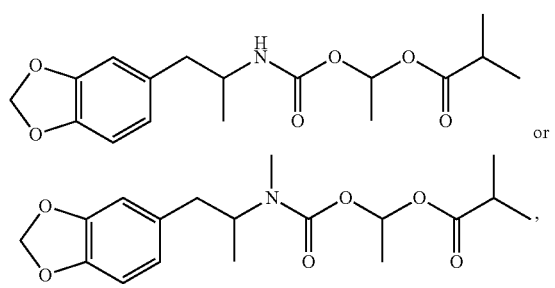

21a. The compound of embodiment 21, wherein the compound is:

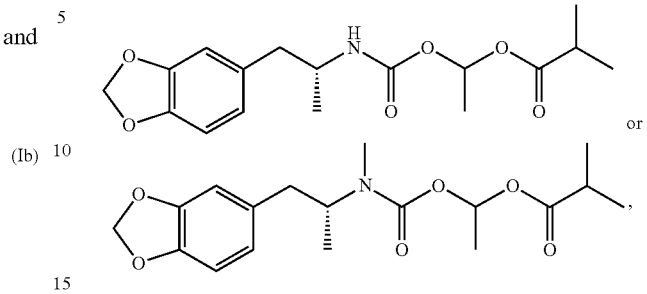

21b. The compound of embodiment 21, wherein the compound is:

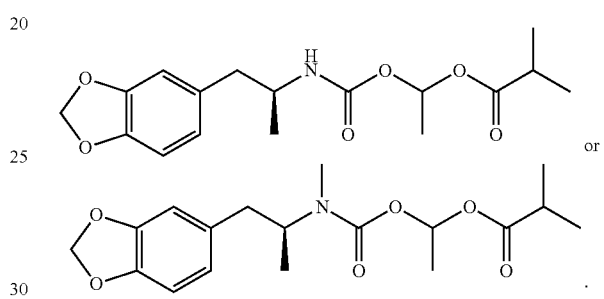

22. The compound of any one of embodiments 1-21b, wherein X is cleavable at a pH of from about 1 to about 5.

23. The compound of any one of embodiments 1-21b, wherein X is cleavable at a pH of from about 2 to about 4.

24. A pharmaceutical composition comprising the compound of any one of embodiments 1-23 and a pharmaceutically acceptable excipient.

25. The pharmaceutical composition of embodiment 24, capable of providing an in vivo plasma level characterized by a Cmax of free amine of about 100 ng/mL to about 500 ng/mL, after oral administration of from about 80 mg to about 125 mg of a compound of Formula (I) and release of promoiety X.

26. The pharmaceutical composition of embodiment 24 or 25, capable of providing an in vivo plasma level characterized by an $AUC_{(0-24)}$ of free amine of about 1000 h*ng/mL to about 6000 h*ng/mL, after oral administration of from about 80 mg to about 125 mg of a compound of Formula (I) and release of promoiety X.

27. The pharmaceutical composition of any one of embodiments 24-26, capable of providing an in vivo $T_{1/2}$ of free amine of about 5 h to about 15 h, after oral administration of from about 80 mg to about 125 mg of a compound of Formula (I) and release of promoiety X.

28. The pharmaceutical composition of embodiment 24, wherein when $R_1$ is H, the composition is capable of providing a Cmax of free amine within a range of about 60-90% of about 12 ng/mL to about 15 ng/mL achieved following oral administration of a 125 mg dose of MDA to a human subject.

29. The pharmaceutical composition of embodiment 24, wherein when $R_1$ is H, the composition is capable of providing a Cmax of free amine within a range of about 60-90% of about 7 ng/mL to about 8.5 ng/mL achieved following oral administration of a 75 mg dose of MDA to a human subject.

30. The pharmaceutical composition of embodiment 22, wherein when $R_1$ is methyl, the composition is capable of providing a Cmax of free amine within a range of about 60-90% of about 220 ng/mL to about 250 ng/mL achieved following oral administration of a 125 mg dose of MDMA to a human subject.

31. The pharmaceutical composition of embodiment 24, wherein $R_1$ is methyl, the composition is capable of providing a $T_{1/2}$ of free amine within a range of about 105-150% of about 8 h to about 9 h achieved following oral administration of a 125 mg dose of MDMA to a human subject.

32. The pharmaceutical composition of embodiment 24, wherein when $R_1$ is methyl, the composition is capable of providing a Cmax of free amine within a range of about 60-90% of about 120 ng/mL to about 140 ng/mL achieved following oral administration of a 75 mg dose of MDMA to a human subject.

33. The pharmaceutical composition of embodiment 24, wherein when $R_1$ is methyl, the composition is capable of providing a $T_{1/2}$ of free amine within a range of 105-150% of about 7 h to about 9 h achieved following oral administration of a 75 mg dose of MDMA to a human subject.

34. A compound of Formula (II):

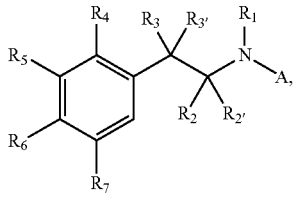

or a pharmaceutically acceptable salt thereof;
wherein,
$R_1$ is H or alkyl;
$R_2$ and $R_{2'}$ are each independently H, halogen, alkyl, —OH, or —O-alkyl, or $R_2$ and $R_{2'}$ together with the atom to which they are attached form a cycloalkyl ring;
$R_3$ and $R_{3'}$ are each independently hydrogen, alkyl, —OH, —O-alkyl, or —O-cycloalkyl, or
$R_3$ and $R_{3'}$ together with the atom to which they are attached form an oxo;
$R_4$, $R_5$, $R_6$ and $R_7$ are each independently hydrogen, halogen, —OH, —O-alkyl, —O—cycloalkyl, alkylene-$OR_8$, —SH, —S-alkyl, —S-cycloalkyl, or alkylene-$SR_8$, or $R_5$ and $R_6$ together with the atoms to which they are attached form a 5- to 8-membered heterocyclyl ring;
$R_8$ is H, alkyl, cycloalkyl, or alkylenecycloalkyl; and
A is a cleavable promoiety having the structure

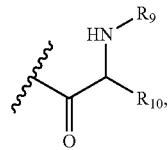

wherein:
$R_9$ is H, alkyl or acyl; and
$R_{10}$ is H, aryl, or —$(CH_2)_m$—$R_{11}$, wherein:
m is an integer from 1-5; and
$R_{11}$ is amino, guanidino, thioalkyl, or aryl.

34a. The compound of embodiment 34, having the structure:

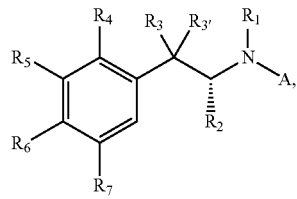

or a pharmaceutically acceptable salt thereof.

34b. The compound of embodiment 34, having the structure:

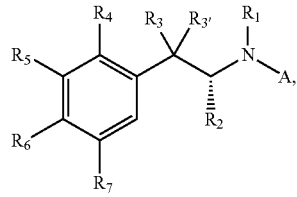

or a pharmaceutically acceptable salt thereof.

35. The compound of any one of embodiments 34-34b, wherein at least one of $R_4$, $R_5$, $R_6$ and $R_7$ is not H.

36. The compound of any one of embodiments 34-35, wherein $R_1$ is H or $C_1$-$C_6$ alkyl.

37. The compound of any one of embodiments 34-35, wherein $R_1$ is H.

38. The compound of any one of embodiments 34-35, wherein $R_1$ is $CH_3$.

39. The compound of any one of embodiments 34-38, wherein $R_2$ and $R_{2'}$ are each independently H, alkyl, or —OH.

40. The compound of any one of embodiments 34-38, wherein $R_2$ is alkyl and $R_{2'}$ is H.

41. The compound of any one of embodiments 34-38, wherein $R_2$ and $R_{2'}$ are each alkyl.

42. The compound of any one of embodiments 39-41, wherein the alkyl is methyl or isopropyl.

43. The compound of any one of embodiments 34-42, wherein $R_3$ and $R_{3'}$ are each independently H, —OH, or —O-alkyl or $R_3$ and $R_{3'}$ together with the atom to which they are attached form an oxo.

43a. The compound of any one of embodiments 34-42, wherein $R_3$ and $R_{3'}$ are each H.

44. The compound of any one of embodiments 34-43, wherein $R_4$ is H.

45. The compound of any one of embodiments 34-44, wherein $R_7$ is H.

46. The compound of any one of embodiments 34-45, wherein $R_5$ and $R_6$ are each independently halogen, —OH, —O-alkyl, —O-cycloalkyl, alkylene-$OR_8$, —SH, —S-alkyl, —S-cycloalkyl, or alkylene-$SR_8$.

47. The compound of any one of embodiments 34-45, wherein $R_5$ and $R_6$ together with the atoms to which they are attached form a 5- or 6-membered heterocyclyl ring.

48. The compound of any one of embodiments 34-47, wherein $R_8$ is alkyl.

49. The compound of any one of embodiments 34-48, wherein $R_9$ is H or.

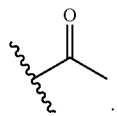

50. The compound of any one of embodiments 34-49, wherein $R_9$ is H.

51. The compound of any one of embodiments 34-50, wherein $R_{10}$ is H, Ph or —(CH$_2$)$_m$—R$_{11}$, and wherein $R_{11}$ is —NH$_2$,

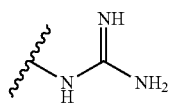

or —SCH$_3$.

52. The compound of embodiment 50 or 51, wherein m is an integer from 2-4.

53. The compound of any one of embodiments 34-52, wherein promoiety A is:

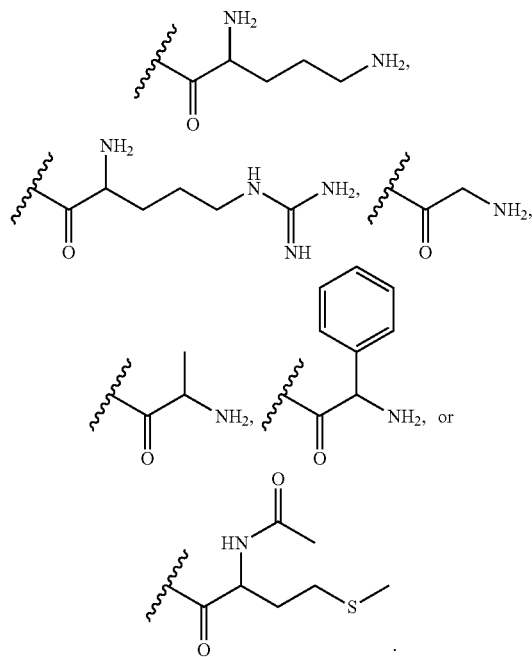

53a. The compound of any one of embodiments 34-52, wherein promoiety A is:

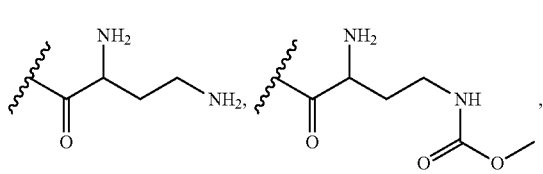

-continued

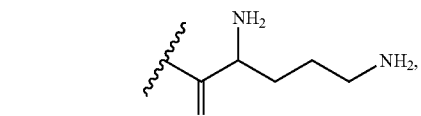

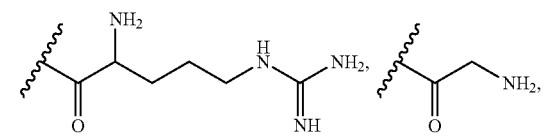

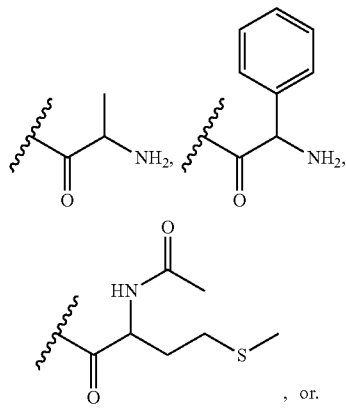

, or.

54. The compound of any one of embodiments 34-53, wherein promoiety A is

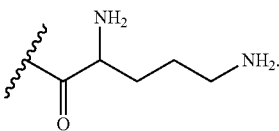 [SMILES: *C(=O)C(N)CCCN]

54a. The compound of any one of embodiments 34-53, wherein promoiety A is

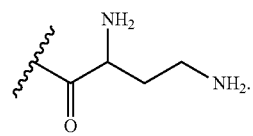 [SMILES: *C(=O)C(N)CCN]

55. The compound of any one of embodiments 34-45 and 47-54a, having the structure of Formula (IIa):

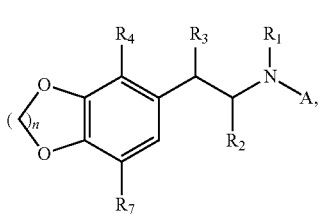

(IIb)

wherein n is 1 or 2.

55a. The compound of embodiment 55, having the structure:

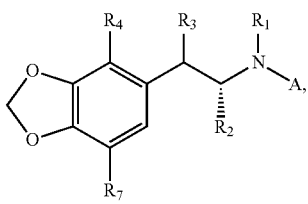

or a pharmaceutically acceptable salt thereof.

55b. The compound of embodiment 55, having the structure:

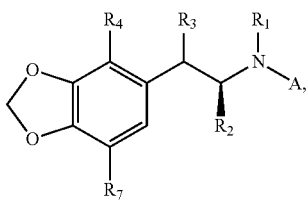

or a pharmaceutically acceptable salt thereof.

55c. The compound of any one of embodiments 55-55b, wherein $R_3$ is H.

56. The compound of any one of embodiments 34-45 and 47-54, wherein the compound is:

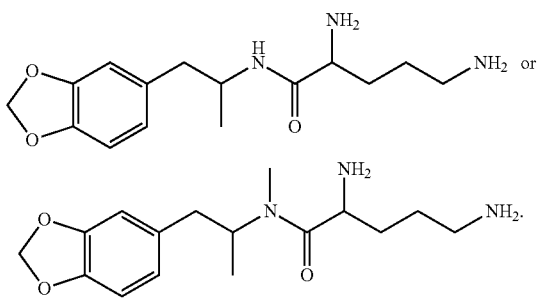

56a. The compound of embodiment 56, wherein the compound is:

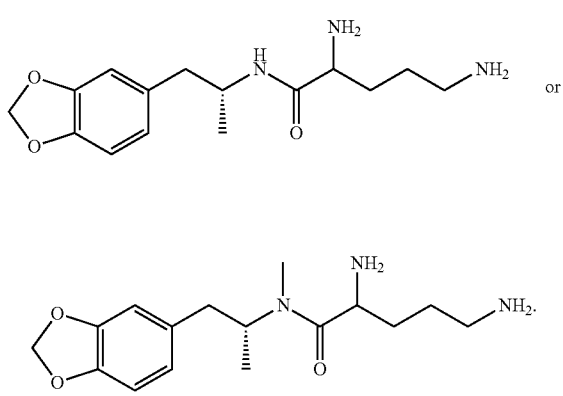

56b. The compound of embodiment 56, wherein the compound is:

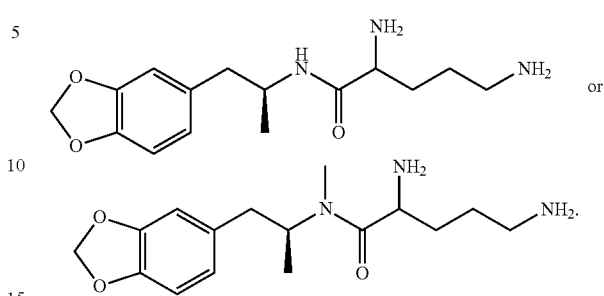

57. The compound of any one of embodiments 34-56b, wherein the promoiety A is cleavable at a pH of from about 8 to about 10.

58. The compound of any one of embodiments 34-56b, wherein the promoiety A is cleavable at a pH of from about 8 or 9.

59. A pharmaceutical composition comprising a compound of any one of embodiments 34-58 and a pharmaceutically acceptable excipient.

60. The pharmaceutical composition of embodiment 59, wherein when $R_1$ is H, the composition is capable of providing a Cmax of free amine within a range of about 60-90% of about 12 ng/mL to about 15 ng/mL achieved following oral administration of a 125 mg dose of MDA to a human subject.

61. The pharmaceutical composition of embodiment 59, wherein when $R_1$ is H, the composition is capable of providing a Cmax of free amine within a range of about 60-90% of about 7 ng/mL to about 8.5 ng/mL achieved following oral administration of a 75 mg dose of MDA to a human subject.

62. The pharmaceutical composition of embodiment 59, wherein when $R_1$ is methyl, the composition is capable of providing a Cmax of free amine within a range of about 60-90% of about 220 ng/mL to about 250 ng/mL achieved following oral administration of a 125 mg dose of MDMA to a human subject.

63. The pharmaceutical composition of embodiment 59, wherein $R_1$ is methyl, the composition is capable of providing a $T_{1/2}$ of free amine within a range of about 105-150% of about 8 h to about 9 h achieved following oral administration of a 125 mg dose of MDMA to a human subject.

64. The pharmaceutical composition of embodiment 59, wherein when $R_1$ is methyl, the composition is capable of providing a Cmax of free amine within a range of about 60-90% of about 120 ng/mL to about 140 ng/mL achieved following oral administration of a 75 mg dose of MDMA to a human subject.

65. The pharmaceutical composition of embodiment 59, wherein when $R_1$ is methyl, the composition is capable of providing a $T_{1/2}$ of free amine within a range of 105-150% of about 7 h to about 9 h achieved following oral administration of a 75 mg dose of MDMA to a human subject.

66. The pharmaceutical composition of embodiment 59, capable of providing an in vivo plasma level characterized by a Cmax of free amine of about 100 ng/mL to about 500 ng/mL, after oral administration of from about 80 mg to about 125 mg of a compound of Formula (II) and release of promoiety A.

67. The pharmaceutical composition of embodiment 59 or 66, capable of providing an in vivo plasma level characterized by an AUC$_{(0-24)}$ of free amine of about 1000 h*ng/mL to about 6000 h*ng/mL, after oral administration of from about 80 mg to about 125 mg of a compound of Formula (II) and release of promoiety A.

68. The pharmaceutical composition of any one of embodiments 59 and 66-67, capable of providing an in vivo T$_{1/2}$ of free amine of about 5 h to about 15 h, after oral administration of from about 80 mg to about 125 mg of a compound of Formula (II) and release of promoiety A.

69. A compound of Formula (III):

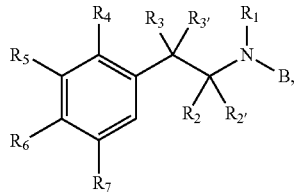

or a pharmaceutically acceptable salt thereof;
wherein,
R$_1$ is H or alkyl;
R$_2$ and R$_{2'}$ are each independently H, halogen, alkyl, —OH, or —O-alkyl, or R$_2$ and R$_{2'}$ together with the atom to which they are attached form a cycloalkyl ring;
R$_3$ and R$_{3'}$ are each independently hydrogen, alkyl, —OH, —O-alkyl, or —O-cycloalkyl, or
R$_3$ and R$_{3'}$ together with the atom to which they are attached form an oxo;
R$_4$, R$_5$, R$_6$ and R$_7$ are each independently hydrogen, halogen, —OH, —O-alkyl, —O-cycloalkyl, alkylene-OR$_8$, —SH, —S-alkyl, —S-cycloalkyl, or alkylene-SR$_8$, or R$_5$ and R$_6$ together with the atoms to which they are attached form a 5- to 8-membered heterocyclyl ring;
R$_8$ is H, alkyl, cycloalkyl, or alkylenecycloalkyl; and
B is

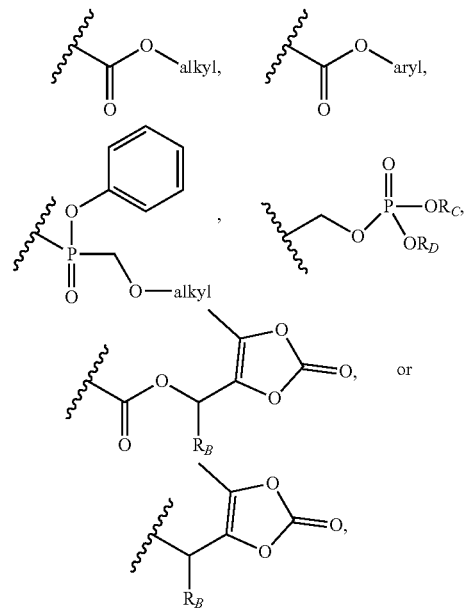

wherein R$_B$ is H or alkyl; and R$_C$ and R$_D$ are each independently H or alkyl.

69a. The compound of embodiment 69, having the structure:

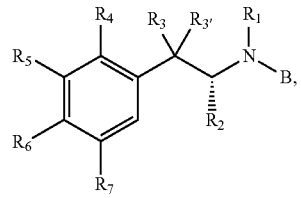

or a pharmaceutically acceptable salt thereof.

69b. The compound of embodiment 69, having the structure:

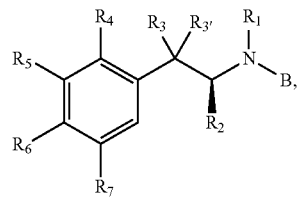

or a pharmaceutically acceptable salt thereof.

70. The compound of any one of embodiments 69-69b, wherein at least one of R$_4$, R$_5$, R$_6$ and R$_7$ is not H.
71. The compound of any one of embodiments 69-70, wherein R$_1$ is H or C$_1$-C$_6$ alkyl.
72. The compound of any one of embodiments 69-70, wherein R$_1$ is H.
73. The compound of any one of embodiments 69-70, wherein R$_1$ is CH$_3$.
74. The compound of any one of embodiments 69-73, wherein R$_2$ and R$_{2'}$ are each independently H, alkyl, or —OH.
75. The compound of any one of embodiments 69-73, wherein R$_2$ is alkyl and R$_{2'}$ is H.
76. The compound of any one of embodiments 69-73, wherein R$_2$ and R$_{2'}$ are each alkyl.
77. The compound of any one of embodiments 74-76, wherein the alkyl is methyl or isopropyl.
78. The compound of any one of embodiments 69-77, wherein R$_3$ and R$_{3'}$ are each independently H, —OH, or —O-alkyl or R$_3$ and R$_{3'}$ together with the atom to which they are attached form an oxo.
78a. The compound of any one of embodiments 69-77, wherein R$_3$ and R$_{3'}$ are each H.
79. The compound of any one of embodiments 69-78, wherein R$_4$ is H.
80. The compound of any one of embodiments 69-79, wherein R$_7$ is H.
81. The compound of any one of embodiments 69-80, wherein R$_5$ and R$_6$ are each independently halogen, —OH, —O-alkyl, —O-cycloalkyl, alkylene-OR$_8$, —SH, —S-alkyl, —S-cycloalkyl, or alkylene-SR$_8$.
82. The compound of any one of embodiments 69-80, wherein R$_5$ and R$_6$ together with the atoms to which they are attached form a 5- to 8-membered heterocyclyl ring.
83. The compound of any one of embodiments 69-82, wherein R$_8$ is alkyl.
84. The compound of any one of embodiments 69-83, wherein B is

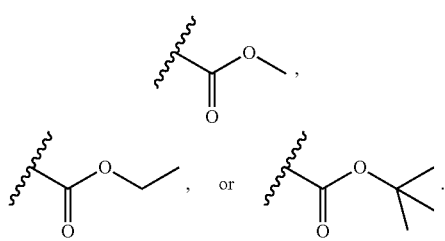

84a. The compound of any one of embodiments 69-83, wherein B is

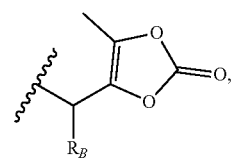

wherein $R_B$ is H or alkyl.

84b. The compound of any one of embodiments, 69-83, wherein B is

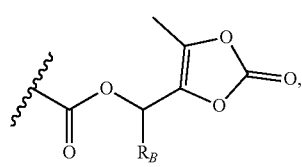

wherein $R_B$ is H or alkyl.

84c. The compound of embodiment 84a or 84b, wherein $R_B$ is H or Me.

84d. The compound of embodiment 84a or 84b, wherein $R_B$ is H.

84e. The compound of any one of embodiments 69-83, wherein B is

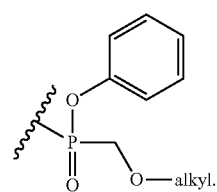

84f. The compound of embodiment 84e, wherein alkyl is methyl, ethyl, or isopropyl.

84g. The compound of embodiment 84e or 84f, wherein alkyl is methyl.

84h. The compound of any one of embodiments 69-83, wherein B is

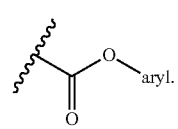

84i. The compound of embodiment 84h, wherein aryl is optionally substituted phenyl.

84j. The compound of embodiment 84h, wherein optionally substituted phenyl is

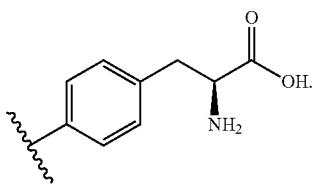 [SMILES: *c1ccc(C[C@H](N)C(=O)O)cc1]

84k. The compound of any one of embodiments 69-83, wherein B is

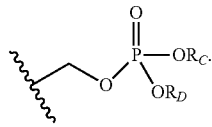

84l. The compound of embodiment 84k, wherein $R_C$ and $R_D$ are each independently H, Me, Et, or i-Pr.

84m. The compound of embodiment 84k or 84l, wherein $R_C$ and $R_D$ are each H.

85. The compound of any one of embodiments 69-80 and 82-84m, having the structure of Formula (IIIb):

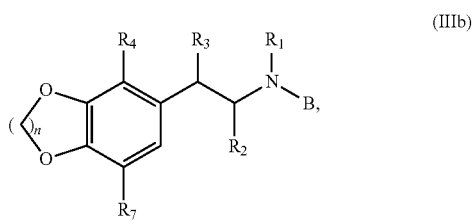

wherein n is 1 or 2.

85a. The compound of embodiment 85, having the structure:

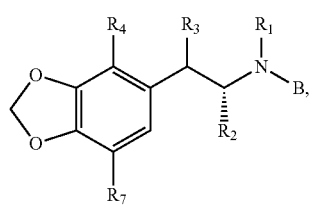

or a pharmaceutically acceptable salt thereof.

85b. The compound of embodiment 85, having the structure:

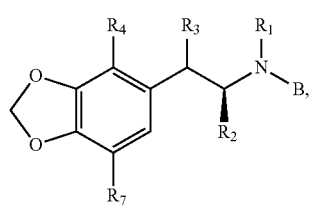

or a pharmaceutically acceptable salt thereof.

85c. The compound of any one of embodiments 85-85b, wherein R₃ is H.

85d. The compound of any one of embodiments 69-83 and 84a-85, having the structure:

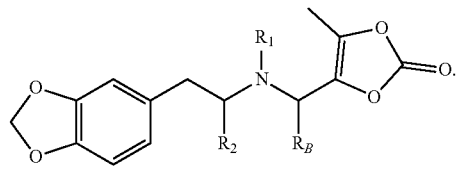

85e. The compound of any one of embodiments 69-83 and 84a-85, having the structure:

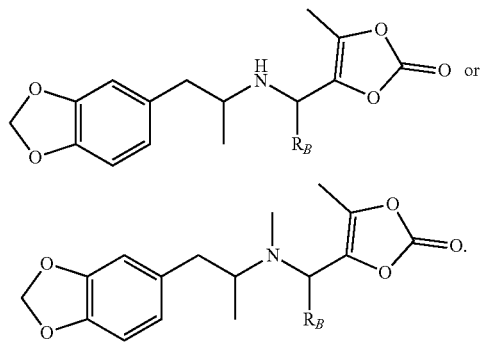

85f. The compound of any one of embodiments 69-83 and 84a-85, having the structure:

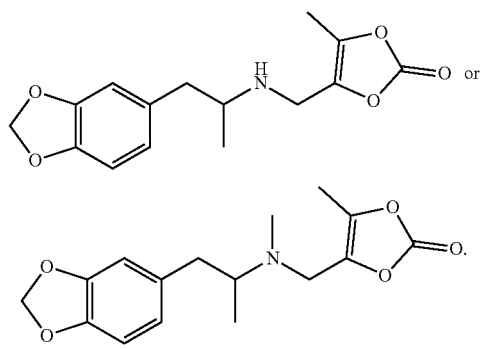

85g. The compound of any one of embodiments 69-83 and 84a-85c, having the structure:

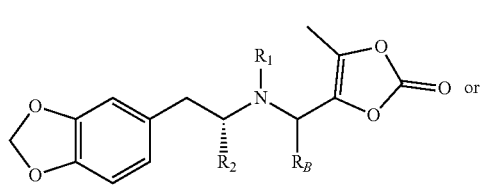

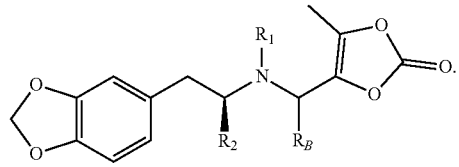

85h. The compound of embodiment 85g having the structure:

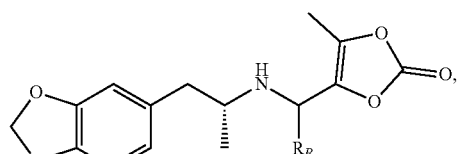

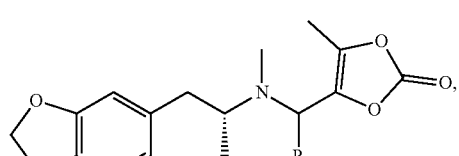

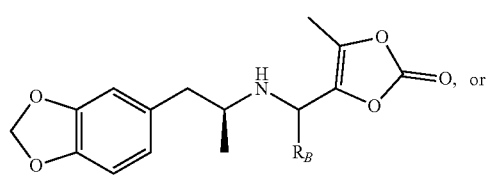

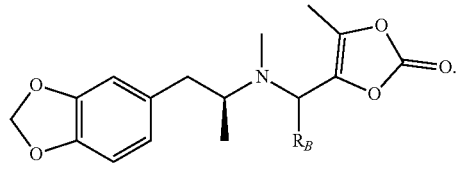

85i. The compound of embodiment 85g or 85h having the structure:

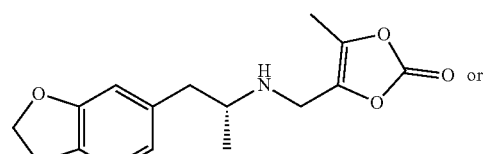

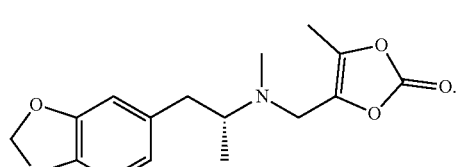

85j. The compound of embodiment 85h or 85i, having the structure:

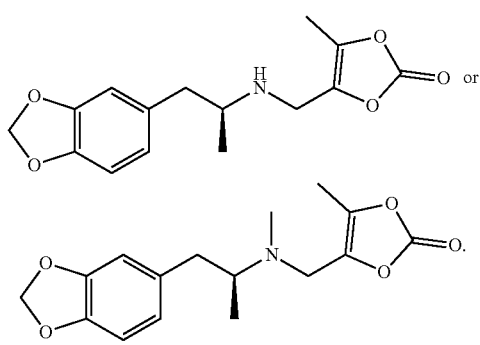

86. A pharmaceutical composition comprising a compound of any one of embodiments 69-85j and a pharmaceutically acceptable excipient.
87. The pharmaceutical composition of embodiment 86, capable of providing an in vivo plasma level characterized by a Cmax of free amine of about 100 ng/mL to about 500 ng/mL, after oral administration of from about 80 mg to about 125 mg of a compound of Formula (III) and release of promoiety B.
88. The pharmaceutical composition of embodiment 86 or 87, capable of providing an in vivo plasma level characterized by an $AUC_{(0-24)}$ of free amine of about 1000 h*ng/mL to about 6000 h*ng/mL, after oral administration of from about 80 mg to about 125 mg of a compound of Formula (III) and release of promoiety B.
89. The pharmaceutical composition of any one of embodiments 86-88, capable of providing an in vivo $T_{1/2}$ of free amine of about 5 h to about 15 h, after oral administration of from about 80 mg to about 125 mg of a compound of Formula (III) and release of promoiety B.
90. A method of treating post-traumatic stress disorder (PTSD) in a subject in need thereof, comprising administering to the subject a therapeutically effective amount of a composition of any one of embodiments 24-33, 59-68, and 86-89.
91. A method of treating an eating disorder in a subject in need thereof, comprising administering to the subject a therapeutically effective amount of a composition of any one of embodiments 24-33, 59-68, and 86-89.
92. A method of treating depression in a subject in need thereof, comprising administering to the subject a therapeutically effective amount of a composition of any one of embodiments 24-33, 59-68, and 86-89.
93. The method of embodiment 92, wherein the depression is major depressive disorder (MDD) or treatment-resistant depression (TRD).
94. A method of treating an anxiety disorder in a subject in need thereof, comprising administering to the subject a therapeutically effective amount of a composition of any one of embodiments 24-33, 59-68, and 86-89.
95. The method of embodiment 94, wherein the anxiety disorder is generalized anxiety disorder.
96. A compound selected from compounds 1-11 of Table 6.
97. A compound selected from compounds 1-45 of Table 1.

EXAMPLES

Example 1. Preparation of Prodrug Compounds of the Present Disclosure

Compounds of the present disclosure are prepared from MDA, MDMA or derivative thereof in a one or two-step synthetic route that relies on standard amide and ester bond-forming reactions between commercially available reagents.

Specific enantiomers (or diastereomers in some cases) are obtained by separation of the mixtures and identification of the desired isomer.

General reaction conditions are provided, and reaction products can be purified by known methods including silica gel chromatography using various organic solvents such as hexane, dichloromethane, ethyl acetate, methanol and the like or preparative reverse phase high pressure liquid chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 44th. Ed., Wiley & Sons, 2006, as well as in Jerry March, *Advanced Organic Chemistry*, 4th edition, John Wiley & Sons, publisher, New York, 1992 which are incorporated herein by reference in their entirety.

Example 2. PK Measurements in Healthy Human Subjects Administered MDMA

| Dose | 75 mg MDMA | 125 mg MDMA |
|---|---|---|
| $C_{max}$ (ng/mL) | 130.9 | 236.4 |
| $AUC_{0-24}$ (ng/ml * h$^{-1}$) | 1331 | 2623 |
| $T_{max}$ (h) | 1.8 | 2.4 |
| $T_{1/2}$ (h) | 7.7 | 8.6 |

Example 3. PK Measurements in Healthy Human Subjects Administered MDA

| Dose | 75 mg MDA | 125 mg MDA |
|---|---|---|
| $C_{max}$ (ng/mL) | 7.8 | 13.7 |
| $AUC_{0-24}$ (ng/ml * h$^{-1}$) | 122 | 215 |
| $T_{max}$ (h) | 5 | 7 |

Prodrugs have been exemplified in the following classes:
1. Enacarbil (N-acyloxyalkoxy Carbonyl) Derivatives

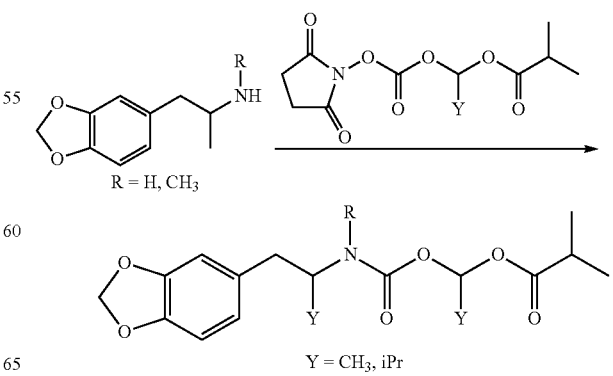

2. Simple Amino Acids

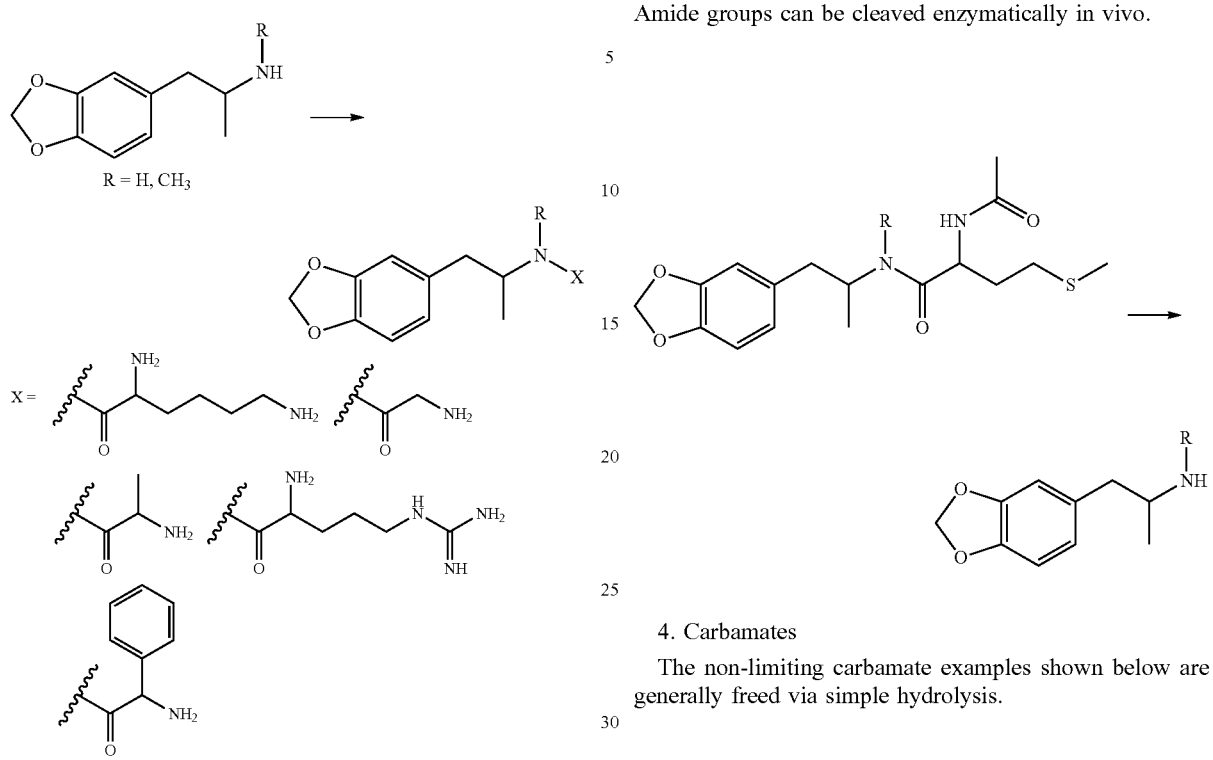

In some embodiments, amino acids provide a group that can be internally released to provide the MDMA, MDA, or a derivative thereof. A specific example of an internally released protecting group utilizes ornithine. prodrug can be stabilized to prevent cyclization and release by dosing a salt of the amine or by utilizing a slow release of a secondary protecting group such as a carbamate. The α-amino group is an optional substituent.

3. Amides/Amino Acid Variants

Below is a pro-drug amide derived from docarpamine. Amide groups can be cleaved enzymatically in vivo.

4. Carbamates

The non-limiting carbamate examples shown below are generally freed via simple hydrolysis.

5. Dialkyl-1,3-dioxol-2-one

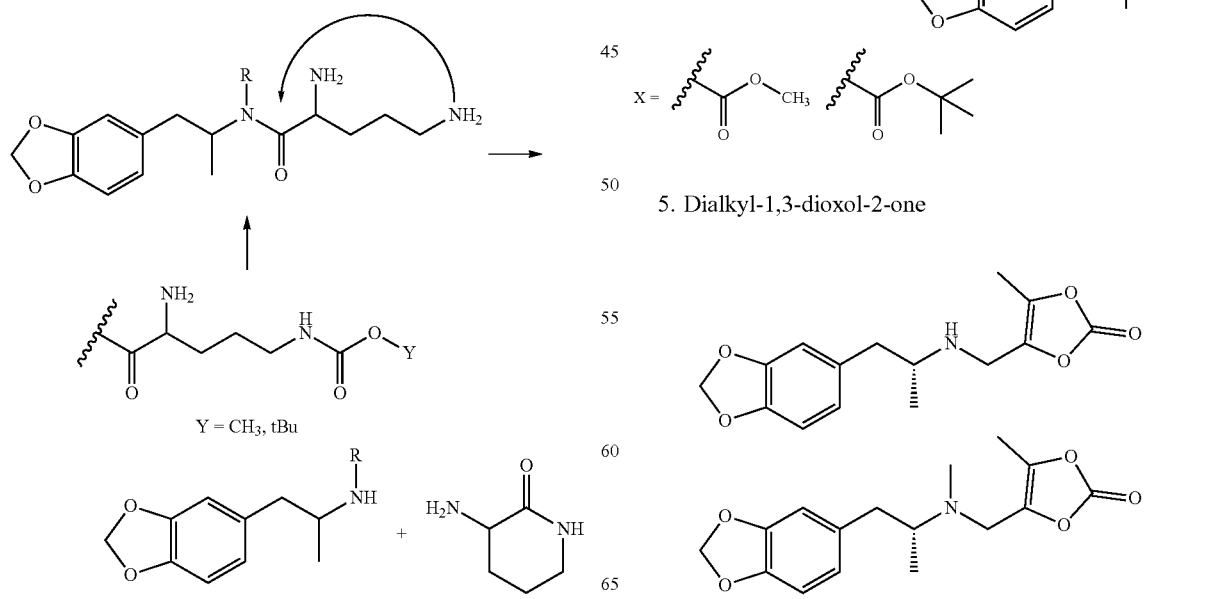

6. Methoxymethyl Phosphinyl Amide (Kirby and Dowd, 2022)

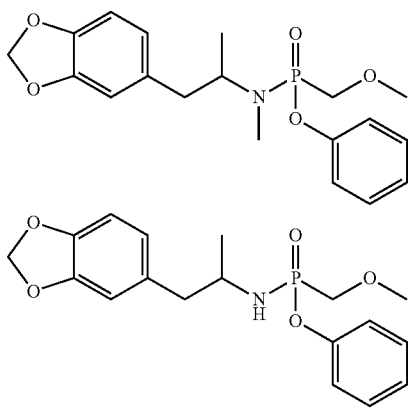

Syntheses of the prodrugs may be accomplished from MDA or MDMA and commercially available reagents in one or two steps. Isolation of specific enantiomers can be achieved by separation of the mixtures or by enantioselective synthesis methods.

7. Methoxymethyl Phosphate

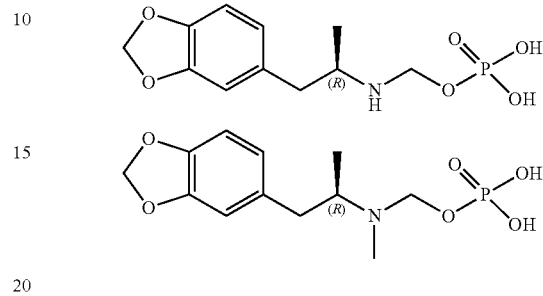

TABLE 1

Compounds of the invention

| ID | Structure | Chemical name |
|---|---|---|
| 1 | 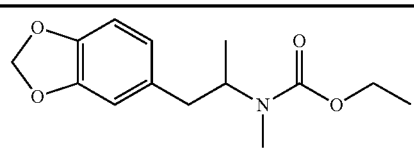 | ethyl(1-(benzo[d][1,3]dioxol-5-yl)propan-2-yl)(methyl)carbamate |
| 2 | 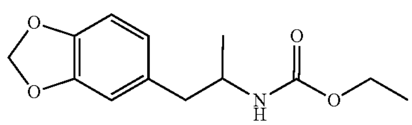 [SMILES: CCOC(=O)NC(C)Cc1ccc2c(c1)OCO2] | ethyl(1-(benzo[d][1,3]dioxol-5-yl)propan-2-yl)carbamate |
| 3 | 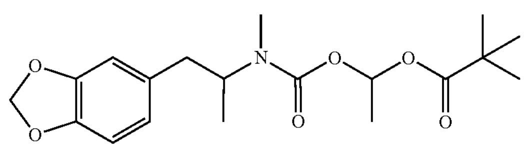 [SMILES: CC(OC(=O)N(C)C(C)Cc1ccc2c(c1)OCO2)OC(=O)C(C)(C)C] | 1-(((1-(benzo[d][1,3]dioxol-5-yl)propan-2-yl)(methyl)carbamoyl)oxy)ethyl pivalate |
| 4 | 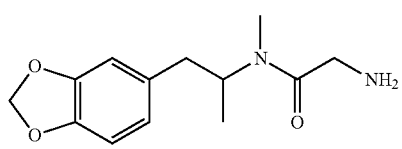 [SMILES: CC(Cc1ccc2c(c1)OCO2)N(C)C(=O)CN] | 2-amino-N-(1-(benzo[d][1,3]dioxol-5-yl)propan-2-yl)-N-methylacetamide |
| 5 | 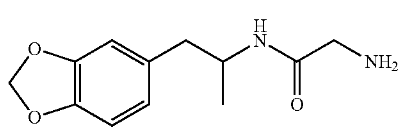 [SMILES: CC(Cc1ccc2c(c1)OCO2)NC(=O)CN] | 2-amino-N-(1-(benzo[d][1,3]dioxol-5-yl)propan-2-yl)acetamide |
| 6 | 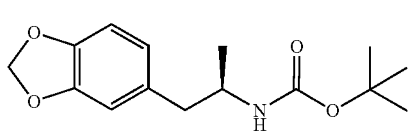 [SMILES: C[C@H](Cc1ccc2c(c1)OCO2)NC(=O)OC(C)(C)C] | tert-butyl(R)-(1-(benzo[d][1,3]dioxol-5-yl)propan-2-yl)carbamate |
| 7 | 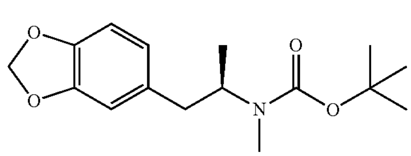 [SMILES: C[C@H](Cc1ccc2c(c1)OCO2)N(C)C(=O)OC(C)(C)C] | tert-butyl(R)-(1-(benzo[d][1,3]dioxol-5-yl)propan-2-yl)(methyl)carbamate |

TABLE 1-continued

Compounds of the invention

| ID | Structure | Chemical name |
|---|---|---|
| 8 | 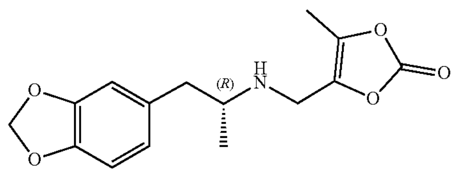 | (R)-4-(((1-(benzo[d][1,3]dioxol-5-yl)propan-2-yl)amino)methyl)-5-methyl-1,3-dioxol-2-one |
| 9 | 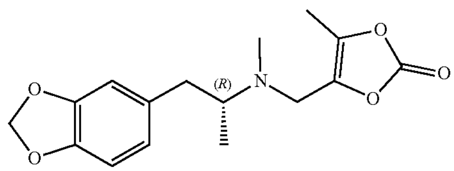 | (R)-4-(((1-(benzo[d][1,3]dioxol-5-yl)propan-2-yl)(methyl)amino)methyl)-5-methyl-1,3-dioxol-2-one |
| 10 | 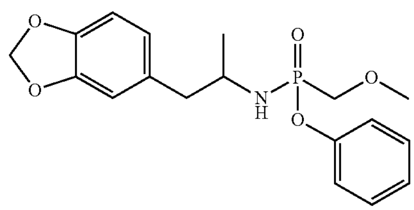 [SMILES: COCP(=O)(NC(C)Cc1ccc2c(c1)OCO2)Oc1ccccc1] | phenyl N-(1-(benzo[d][1,3]dioxol-5-yl)propan-2-yl)-P-(methoxymethyl)phosphonamidate |
| 11 | 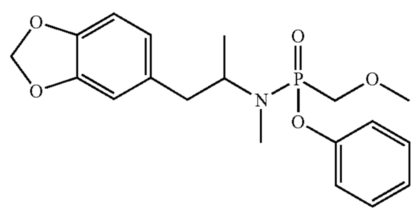 [SMILES: COCP(=O)(Oc1ccccc1)N(C)C(C)Cc1ccc2c(c1)OCO2] | phenyl N-(1-(benzo[d][1,3]dioxol-5-yl)propan-2-yl)-P-(methoxymethyl)-N-methylphosphonamidate |
| 12 | 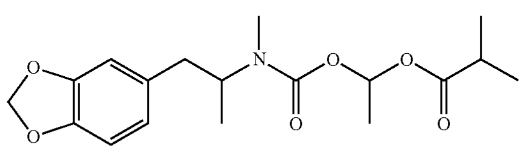 [SMILES: CC(OC(=O)C(C)C)OC(=O)N(C)C(C)Cc1ccc2c(c1)OCO2] | 1-(((1-(benzo[d][1,3]dioxol-5-yl)propan-2-yl)(methyl)carbamoyl)oxy)ethyl isobutyrate |
| 13 | 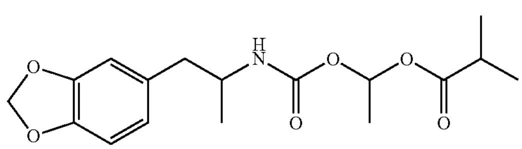 [SMILES: CC(Cc1ccc2c(c1)OCO2)NC(=O)OC(C)OC(=O)C(C)C] | 1-(((1-(benzo[d][1,3]dioxol-5-yl)propan-2-yl)carbamoyl)oxy)ethyl isobutyrate |
| 14 | 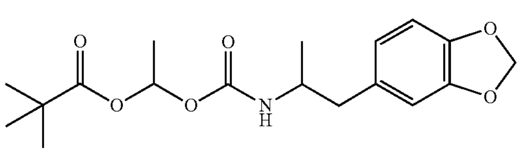 [SMILES: CC(Cc1ccc2c(c1)OCO2)NC(=O)OC(C)OC(=O)C(C)(C)C] | 1-(((1-(benzo[d][1,3]dioxol-5-yl)propan-2-yl)carbamoyl)oxy)ethyl pivalate |
| 15 | 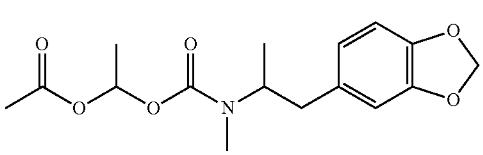 [SMILES: CC(=O)OC(C)OC(=O)N(C)C(C)Cc1ccc2c(c1)OCO2] | 1-(((1-(benzo[d][1,3]dioxol-5-yl)propan-2-yl)(methyl)carbamoyl)oxy)ethyl acetate |
| 16 | 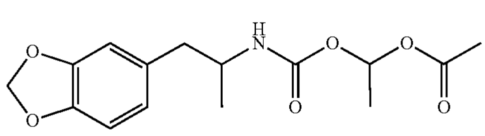 [SMILES: CC(=O)OC(C)OC(=O)NC(C)Cc1ccc2c(c1)OCO2] | 1-(((1-(benzo[d][1,3]dioxol-5-yl)propan-2-yl)carbamoyl)oxy)ethyl acetate |

TABLE 1-continued

Compounds of the invention

| ID | Structure | Chemical name |
|---|---|---|
| 17 | 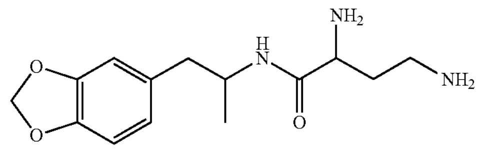 [SMILES: CC(Cc1ccc2c(c1)OCO2)NC(=O)C(N)CCN] | 2,4-diamino-N-(1-(benzo[d][1,3]dioxol-5-yl)propan-2-yl)butanamide |
| 18 | 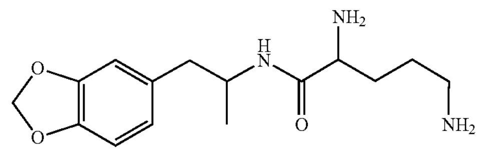 [SMILES: CC(Cc1ccc2c(c1)OCO2)NC(=O)C(N)CCCN] | 2,5-diamino-N-(1-(benzo[d][1,3]dioxol-5-yl)propan-2-yl)pentanamide |
| 19 | 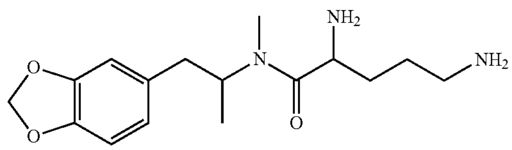 [SMILES: CC(Cc1ccc2c(c1)OCO2)N(C)C(=O)C(N)CCCN] | 2,5-diamino-N-(1-(benzo[d][1,3]dioxol-5-yl)propan-2-yl)-N-methylpentanamide |
| 21 | 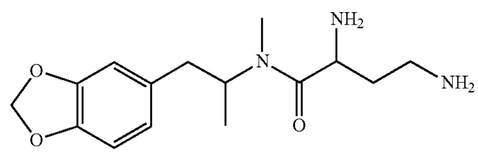 [SMILES: CC(Cc1ccc2c(c1)OCO2)N(C)C(=O)C(N)CCN] | 2,4-diamino-N-(1-(benzo[d][1,3]dioxol-5-yl)propan-2-yl)-N-methylbutanamide |
| 22 | 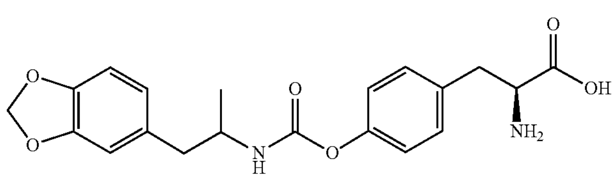 [SMILES: CC(Cc1ccc2c(c1)OCO2)NC(=O)Oc1ccc(C[C@H](N)C(=O)O)cc1] | (2S)-2-amino-3-(4-(((1-(benzo[d][1,3]dioxol-5-yl)propan-2-yl)carbamoyl)oxy)phenyl)propanoic acid |
| 23 | 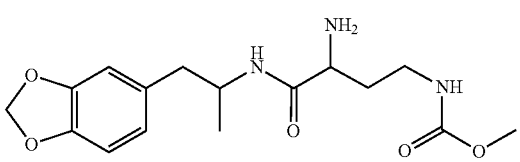 [SMILES: COC(=O)NCCC(N)C(=O)NC(C)Cc1ccc2c(c1)OCO2] | methyl(3-amino-4-((1-(benzo[d][1,3]dioxol-5-yl)propan-2-yl)amino)-4-oxobutyl)carbamate |
| 25 | 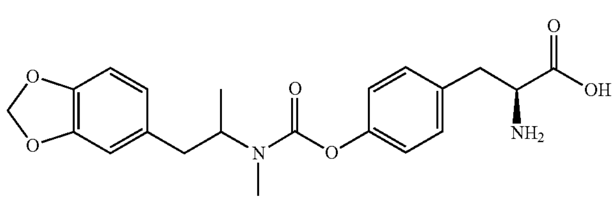 [SMILES: CC(Cc1ccc2c(c1)OCO2)N(C)C(=O)Oc1ccc(C[C@H](N)C(=O)O)cc1] | (2S)-2-amino-3-(4-(((1-(benzo[d][1,3]dioxol-5-yl)propan-2-yl)(methyl)carbamoyl)oxy)phenyl)propanoic acid |
| 26 | 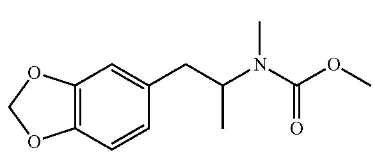 [SMILES: COC(=O)N(C)C(C)Cc1ccc2c(c1)OCO2] | methyl(1-(benzo[d][1,3]dioxol-5-yl)propan-2-yl)(methyl)carbamate |
| 29 | 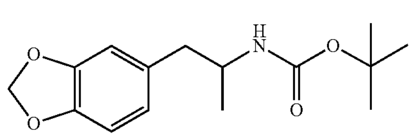 [SMILES: CC(Cc1ccc2c(c1)OCO2)NC(=O)OC(C)(C)C] | tert-butyl(1-(benzo[d][1,3]dioxol-5-yl)propan-2-yl)carbamate |

TABLE 1-continued

Compounds of the invention

| ID | Structure | Chemical name |
|---|---|---|
| 30 | 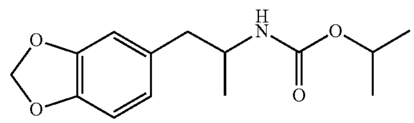 [SMILES: CC(Cc1ccc2c(c1)OCO2)NC(=O)OC(C)C] | isopropyl(1-(benzo[d][1,3]dioxol-5-yl)propan-2-yl)carbamate |
| 31 | 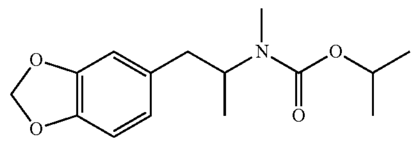 [SMILES: CC(C)OC(=O)N(C)C(C)Cc1ccc2c(c1)OCO2] | isopropyl(1-(benzo[d][1,3]dioxol-5-yl)propan-2-yl)(methyl)carbamate |
| 32 | 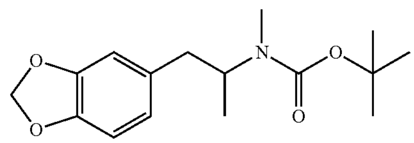 [SMILES: CC(Cc1ccc2c(c1)OCO2)N(C)C(=O)OC(C)(C)C] | tert-butyl(1-(benzo[d][1,3]dioxol-5-yl)propan-2-yl)(methyl)carbamate |
| 34 | 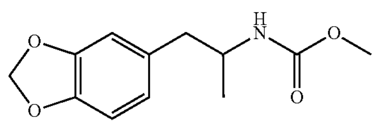 [SMILES: COC(=O)NC(C)Cc1ccc2c(c1)OCO2] | methyl(1-(benzo[d][1,3]dioxol-5-yl)propan-2-yl)carbamate |
| 35 | 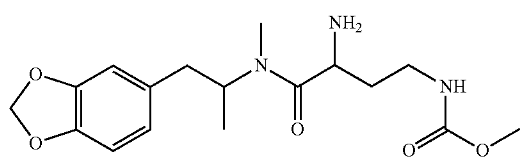 [SMILES: COC(=O)NCCC(N)C(=O)N(C)C(C)Cc1ccc2c(c1)OCO2] | methyl(3-amino-4-((1-(benzo[d][1,3]dioxol-5-yl)propan-2-yl)(methyl)amino)-4-oxobutyl)carbamate |
| 36 | 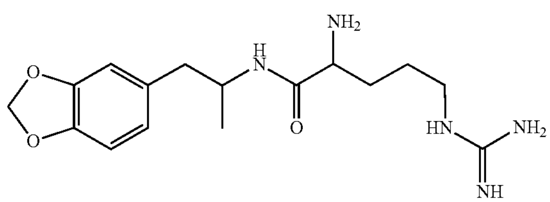 [SMILES: CC(Cc1ccc2c(c1)OCO2)NC(=O)C(N)CCCNC(=N)N] | 2-amino-N-(1-(benzo[d][1,3]dioxol-5-yl)propan-2-yl)-5-guanidinopentanamide |
| 37 | 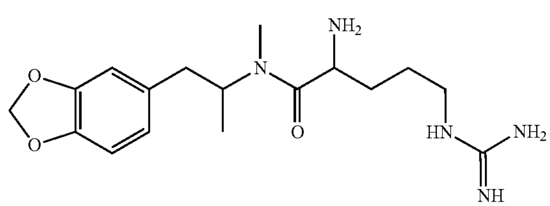 [SMILES: CC(Cc1ccc2c(c1)OCO2)N(C)C(=O)C(N)CCCNC(=N)N] | 2-amino-N-(1-(benzo[d][1,3]dioxol-5-yl)propan-2-yl)-5-guanidino-N-methylpentanamide |
| 38 | 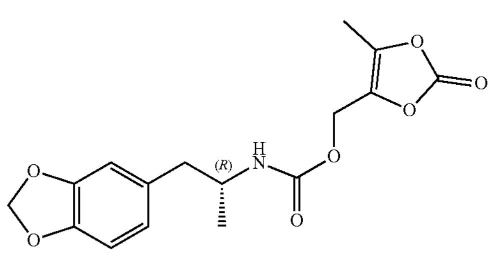 | (5-methyl-2-oxo-1,3-dioxol-4-yl)methyl (R)-(1-(benzo[d][1,3]dioxol-5-yl)propan-2-yl)carbamate |

TABLE 1-continued

Compounds of the invention

| ID | Structure | Chemical name |
| --- | --- | --- |
| 39 | 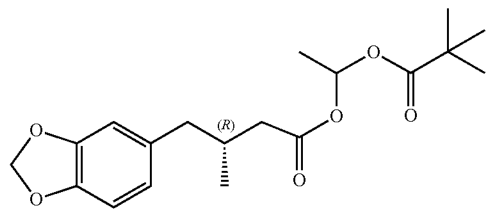 | 1-((((R)-1-(benzo[d][1,3]dioxol-5-yl)propan-2-yl)(methyl)carbamoyl)oxy)ethyl pivalate |
| 40 | 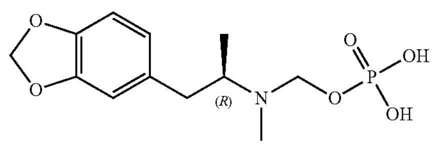 | 1-(benzo[d][1,3]dioxol-5-yl)propan-2-yl)(methyl)amino)methyl dihydrogen phosphate |
| 41 | 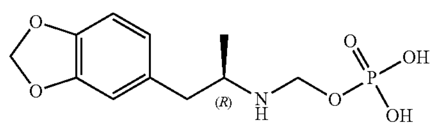 | (R)-((1-(benzo[d][1,3]dioxol-5-yl)propan-2-yl)amino)methyl dihydrogen phosphate |
| 42 | 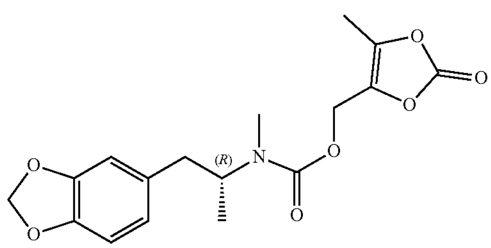 | (5-methyl-2-oxo-1,3-dioxol-4-yl)methyl(R)-(1-(benzo[d][1,3]dioxol-5-yl)propan-2-yl)(methyl)carbamate |
| 43 | 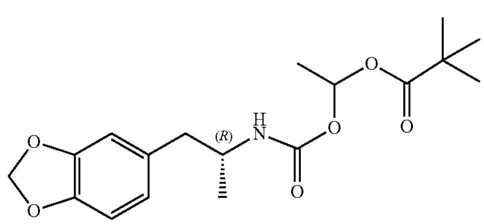 | 1-((((R)-1-(benzo[d][1,3]dioxol-5-yl)propan-2-yl)carbamoyl)oxy)ethyl pivalate |
| 44 | 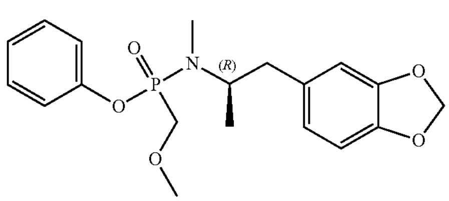 | phenyl N-((R)-1-(benzo[d][1,3]dioxol-5-yl)propan-2-yl)-P-(methoxymethyl)-N-methylphosphonamidate |
| 45 | 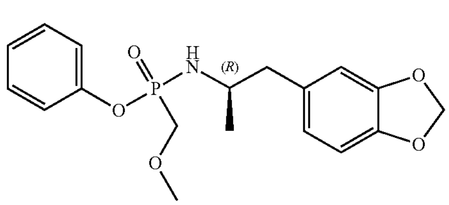 | phenyl N-((R)-1-(benzo[d][1,3]dioxol-5-yl)propan-2-yl)-P-(methoxymethyl)phosphonamidate |

Example 4: Synthesis of Compounds

Synthesis of Prodrug 1.0: Ethyl (1-(benzo[d][1,3]dioxol-5-yl)propan-2-yl)(methyl)carbamate Compound 1.0 was synthesized from commercially available compound 1A in six steps (Scheme 1).

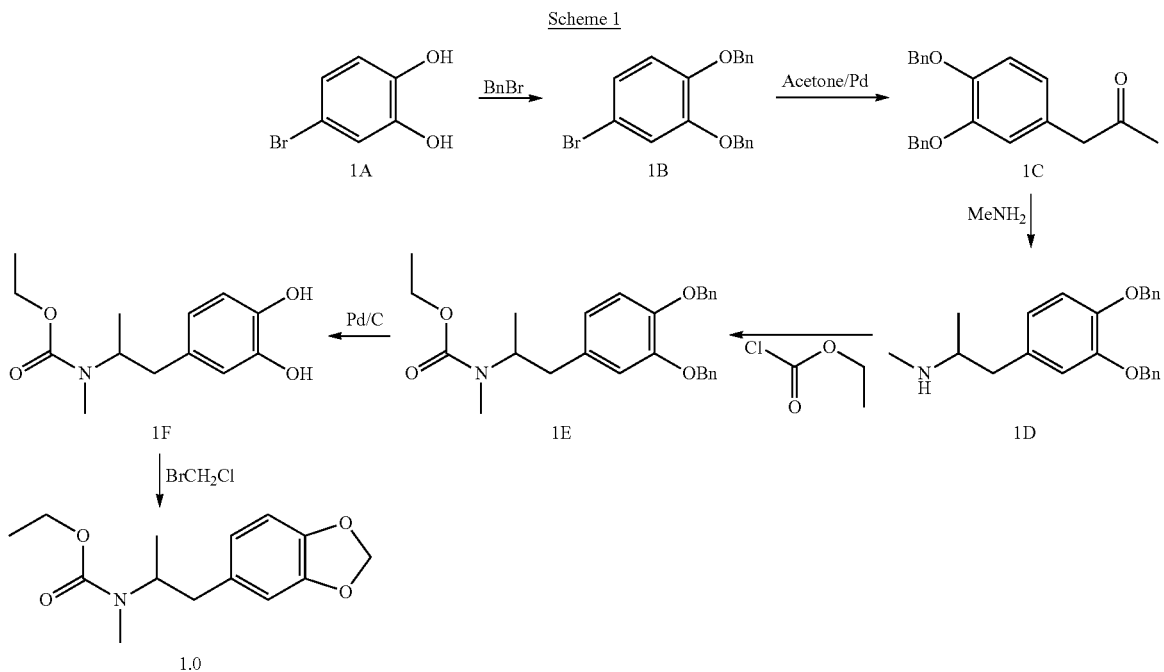

Scheme 1

Synthesis of 1A

To a stirred solution of 4-bromocatechol (5.0 g, 26.45 mmol, 1.0 equiv) and potassium carbonate (7.3 g, 52.91 mmol, 2.0 equiv) in acetone (50.0 mL) was added (bromomethyl)benzene (6.8 g, 39.68 mmol, 1.5 equiv) dropwise at 25° C. under nitrogen atmosphere. The mixture was stirred for 16h at 60° C. Added 100 mL of water to the reaction, the aqueous layer was extracted with ethyl acetate (3×300 mL). The organic phase was dried over anhydrous sodium sulfate, filtered and concentrated under reduced pressure. The residue was purified by reversed-phase flash chromatography with the following conditions: column, C18 silica gel; mobile phase, acetonitrile in Water (0.05% $NH_4HCO_3$), 10% to 100% gradient in 20 min; detector, UV 254 nm. This resulted in 1A (5.0 g, 51%) as a white solid. MS m/z $[M+H]^+$ (ESI): 369.04.

Synthesis of 1B

To a stirred solution of 1A (1.0 g, 2.71 mmol, 1.0 equiv) and $K_3PO_4$ (1.7 g, 8.12 mmol, 3.0 equiv) in acetone (10.0 mL) was added XPhos Pd(crotyl)Cl (182.5 mg, 0.27 mmol, 0.1 equiv) at 25° C. under nitrogen atmosphere. The mixture was stirred for 6h at 50° C. The reaction was diluted with 50 mL of dichloromethane, washed with 2×20 mL saturated aqueous sodium chloride solution, dried over anhydrous sodium sulfate, filtered and concentrated under reduced pressure. The residue was purified by reversed-phase flash chromatography with the following conditions: column, C18 silica gel; mobile phase, acetonitrile in Water (0.05% $NH_4HCO_3$), 10% to 100% gradient in 20 min; detector, UV 254 nm. This resulted in 1B (480.0 mg, 51%) as a white solid. MS m/z $[M+H]^+$ (ESI): 347.16.

Synthesis of 1C

To a solution of methanamine hydrochloride (935.5 mg, 13.86 mmol, 10.0 equiv) in methyl alcohol (5.0 mL) was added sodium cyanoborohydride (435.4 mg, 6.93 mmol, 5.0 equiv) and 1B (480.0 mg, 1.39 mmol, 1.0 equiv) at 0° C. The resulting mixture was stirred for 16h at room temperature. The reaction was diluted with 50 mL of dichloromethane, washed with 2×20 mL saturated aqueous sodium chloride solution, dried over anhydrous sodium sulfate, filtered and concentrated under reduced pressure. The residue was purified by reversed-phase flash chromatography with the following conditions: column, C18 silica gel; mobile phase, acetonitrile in Water (0.1% TFA), 10% to 100% gradient in 20 min; detector, UV 254 nm. to afford 1C (450.0 mg, 90%) as a white solid. MS m/z $[M+H]^+$ (ESI): 362.20.

Synthesis of 1D

To a stirred solution of 1C (450.0 mg, 1.25 mmol, 1.0 equiv) and triethylamine (377.9 mg, 3.74 mmol, 3.0 equiv) in dichloromethane (5.0 mL) was added ethyl chloroformate (270.2 mg, 2.49 mmol, 2.0 equiv) dropwise at 0° C. under nitrogen atmosphere. The resulting mixture was stirred for 2 h at room temperature. The reaction was diluted with 50 mL of dichloromethane, washed with 2×20 mL saturated aqueous sodium chloride solution, dried over anhydrous sodium sulfate, filtered and concentrated under reduced pressure. The residue was purified by reversed-phase flash chromatography with the following conditions: column, C18 silica gel; mobile phase, acetonitrile in Water (0.05% $NH_4HCO_3$), 10% to 100% gradient in 20 min; detector, UV 254 nm. 300 mg of 1D was obtained as a colorless oil. MS m/z $[M+H]+$ (ESI): 434.23.

Synthesis of 1E and Final Product 1.0

A mixture of 1D (300.0 mg, 0.69 mmol, 1.0 equiv) and 10% Pd/C (60.0 mg) in tetrahydrofuran (1.0 mL) was stirred for 3 h at room temperature under hydrogen atmosphere. The solid was filtered and washed with tetrahydrofuran. The filtrate was concentrated under reduced pressure. The crude product 1E was used in the next step directly without further purification. To a stirred solution of 1E (100.0 mg, 0.40 mmol, 1.0 equiv) and cesium carbonate (231.5 mg, 0.71 mmol, 1.8 equiv) in DMF (1.0 mL) was added bromo(chloro)methane (91.9 mg, 0.71 mmol, 1.8 equiv) dropwise at 0° C. under nitrogen atmosphere. The resulting mixture was stirred for 2 h at room temperature. The reaction was diluted with 50 mL of dichloromethane, washed with 2×20 mL saturated aqueous sodium chloride solution, dried over anhydrous sodium sulfate, filtered, and concentrated under reduced pressure. The residue was purified by reversed-phase flash chromatography with the following conditions: column, C18 silica gel; mobile phase, acetonitrile in Water (0.05% NH$_4$HCO$_3$), 10% to 100% gradient in 20 min; detector, UV 254 nm. 28.9 mg (27%) of 1.0, Ethyl (1-(benzo[d][1,3]dioxol-5-yl)propan-2-yl)(methyl)carbamate was obtained as a colorless oil.

MS m/z [M+H]+ (ESI): 266.10. $^1$H NMR (300 MHz, DMSO-d6) δ 6.81-6.60 (m, 3H), 5.95 (s, 2H), 4.31-4.25 (m, 1H), 3.96-3.81 (m, 2H), 2.64-2.59 (m, 5H), 1.08-0.99 (m, 6H).

Synthesis of Prodrug 2.0: Ethyl (1-(benzo[d][1,3]dioxol-5-yl)propan-2-yl)carbamate Prodrug 2.0 was synthesized from the previous intermediate 1C in 4 steps (Scheme 2).

romethane was added ethyl chloroformate (93.7 mg, 0.86 mmol, 1.0 equiv) dropwise at 0° C. under nitrogen atmosphere. The mixture was stirred at 25° C. for 16h. The reaction was diluted with 50 mL of dichloromethane, washed with 2×20 mL saturated aqueous sodium chloride solution, dried over anhydrous sodium sulfate, filtered and concentrated under reduced pressure. The residue was purified by reversed-phase flash chromatography with the following conditions: column, C18 silica gel; mobile phase, acetonitrile in water (0.10% NH$_3$·H$_2$O), 10% to 100% gradient in 20 min; detector, UV 254 nm. This resulted in 2B (160 mg, 44%) as a yellow solid. MS m/z [M+H]$^+$ (ESI): 420.21.

Synthesis of 2C and Final Product 2.0

A mixture of 2B (150.0 mg, 0.36 mmol, 1.0 equiv) and 10% Pd/C (30.0 mg) in tetrahydrofuran (5.0 mL) was stirred for 3 h at room temperature under hydrogen atmosphere. The solid was filtered and washed with tetrahydrofuran. The filtrate was concentrated under reduced pressure to crude material 2C. The crude product (2C) was used in the next step directly without further purification.

To a solution of 2C (100.0 mg, 0.42 mmol, 1.0 equiv) and cesium carbonate (217.8 mg, 0.67 mmol, 1.6 equiv) in N,N-Dimethylformamide was added bromo(chloro)methane

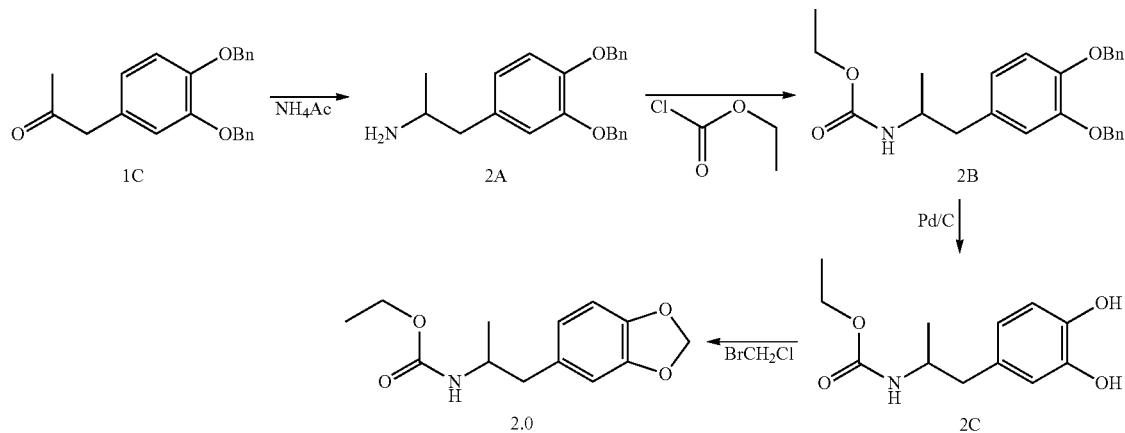

Scheme 2

Synthesis of 2A

To a solution of NH$_4$OAc (2.22g, 28.83 mmol, 10.0 equiv.) in methyl alcohol (10.0 mL) was added sodium cyanoborohydride (0.91g, 14.44 mmol, 5.0 equiv.), 1C (1 g, 2.89 mmol, 1.0 equiv.) and AcOH (1 mL) at 0° C. The resulting mixture was stirred for 16h at room temperature. The reaction was diluted with 100 mL of dichloromethane, washed with 2×50 mL saturated aqueous sodium chloride solution, dried over anhydrous sodium sulfate, filtered, and concentrated under reduced pressure. The residue was purified by reversed-phase flash chromatography with the following conditions: column, C18 silica gel; mobile phase, acetonitrile in Water (0.1% TFA), 10% to 100% gradient in 20 min; detector, UV 254 nm. to afford 2A (840 mg, 84%) as a white solid.

Synthesis of 2B

To a solution of 2A (300.0 mg, 0.86 mmol, 1.0 equiv) and triethylamine (262.1 mg, 2.58 mmol, 3.0 equiv) in dichlo- (86.5 mg, 0.67 mmol, 1.6 equiv) dropwise at 0° C. under nitrogen atmosphere. The resulting mixture was stirred for 2h at room temperature under nitrogen atmosphere. The reaction was diluted with 50 mL of dichloromethane, washed with 2×20 mL saturated aqueous sodium chloride solution, dried over anhydrous sodium sulfate, filtered, and concentrated under reduced pressure. The crude product was purified by Prep-HPLC with the following conditions (Column: XBridge Shield RP18 OBD Column, 30*150 mm, 5 μm; Mobile Phase A: Water (0.1% TFA), Mobile Phase B: ACN; Flow rate: 60 mL/min; Gradient: 27% B to 55% B in 9 min, 55% B; Wavelength: 254 nm) to afford Prodrug 2.0, ethyl (1-(benzo[d][1,3]dioxol-5-yl)propan-2-yl)carbamate (18 mg) as a colorless oil. MS m/z [M+H]$^+$ (ESI): 252.05. $^1$H NMR (300 MHz, Methanol-d$_4$) δ 6.72-6.62 (m, 3H), 5.88 (s, 2H), 4.04-3.97 (m, 2H), 3.81-3.70 (m, 1H), 2.73-2.52 (m, 2H), 1.21-1.07 (m, 6H).

Synthesis of Prodrug 3.0: 1-(((1-(benzo[d][1,3]di-oxol-5-yl)propan-2-yl)(methyl)carbamoyl)oxy)ethyl pivalate Compound 3.0 was synthesized from previously synthesized intermediate 1D (scheme 1) in four steps (Scheme 3).

gel; mobile phase, acetonitrile in water (0.10% NH$_3$·H$_2$O), 10% to 100% gradient in 20 min; detector, UV 254 nm. This resulted in 3D (114.0 mg, 66%) as a yellow oil. MS m/z [M+H]$^+$ (ESI): 534.28.

A mixture of 3D (150.0 mg, 0.28 mmol, 1.0 equiv) and 10% Pd/C (40.0 mg) in tetrahydrofuran (1.0 mL) was stirred

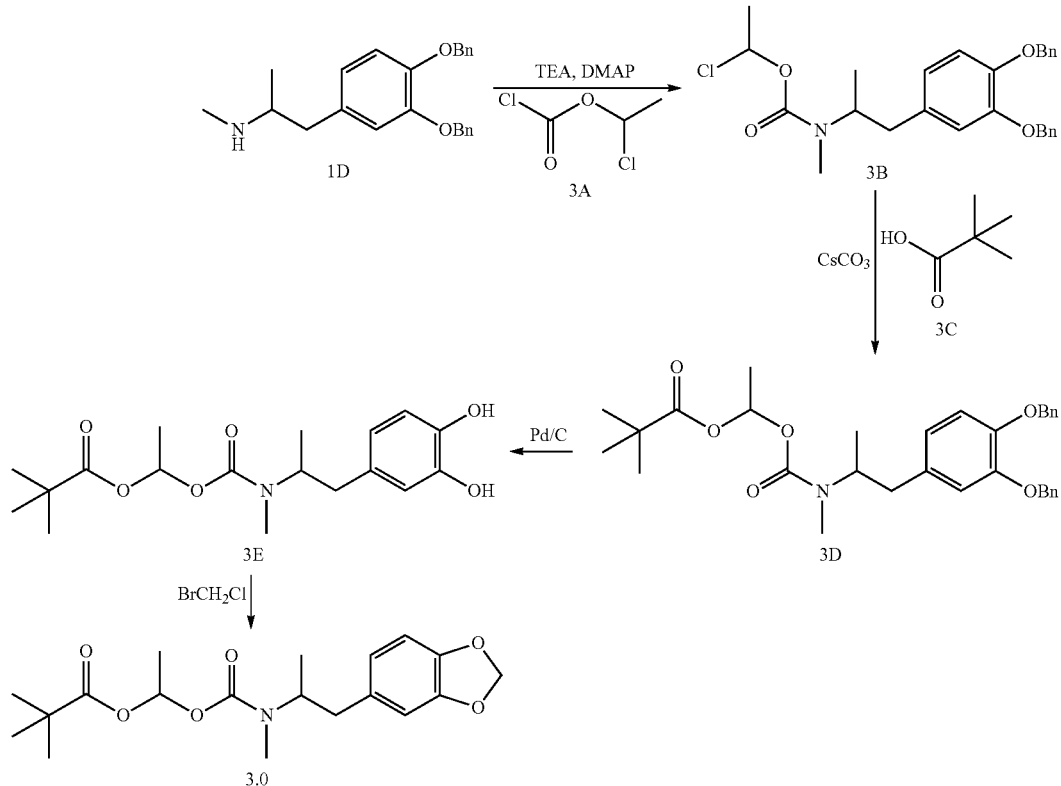

Scheme 3

Synthesis of 3B

To a solution of 1D (200.0 mg, 0.55 mmol, 1.0 equiv) and TEA (167.9 mg, 1.65 mmol, 3.0 equiv), DMAP (33.8 mg, 0.27 mmol, 0.5 equiv) in dichloromethane was added 1-chloroethyl carbonochloridate, 3A (237.3 mg, 1.65 mmol, 3.0 equiv) dropwise at 0° C. under nitrogen atmosphere. The resulting mixture was stirred for 16h at room temperature. The reaction was diluted with 50 mL of dichloromethane, washed with 2×20 mL saturated aqueous sodium chloride solution, dried over anhydrous sodium sulfate, filtered, and concentrated under reduced pressure. The crude (3B) was used in next step directly without further purification.

Synthesis of 3D

To a solution of 3B (150.0 mg, 0.32 mmol, 1.0 equiv) and pivalic acid, 3C (65.4 mg, 0.64 mmol, 2.0 equiv) in DMF was added cesium carbonate (125.32 mg, 0.385 mmol, 1.2 equiv), potassium iodide (10.6 mg, 0.06 mmol, 0.20 equiv) dropwise at room temperature under nitrogen atmosphere. The resulting mixture was stirred for 4h at 100° C. under nitrogen atmosphere. The reaction was diluted with 30 mL of dichloromethane, washed with 2×20 mL saturated aqueous sodium chloride solution, dried over anhydrous sodium sulfate, filtered, and concentrated under reduced pressure. The residue was purified by reversed-phase flash chromatography with the following conditions: column, C18 silica for 3 h at room temperature under hydrogen atmosphere. The solid was filtered and washed with tetrahydrofuran. The filtrate was concentrated under reduced pressure to provide 3E. The crude product (3E) was used in the next step directly without further purification.

Synthesis of 3.0

To a solution of 3E (90.0 mg, 0.25 mmol, 1.0 equiv) and cesium carbonate (132.7 mg, 0.41 mmol, 1.6 equiv) in DMF was added bromo(chloro)methane (52.7 mg, 0.41 mmol, 1.6 equiv) dropwise at 0° C. under nitrogen atmosphere. The resulting mixture was stirred for 2h at room temperature under nitrogen atmosphere. The reaction was diluted with 50 mL of dichloromethane, washed with 2×20 mL saturated aqueous sodium chloride solution, dried over anhydrous sodium sulfate, filtered, and concentrated under reduced pressure. The crude product was purified by Prep-HPLC with the following conditions (Column: XBridge Shield RP18 OBD Column, 30*150 mm, 5 μm; Mobile Phase A: Water (0.1% TFA), Mobile Phase B: ACN; Flow rate: 60 mL/min; Gradient: 50% B to 80% B in 9 min, 80% B; Wavelength: 254 nm) to afford Prodrug 3.0, 1-(((1-(benzo[d][1,3]dioxol-5-yl)propan-2-yl)(methyl)carbamoyl)oxy)ethyl pivalate (18 mg, 18%) as a colorless oil. MS m/z [M+H]+(ESI): 366.05. 1H NMR (400 MHz, Methanol-d4) δ 6.70-6.32 (m, 4H), 5.94-5.88 (m, 2H), 4.43-4.31 (m, 1H), 2.79-2.66 (m, 5H), 1.48-1.40 (m, 2H), 1.33-1.22 (m, 1H), 1.19-1.13 (m, 12H).

Synthesis of Prodrug 4.0: 2-amino-N-(1-(benzo[d][1,3]dioxol-5-yl)propan-2-yl)-N-methylacetamide Compound 4.0 was synthesized from commercially available compound NBoc protected glycine and previously synthesized intermediate 1D (Scheme 1) in four steps (Scheme 4).

Scheme 4

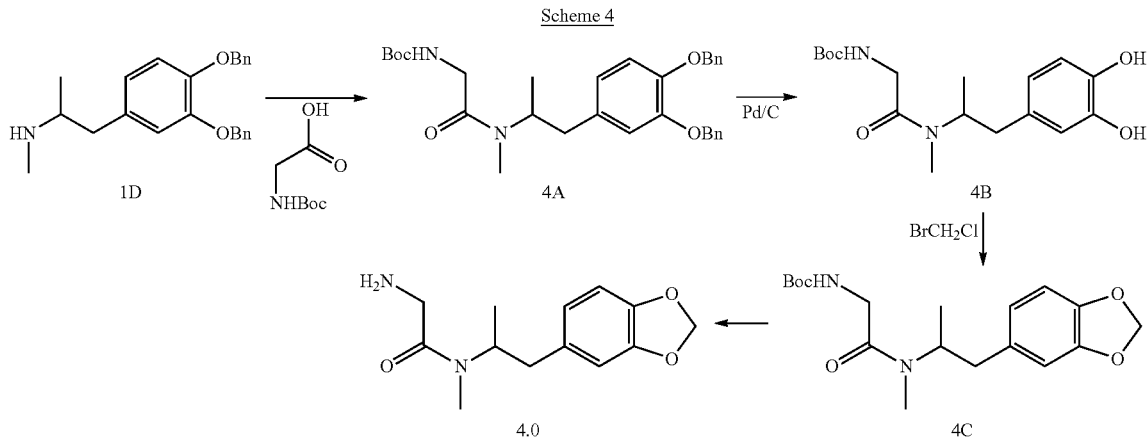

Synthesis of 4A

To a stirred solution of 1A (500.0 mg, 1.38 mmol, 1.0 equiv) and HATU (1.1 g, 2.77 mmol, 2.0 equiv) in DMF (5.0 mL) was added [(tert-butoxycarbonyl)amino]acetic acid (290.8 mg, 1.66 mmol, 1.2 equiv) and DIEA (536.3 mg, 4.15 mmol, 3.0 equiv) at room temperature under nitrogen atmosphere. The resulting mixture was stirred for 16h at room temperature. The reaction was diluted with 50 mL of dichloromethane, washed with 2×20 mL saturated aqueous sodium chloride solution, dried over anhydrous sodium sulfate, filtered, and concentrated under reduced pressure. The residue was purified by reversed-phase flash chromatography with the following conditions: column, C18 silica gel; mobile phase, acetonitrile in Water (0.05% $NH_4HCO_3$), 10% to 100% gradient in 20 min; detector, UV 254 nm. 450 mg of 4A was obtained as a colorless oil. MS m/z [M+H]+ (ESI): 519.28.

Synthesis of 4B

A mixture of 4A (450.0 mg, 0.87 mmol, 1.0 equiv) and 10% Pd/C (90.0 mg) in Tetrahydrofuran (5.0 mL) was stirred for 3 h at room temperature under hydrogen atmosphere. The solids were filtered and washed with Tetrahydrofuran. The filtrate was concentrated under reduced pressure and crude product 4B was obtained. The crude product 4B was used in the next step directly without further purification.

Synthesis of 4C

To a stirred mixture of 4B (250.0 mg, 0.74 mmol, 1.0 equiv) and cesium carbonate (433.3 mg, 1.33 mmol, 1.8 equiv) in DMF (3.0 mL) was added bromo(chloro)methane (172.1 mg, 1.33 mmol, 1.8 equiv) dropwise at 0° C. under nitrogen atmosphere. The resulting mixture was stirred for 2h at room temperature. The reaction was diluted with 30 mL of dichloromethane, washed with 2×20 mL saturated aqueous sodium chloride solution, dried over anhydrous sodium sulfate, filtered, and concentrated under reduced pressure. The residue was purified by reversed-phase flash chromatography with the following conditions: column, C18 silica gel; mobile phase, acetonitrile in Water (0.05% $NH_4HCO_3$), 10% to 100% gradient in 20 min; detector, UV 254 nm. 200 mg of 4C was obtained as a colorless oil. MS m/z [M+H]+(ESI): 351.18.

Synthesis of product, Prodrug 4.0

To a stirred solution of 4C (100.0 mg, 0.29 mmol, 1.0 equiv) in dichloromethane (1.0 mL) was added TFA (0.2 mL, 2.69 mmol) dropwise at room temperature. The resulting mixture was stirred for 1 h at room temperature. The resulting mixture was concentrated under reduced pressure. The residue was purified by reversed-phase flash chromatography with the following conditions: column, C18 silica gel; mobile phase, acetonitrile in Water (0.1% TFA), 10% to 100% gradient in 20 min; detector, UV 254 nm. 35.4 mg of 4.0, 2-amino-N-(1-(benzo[d][1,3]dioxol-5-yl)propan-2-yl)-N-methylacetamide, was obtained as a yellow oil (TFA Salt). MS m/z [M+H]+ (ESI): 251.10. $^1$H NMR (300 MHz, Methanol-d4) δ 6.77-6.65 (m, 3H), 5.90 (d, J=8.7 Hz, 2H), 4.87-4.76 (m, 1H), 3.92-3.70 (m, 2H), 3.06-2.84 (m, 3H), 2.80-2.70 (m, 2H), 1.32-1.16 (m, 3H).

Synthesis of Prodrug 5.0: 2-amino-N-(1-(benzo[d][1,3]dioxol-5-yl)propan-2-yl)acetamide Prodrug 5.0 was synthesized from the previous intermediate 2A in 4 steps (Scheme 5).

Scheme 5

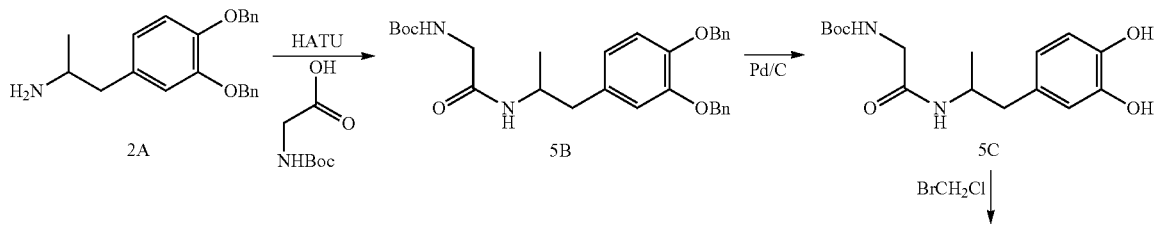

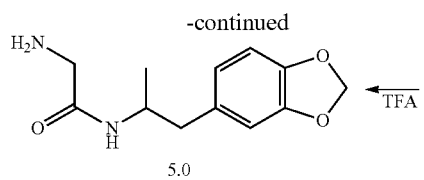 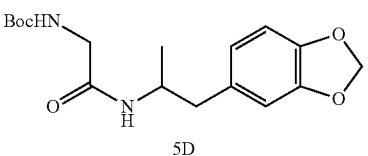

5.0 ←TFA— 5D

Synthesis of 5B

To a solution of 2A (500.0 mg, 1.44 mmol, 1.0 equiv) and [(tert-butoxycarbonyl)amino]acetic acid (378.1 mg, 2.16 mmol, 1.5 equiv), DIEA (557.9 mg, 4.32 mmol, 3.0 equiv) in DMF (5 mL) was added HATU (1367.9 mg, 3.59 mmol, 2.5 equiv) at 25° C. under nitrogen atmosphere. The resulting mixture was stirred for 16h at room temperature under nitrogen atmosphere. The reaction was diluted with 50 mL of dichloromethane, washed with 2×20 mL saturated aqueous sodium chloride solution, dried over anhydrous sodium sulfate, filtered and concentrated under reduced pressure. The residue was purified by reversed-phase flash chromatography with the following conditions: column, C18 silica gel; mobile phase, acetonitrile in water (0.1% FA), 10% to 100% gradient in 30 min; detector, UV 254 nm. This resulted in 5B (582 mg, 80%) as a white solid. MS m/z [M+H]$^+$ (ESI): 505.26.

Synthesis of 5C

A mixture of 5B (500.0 mg, 0.99 mmol, 1.0 equiv) and 10% Pd/C (100.0 mg) in tetrahydrofuran (10.0 mL) was stirred for 3 h at room temperature under hydrogen atmosphere. The solid was filtered and washed with tetrahydrofuran. The filtrate was concentrated under reduced pressure. The crude product (5C) was used in the next step directly without further purification.

Synthesis of 5D

To a mixture of 5C (500.0 mg, 1.54 mmol, 1.0 equiv) and cesium carbonate (803.5 mg, 2.46 mmol, 1.6 equiv) in DMF (5 mL) was added bromo(chloro)methane (319.1 mg, 2.46 mmol, 1.6 equiv) dropwise at 0° C. under nitrogen atmosphere. The resulting mixture was stirred for 2h at room temperature. The reaction was diluted with 50 mL of dichloromethane, washed with 2×30 mL saturated aqueous sodium chloride solution, dried over anhydrous sodium sulfate, filtered, and concentrated under reduced pressure. The residue was purified by reversed-phase flash chromatography with the following conditions: column, C18 silica gel; mobile phase, acetonitrile in water (0.1% FA), 10% to 100% gradient in 20 min; detector, UV 254 nm. This resulted in 5D (400.0 mg, 77%) as a white solid. MS m/z [M+H]$^+$ (ESI): 337.17.

Synthesis of 5.0

To a solution of 5D (70.0 mg, 0.21 mmol, 1.0 equiv) in dichloromethane (1 mL) was added TFA (0.2 mL) dropwise at room temperature under nitrogen atmosphere. The resulting mixture was stirred for 2h at room temperature under nitrogen atmosphere. The resulting mixture was concentrated under reduced pressure. The crude product was purified by Prep-HPLC with the following conditions (Column: XBridge Prep OBD C18 Column, 30*150 mm, 5 μm; Mobile Phase A: Water (0.1% TFA), Mobile Phase B: ACN; Flow rate: 60 mL/min; Gradient: 5% B to 28% B in 9 min, 28% B; Wavelength: 254 nm) to afford Prodrug 5.0, 2-amino-N-(1-(benzo[d][1,3]dioxol-5-yl)propan-2-yl)acetamide, (42 mg, 82%) as a white solid (TFA Salt). MS m/z [M+H]$^+$ (ESI): 237.10. $^1$H NMR (300 MHz, Methanol-d4) δ 6.73-6.64 (m, 3H), 5.89 (s, 2H), 4.17-4.05 (m, 1H), 3.64-3.51 (m, 2H), 2.76-2.61 (m, 2H), 1.13 (d, J=6.6 Hz 3H).

Synthesis of Prodrug 6.0: tert-butyl (R)-(1-(benzo[d][1,3]dioxol-5-yl)propan-2-yl)carbamate. Synthesis of Prodrug 7.0: tert-butyl (R)-(1-(benzo[d][1,3]dioxol-5-yl)propan-2-yl)(methyl)carbamate Prodrugs 6.0 and 7.0 were synthesized from the previously described chemistry from commercially available intermediate 6A and 6C in a few steps (Scheme 6).

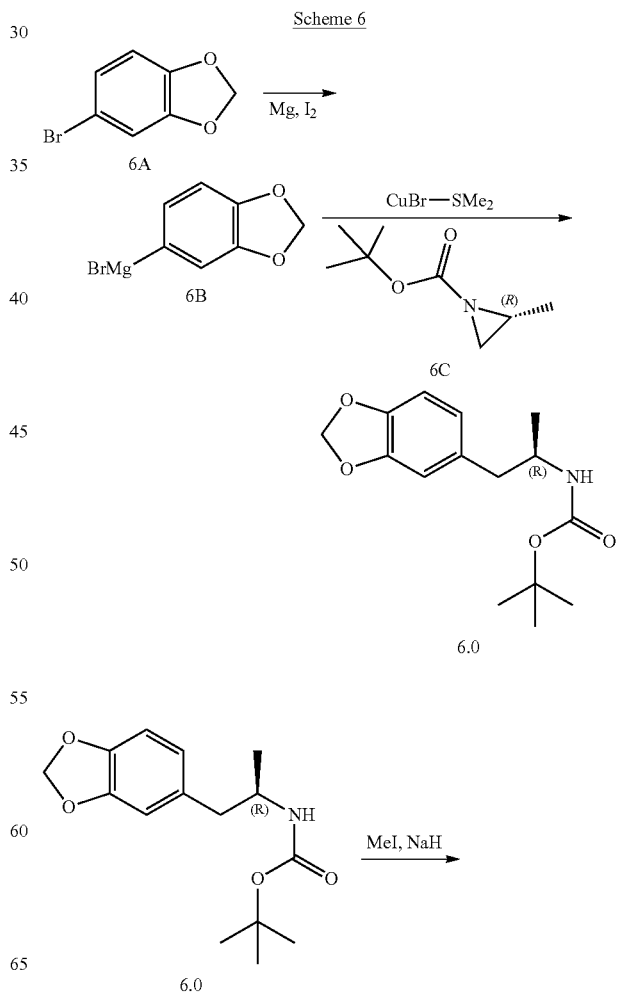

Scheme 6

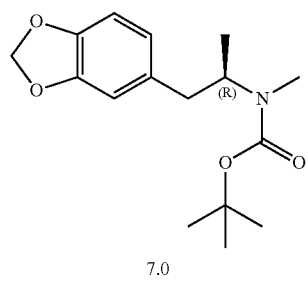

7.0

Synthesis of 6B

To a 100 mL flask was charged magnesium (60.4 mg, 2.487 mmol, 2.00 equiv.), iodine (one crystal) and tetrahydrofuran (1.5 mL) at room temperature under nitrogen. 5-Bromo-2H-1,3-benzodioxole (50 mg) was added to the mixture and heated to 50° C. at which time the iodine color disappeared, and the internal temperature rose to 56° C. 5-Bromo-2H-1,3-benzodioxole (450 mg, total added 500 mg, 2.487 mmol, 2.0 equiv.) was added, via syringe, to the mixture dropwise maintaining an internal temperature of 45-55° over 10 minutes. After addition was complete the syringe was rinsed with THF (0.1 mL) and the rinse charged to the reaction at 49° C. After stirring for 1.5 hours the batch was a clear amber color with an internal temperature of 19.6° C. THF (1 mL) was added. This crude material 6B was used directly for the next steps.

2. Synthesis of 6.0

The flask was cooled to 0.8° C. using an ice/water bath then solid CuBr·SMe2 (52.3 mg, 0.254 mmol, 0.2 equiv) was charged in one portion. An exotherm to 6° C. was observed. After cooling to 0.5° C. a solution of tert-butyl (2R)-2-methylaziridine-1-carboxylate (200 mg, 1.272 mmol, 1.0 equiv.) in tetrahydrofuran (0.5 mL) was added over 20 minutes, while maintaining an internal temperature<6° C. After stirring for 4 hours TLC analysis (5:1 heptane/EA) of the brown slurry showed complete reaction. After a further 20 minutes the reaction was quenched with dropwise addition sat. ammonium chloride (5.0 mL), while maintaining an internal temperature<18° C. (3 minutes).

After stirring for 12 minutes at room temperature the biphasic mixture was diluted with Ethyl acetate (1.5 mL). The layers were separated, and the aqueous layer was extracted with Ethyl acetate (2×1.5 mL). The combined organic layers dried over sodium sulfate (1.3 g), filtered, and concentrated under reduced pressure. Chromatographic purification in silica, eluting with 0-15% Ethyl acetate/heptane afforded 6.0, tert-butyl (R)-(1-(benzo[d][1,3]dioxol-5-yl)propan-2-yl)carbamate, (130 mg, 36% yield) as a white solid. 50 mg purified by reversed Flash with the following conditions: Column: XBridge Prep OBD C18 Column, 30*150 mm, 5 μm; Mobile Phase A: 10 mmol $NH_4HCO_{3+0.05}$% $NH_3H_2O$, Mobile Phase B: ACN; Flow rate: 60 mL/min; Gradient: 23% B to 53% B in 8 min, 53% B; Wavelength: 254 nm. The fractions of desired product were lyophilized. This resulted in 28.0 mg as a white solid. MS m/z [M−H]⁻ (ESI):278.15. $^1$H NMR (400 MHz, DMSO-$d_6$) δ 6.81-6.61 (m, 4H), 5.95-5.94 (m, 2H), 3.61-3.53 (m, 1H), 2.63-2.58 (m, 1H), 2.49-2.44 (m, 1H), 1.34 (s, 9H), 0.98 (d, J=6.8 Hz, 3H).

Synthesis of Prodrug 7.0

A solution of prodrug 6.0 (100 mg, 0.358 mmol, 1 equiv) in DMF (2 mL) was treated with sodium hydride (12.89 mg, 0.537 mmol, 1.5 equiv) for 30 min at 0° C. under nitrogen atmosphere followed by the addition of methyl iodide (101.63 mg, 0.716 mmol, 2 equiv) dropwise at 0° C. The resulting mixture was stirred for 16 hours at room temperature. The crude product was purified by Prep-HPLC with the following conditions (Column: Xselect CSH C18 OBD Column 30*150 mm 5 μm, n; Mobile Phase A: Water (0.1% FA), Mobile Phase B: ACN; Flow rate: 60 mL/min; Gradient: 25% B to 55% B in 8 min, 55% B; Wavelength: 254 nm) to afford 7.0, tert-butyl (R)-(1-(benzo[d][1,3]dioxol-5-yl)propan-2-yl)(methyl)carbamate, (34.5 mg, 32% yield) as a light-yellow oil. MS m/z [M+H]⁺ (ESI): 294.05. $^1$H NMR (300 MHz, DMSO-$d_6$) δ 6.81-6.59 (m, 3H), 5.93 (s, 2H), 4.33-4.10 (m, 1H), 2.61-2.55 (m, 5H), 1.30-1.08 (m, 12H). ee purity: 99.29%, $[\alpha]_D^{28.6}$=−118° (c=1 mg/mL, ACN)

Synthesis of Prodrug 8.0: (R)-4-(((1-(benzo[d][1,3]dioxol-5-yl)propan-2-yl)amino)methyl)-5-methyl-1,3-dioxol-2-one Scheme 7

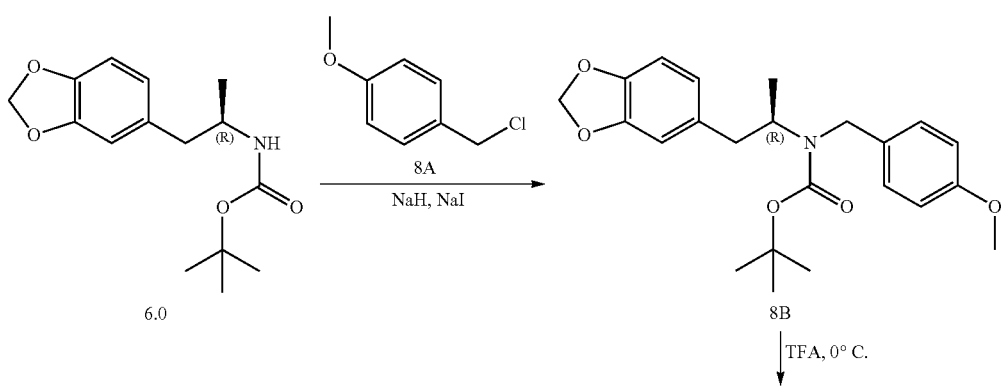

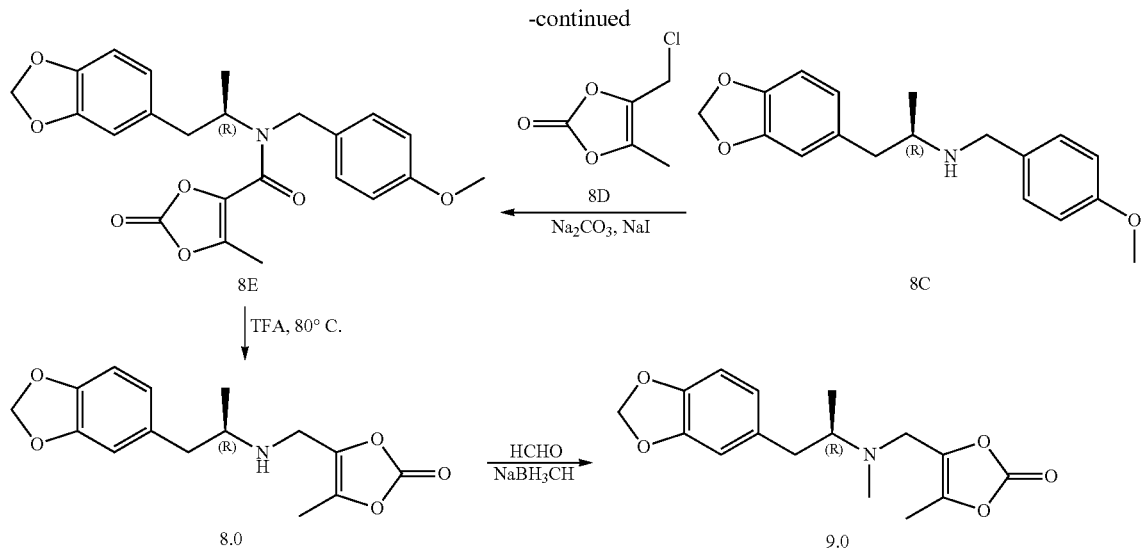

Synthesis of 8B

To a solution of 6.0 (4 g, 14.320 mmol, 1 equiv) in DMF (40 mL) was added sodium hydride (60% in oil, 859.1 mg, 1.5 equiv) at 0° C. The mixture was stirred for 15 minutes. 4-methoxybenzyl chloride 8A (4.49 g, 28.640 mmol, 2 equiv) was added by dropwise and the mixture was allowed to warm to room temperature and stirred for 2 hours. The reaction mixture was quenched by saturated ammonium chloride aqueous solution and extracted with dichloromethane (2×200 mL). The combined organic phase was dried over anhydrous sodium sulfate and concentrated under reduced pressure. The residue was purified by silica gel column chromatography, eluted with petroleum ether/ethyl acetate (9:1) to afford 8B (4.2 g, 73% yield) as a yellow oil. MS m/z [M+Na]$^+$ (ESI):422.15.

Synthesis 8C

To a stirred solution of 8B (4.2 g, 10.513 mmol, 1 equiv) in dichloromethane (56 mL) was added trifluoroacetic acid (28 mL) by dropwise at 0° C. The resulting mixture was stirred for 10 minutes at 0° C. The value of pH was adjusted to ~8 with saturated sodium bicarbonate aqueous solution at 0° C. The resulting mixture was extracted with ethyl acetate (2×200 mL). The combined organic layers were dried over anhydrous sodium sulfate and concentrated under reduced pressure. The residue was purified by silica gel column chromatography, eluted with dichloromethane/methanol (20:1) to afford 8C (2 g, 63% yield) as a yellow oil. MS m/z [M+H]+(ESI):300.20.

Synthesis 8E

To a solution of 8C (300 mg, 1.002 mmol, 1 equiv) in DMF (3 mL), Na$_2$CO$_3$ (214.4 mg, 2.004 mmol, 2 equiv), sodium iodide (30.0 mg, 0.200 mmol, 0.2 equiv) and 4-(chloromethyl)-5-methyl-1,3-dioxol-2-one 8D (297.7 mg, 2.004 mmol, 2 equiv) was added. The mixture was stirred for 4 hours. Then, the solid was filtered. The filtrate was purified by reversed-phase flash chromatography with the following conditions: column, C18 silica gel; mobile phase, acetonitrile in water (0.05% ammonium bicarbonate), 20% to 100% gradient in 15 min; detector, UV 220 nm. The fractions of desired product were concentrated under reduced pressure. This resulted in 8E (300 mg, 73% yield) as a yellow oil. MS m/z [M+H]+(ESI):412.20.

Synthesis of 8.0: (R)-4-(((1-(benzo[d][1,3]dioxol-5-yl)propan-2-yl)amino)methyl)-5-methyl-1,3-dioxol-2-one A solution of 8E (300 mg, 0.729 mmol, 1 equiv) in TFA (3 mL) was stirred for 2 days at 80° C. Then, it was cooled to room temperature and concentrated under reduced pressure. The residue was purified by reversed-phase flash chromatography with the following conditions: column, C18 silica gel; mobile phase, acetonitrile in water (0.05% TFA), 10% to 50% gradient in 15 min; detector, UV 220 nm. The fractions of desired product were concentrated under reduced pressure. This resulted in crude product. It was purified by Column: XSelect CSH Prep C18 OBD Column, 19*250 mm, 5 μm; Mobile Phase A: Water (0.1% FA), Mobile Phase B: ACN; Flow rate: 20 mL/min; Gradient: 13% B to 23% B in 8 min, 23% B; Wavelength: 254 nm. The fractions of desired product were lyophilized. This resulted in 8.0, (R)-4-(((1-(benzo[d][1,3]dioxol-5-yl)propan-2-yl)amino)methyl)-5-methyl-1,3-dioxol-2-one, (15.7 mg) as a grey semi-solid (FA salt). MS m/z [M+H]$^+$ (ESI):292.05. $^1$H NMR (300 MHz, Methanol-d$_4$) δ 6.82-6.71 (m, 3H), 5.94 (s, 2H), 4.21 (s, 2H), 3.58-3.49 (m, 1H), 3.15-3.09 (m, 1H), 2.70-2.63 (m, 1H), 2.20 (s, 3H), 1.27 (d, J=6.6 Hz, 3H). ee purity: 100%, $[\alpha]_D^{28.6}$=−168° (c=1 mg/mL, ACN)

Synthesis of Prodrug 9.0: (R)-4-(((1-(benzo[d][1,3]dioxol-5-yl)propan-2-yl)(methyl)amino)methyl)-5-methyl-1,3-dioxol-2-one To a solution of 8.0 (290 mg, 0.996 mmol, 1 equiv) in methanol (4.35 mL), sodium cyanoborohydride (125.12 mg, 1.992 mmol, 2 equiv) and formaldehyde (161.58 mg, 1.992 mmol, 2 equiv, 37% in water) was added at 0° C. It was stirred for 2 hours at room temperature. Then, it was quenched with saturated ammonium chloride aqueous solution. The resulting mixture was extracted with ethyl acetate (3×10 mL). The combined organic layers were washed with water and brine, dried over anhydrous sodium sulfate. After filtration, the filtrate was concentrated under reduced pressure. It was purified by Column: Xselect CSH C18 OBD Column 30*150 mm 5 μm, n; Mobile Phase A: Water (0.1% FA), Mobile Phase B: ACN; Flow rate: 60 mL/min; Gradient: 10% B to 40% B in 8 min, 40% B; Wavelength: 254 nm. The fractions of desired product were lyophilized. This resulted in 9.0, (R)-4-(((1-(benzo[d][1,3]dioxol-5-yl)propan-2-yl)(methyl)amino)methyl)-5-methyl-1,3-dioxol-2-one, (44.8 mg) as a light grey oil (FA salt). MS m/z [M+H]+ (ESI):306.10. $^1$H NMR (400 MHz, Acetonitrile-d$_3$) δ 6.80-6.72 (m, 2H), 6.70-6.64 (m, 1H), 5.93 (s, 2H), 3.45-3.35 (m, 2H), 3.00-2.91 (m, 1H), 2.81-2.76 (m, 1H), 2.49-2.41 (m, 1H), 2.25 (s, 3H), 2.04 (s, 3H), 0.96 (d, J=6.4 Hz, 3H). ee purity: 100%, $[\alpha]_D^{28.6}$=-95° (c=1 mg/mL, ACN).

It will be appreciated that the prodrugs of the invention afford increased exposure and bioavailability relative to parent drug itself. Prodrugs generated across different sites of the MDMA/MDA scaffold have specific pharmacokinetic profiles and afford distinct advantages to fine tune exposure, duration of exposure and overall intensity of entactogenic effects. Underlying these advantages are increased metabolic stability, increased absorption and decreased maximal plasma concentrations of parent drug over time. Prodrugs of the invention which limit maximal plasma concentrations of parent drug over time also limit amphetaminergic-like side effects of MDMA including hypertension. Limiting these side effects expands the suitability of MDMA for its intended PTSD population, of which many are obese and diagnosed with chronic hypertension.

Synthesis of Prodrug 11: phenyl N-(1-(benzo[d][1,3]dioxol-5-yl)propan-2-yl)-P-(methoxymethyl)-N-methylphosphonamidate Prodrug 11 was synthesis in 6 steps from commercially available intermediate (10A). and described in Scheme 8.

concentrated under reduced pressure. The crude was dissolved in dichloromethane (4 mL), one drop of N,N-Dimethylformamide and oxalyl chloride (418.06 mg, 3.294 mmol, 3 equiv) was added at 0° C. under nitrogen atmosphere. It was stirred for 1 hour at room temperature. Then, the solvent was removed under reduced pressure. This resulted in 11B (175 mg, 97% yield) as a yellow oil. The crude was used at next step directly.

Synthesis of Intermediate 11C:

To a solution of 11B (175 mg, 1.074 mmol, 1.2 equiv) in dichloromethane (2 mL), a solution phenol (84.24 mg, 0.895 mmol, 1 equiv) and triethylamine (271.72 mg, 2.685 mmol, 3 equiv) in dichloromethane (2 mL) was added by dropwise at -10° C. under nitrogen atmosphere. The mixture was stirred for 1 hour at room temperature. Then, a solution of 1D (258.84 mg, 0.716 mmol, 0.8 equiv) in dichloromethane (2 mL) was added into the system. It was stirred for 1 hour at room temperature. The reaction was diluted with DCM, washed with saturated sodium phosphate monobasic. The organic phase was dried over anhydrous sodium sulfate and concentrated under reduced pressure. The residue was purified by reversed-phase flash chromatography with the following conditions: column, C18 silica gel; mobile phase, acetonitrile in water (0.05% TFA), 20% to 100% gradient in 15 min; detector, UV 220 nm. This resulted in 11C (200 mg, 31% yield) as a colorless oil. MS m/z [M+H]+ (ESI): 546.35. This product (11C) was used directly for the next step without further characterization.

Synthesis of Intermediate 11D:

To a solution of 11C (200 mg, 0.275 mmol, 1 equiv, 75%) in tetrahydrofuran (4 mL) was added Pd/C (10%, 100 mg)

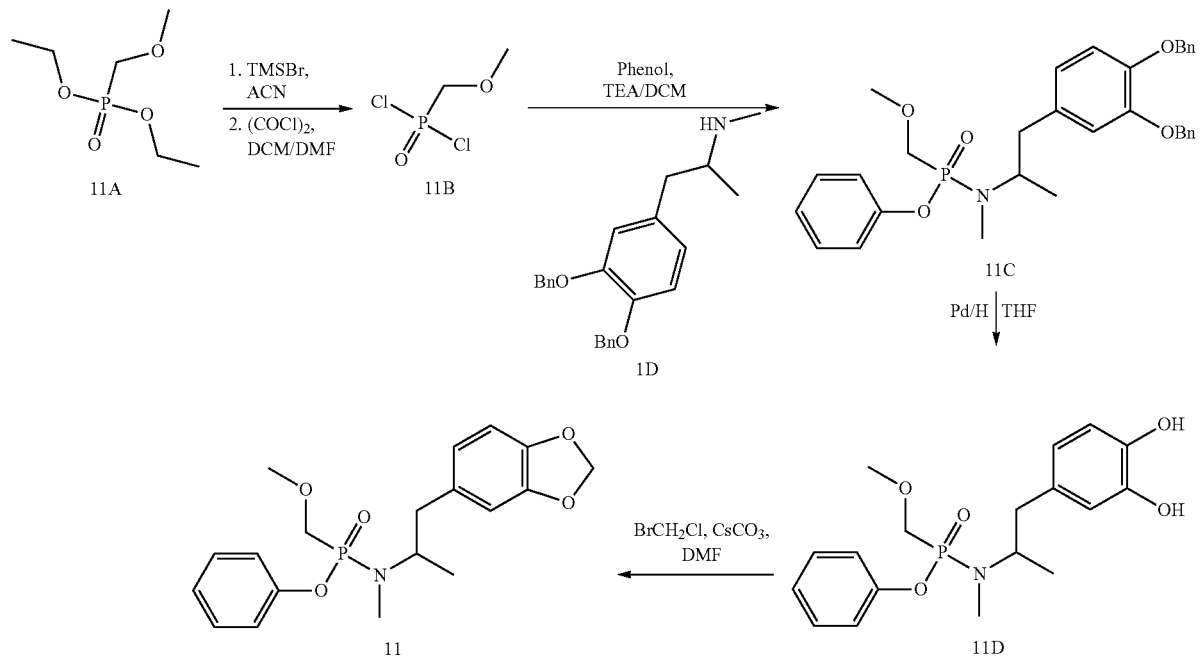

Scheme 8

Synthesis of Intermediate 11B:

To a solution of 11A (200 mg, 1.098 mmol, 1 equiv) in acetonitrile (2 mL), bromo-trimethylsilane (504.27 mg, 3.294 mmol, 3 equiv) was added. It was stirred for 2 hours at 50° C. Then, it was cooled to room temperature and under nitrogen atmosphere. The mixture was hydrogenated at room temperature for 3 hours under hydrogen atmosphere using a hydrogen balloon, filtered through a celite pad and concentrated under reduced pressure. The crude (11D: MS m/z [M+H]+ (ESI):366.20) was used at next step directly.

Synthesis of final Prodrug 11: Phenyl N-(1-(benzo[d][1,3]dioxol-5-yl)propan-2-yl)-P-(methoxymethyl)-N-methylphosphonamidate To a mixture of 11D (150 mg, 0.287 mmol, 1 equiv, 70%) in DMF (1.5 mL) was added bromochloromethane (59.49 mg, 0.459 mmol, 1.6 equiv) dropwise at room temperature under nitrogen atmosphere. It was stirred for 2 hours at room temperature. Then, the resulting mixture was filtered. The filtrate was purified by Column: XBridge Shield RP18 OBD Column 19*250 mm, 5 μm; Mobile Phase A: Water (0.1% FA), Mobile Phase B: ACN; Flow rate: 20 mL/min; Gradient: 0% B to 25% B in 10 min; Wavelength: 254 nm nm; RT1 (min): 9.0. The fractions of desired product were lyophilized. This resulted in prodrug 11, phenyl N-(1-(benzo[d][1,3]dioxol-5-yl)propan-2-yl)-P-(methoxymethyl)-N-methylphosphonamidate (33.1 mg, 30% yield) as a yellow oil. MS m/z [M+H]$^+$ (ESI): 378.10. $^1$H NMR (400 MHz, DMSO-$d_6$) δ 7.40-7.24 (m, 2H), 7.20-6.99 (m, 3H), 6.85-6.69 (m, 2H), 6.67-6.56 (m, 1H), 5.98-5.92 (m, 2H), 4.03-3.63 (m, 2H), 3.37-3.35 (m, 2H), 3.32-3.26 (m, 1H), 3.25-3.22 (m, 2H), 2.60-2.51 (m, 4H), 0.99-0.84 (m, 3H). $^{31}$P NMR (400 MHz, DMSO-$d_6$) δ 24.51, 24.23.

Example 2: Evaluation of Compound Stability

TABLE 2

Compound Chemical stability PBS (pH 6.5)

| ID | % Remaining at 0, 30, 60, 120 and 240 minutes | Prodrug-class |
|---|---|---|
| 1 | 100.00, 90.48, 90.36, 89.59, 90.28 | carbamate |
| 2 | 100.00, 89.05, 87.87, 91.21, 88.66 | carbamate |
| 3 | 100.00, 103.45, 107.91, 105.56, 96.60 | N-acyloxy alkoxy carbonyl |
| 4 | 100.00, 88.84, 92.54, 92.04, 92.48 | Amide/amino Acids |
| 5 | 100.00, 95.53, 97.09, 98.67, 105.87 | Amide/amino Acids |
| 6 | 100.00, 84.81, 93.60, 103.65, 91.66 | carbamate |
| 7 | 100.00, 94.54, 105.49, 105.72, 102.75 | carbamate |
| 8 | 100, 96, 93, 75, 72 | Dialkyl-1,3-dioxol-2-one |
| 9 | 100, 83, 75, 55, 32 | Dialkyl-1,3-dioxol-2-one |

TABLE 3

Compound Chemical stability SGF with pepsin

| ID | % Remaining at 0, 30, 60, 120 and 240 minutes | Prodrug-class |
|---|---|---|
| 1 | 100.00, 101.86, 98.61, 103.31, 100.50 | carbamate |
| 2 | 100.00, 100.95, 97.74, 98.18, 99.08 | carbamate |
| 3 | 100.00, 106.44, 108.51, 103.98, 106.17 | N-acyloxy alkoxy carbonyl |
| 4 | 100.00, 108.06, 98.50, 106.18, 103.88 | Amide/amino Acids |
| 5 | 100.00, 99.68, 105.84, 94.42, 91.97 | Amide/amino Acids |
| 6 | 100.00, 85.17, 79.89, 56.87, 31.48 | carbamate |
| 7 | 100.00, 74.97, 63.49, 56.42, 28.25 | carbamate |
| 8 | 100, 103, 98, 96, 92 | Dialkyl-1,3-dioxol-2-one |
| 9 | 100, 97, 92, 87, 71 | Dialkyl-1,3-dioxol-2-one |

TABLE 4

Compound Chemical stability SGF without pepsin

| ID | % Remaining at 0, 30, 60, 120 and 240 minutes | Prodrug-class |
|---|---|---|
| 1 | 100.00, 103.81, 101.90, 103.81, 104.29 | carbamate |
| 2 | 100.00, 102.53, 101.64, 90.45, 99.40 | carbamate |
| 3 | 100.00, 97.82, 97.35, 93.65, 94.12 | N-acyloxy alkoxy carbonyl |
| 4 | 100.00, 94.49, 96.72, 96.67, 96.46 | Amide/amino acids |
| 5 | 100.00, 101.17, 91.48, 95.49, 100.41 | Amide/amino acids |
| 6 | 100.00, 87.96, 77.20, 57.49, 28.57 | carbamate |
| 7 | 100.00, 89.90, 73.62, 61.79, 30.52 | carbamate |
| 8 | 100, 97, 94, 90, 86 | Dialkyl-1,3-dioxol-2-one |
| 9 | 1000, 94, 89, 83, 72 | Dialkyl-1,3-dioxol-2-one |

TABLE 5

Compound Mouse Plasma stability

| ID | % Remaining at 0, 15, 30, 60, and 120 minutes | Prodrug-class |
|---|---|---|
| 1 | 100.00, 108.51, 87.67, 98.49, 89.31 | carbamate |
| 2 | 100.00, 101.77, 86.60, 89.02, 84.42 | carbamate |
| 3 | 100, 0.0, 0.0, 0.0, 0.0 | N-acyloxy alkoxy carbonyl |
| 4 | 100.00, 102.99, 83.50, 94.51, 87.42 | Amide/amino acids |
| 5 | 100.00, 103.33, 87.64, 90.78, 83.06 | Amide/amino acids |
| 6 | 100, 102, 106, 92, 95 | carbamate |
| 7 | 100, 101, 92, 83, 92 | carbamate |
| 8 | 100, 72, 54, 25, 6 | Dialkyl-1,3-dioxol-2-one |
| 9 | 100, 70, 22, 4 | Dialkyl-1,3-dioxol-2-one |

Example 3: Evaluation of Compound Solubility

TABLE 6

Compound Solubility

| ID | Structure | MW | Prodrug-class | FaSSIF Solubility (uM) |
|---|---|---|---|---|
| 1 |  | 265.31 | carbamate | 309.11 |

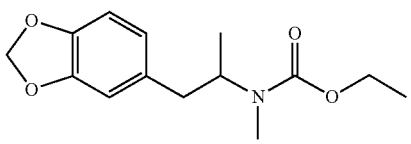 [SMILES: CCOC(=O)N(C)C(C)Cc1ccc2c(c1)OCO2]

TABLE 6-continued
Compound Solubility
| ID | Structure | MW | Prodrug-class | FaSSIF Solubility (uM) |
|---|---|---|---|---|
| 2 | 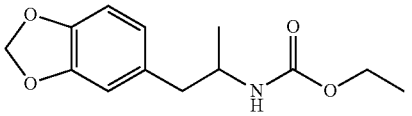 [SMILES: CCOC(=O)NC(C)Cc1ccc2c(c1)OCO2] | 251.28 | carbamate | 313.43 |
| 3 | 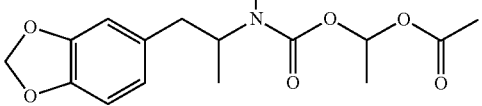 | 365.43 | N-acyloxy alkoxy carbonyl | 101.28 |
| 4 | 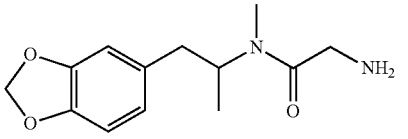 [SMILES: CC(Cc1ccc2c(c1)OCO2)N(C)C(=O)CN] | 250.3 | Amide/amino Acids | 291.11 |
| 5 | 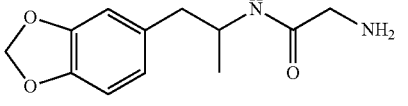 | 236.27 | Amide/amino Acids | 304.05 |
| 6 | 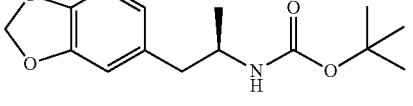 | 279.34 | carbamate | 175.28 |
| 7 | 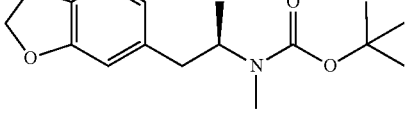 | 293.36 | carbamate | 256.53 |
| 8 | 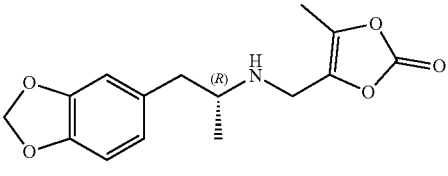 | 291.3 | Dialkyl-1,3-dioxol-2-one | 282.91 |
| 9 | 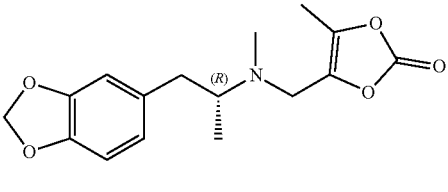 | 305.33 | Dialkyl-1,3-dioxol-2-one | 223.28 |
| 10 | 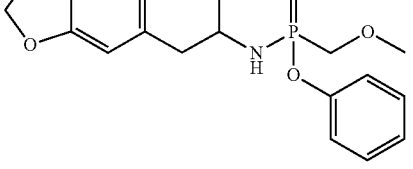 | 363.35 | Methoxymethyl phosphinyl | NA |

TABLE 6-continued

Compound Solubility

| ID | Structure | MW | Prodrug-class | FaSSIF Solubility (uM) |
|---|---|---|---|---|
| 11 | 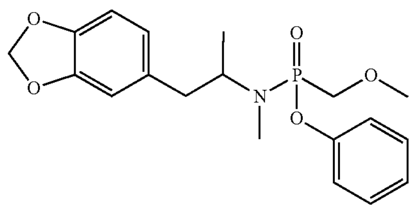 [SMILES: COCP(=O)(Oc1ccccc1)N(C)C(C)Cc1ccc2c(c1)OCO2] | 377.38 | Methoxymethyl phosphinyl | NA |

The invention claimed is:

1. A compound of Formula (IIIa):

(IIIa)

or a pharmaceutically acceptable salt thereof;
wherein,
$R_1$ is H or alkyl;
$R_2$ is H, halogen, alkyl, —OH, or —O-alkyl;
$R_3$ is H, alkyl, —OH, —O-alkyl, or —O-cycloalkyl;
$R_4$ and $R_7$ are each independently H, halogen, —OH, —O-alkyl, —O-cycloalkyl, alkylene-$OR_8$, —SH, —S-alkyl, —S-cycloalkyl, or alkylene-$SR_8$;
$R_8$ is H, alkyl, cycloalkyl, or alkylenecycloalkyl;
B is wherein $R_B$ is H or alkyl; and
$R_{11}$ and $R_{12}$ are each independently H, alkyl, cycloalkyl, or Ru and $R_{12}$ together with the atoms to which they are attached form a 5- to 8-membered heterocyclyl ring.

2. The compound of claim 1, wherein at least one of $R_4$ and $R_7$ is not H.

3. The compound of claim 1, wherein $R_1$ is H or $C_1$-$C_6$ alkyl.

4. The compound of claim 1, wherein $R_1$ is H.

5. The compound of claim 1, wherein $R_1$ is —$CH_3$.

6. The compound of claim 1, wherein $R_2$ is H, alkyl, or —OH.

7. The compound of claim 1, wherein $R_2$ is alkyl.

8. The compound of claim 6, wherein $R_2$ is methyl or isopropyl.

9. The compound of claim 1, wherein $R_3$ is H, —OH, or —O-alkyl.

10. The compound of claim 1, wherein $R_4$ is H.

11. The compound of claim 1, wherein $R_7$ is H.

12. The compound of claim 1, having the structure of Formula (IIIb):

(IIIb)

or a pharmaceutically acceptable salt thereof,
wherein n is 1 or 2.

13. The compound of claim 12, having the structure:

or a pharmaceutically acceptable salt thereof.

14. The compound of claim 13, having the structure:

or

15. The compound of claim 13, having the structure:

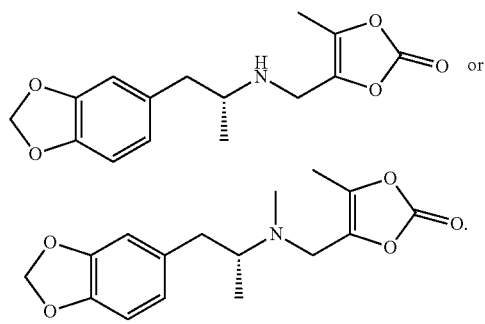

or

16. A pharmaceutical composition comprising a compound of claim 1 and a pharmaceutically acceptable excipient.

17. The pharmaceutical composition of claim 16, wherein the composition provides an in vivo plasma level characterized by a $C_{max}$ of free amine of about 100 ng/mL to about 500 ng/mL, after oral administration of from about 80 mg to about 125 mg of a compound of Formula (IIIa).

18. The pharmaceutical composition of claim 16, wherein the composition provides an in vivo plasma level characterized by an $AUC_{(0-24)}$ of free amine of about 1000 h*ng/mL to about 6000 h*ng/mL, after oral administration of from about 80 mg to about 125 mg of a compound of Formula (IIIa).

19. The pharmaceutical composition of claim 16, wherein the composition provides an in vivo $T_{1/2}$ of free amine of about 5 h to about 15 h, after oral administration of from about 80 mg to about 125 mg of a compound of Formula (IIIa).

20. A method of treating post-traumatic stress disorder (PTSD) in a subject in need thereof, comprising administering to the subject a therapeutically effective amount of a composition of claim 16.

21. A method of treating an eating disorder in a subject in need thereof, comprising administering to the subject a therapeutically effective amount of a composition of claim 16.

22. A method of treating depression in a subject in need thereof, comprising administering to the subject a therapeutically effective amount of a composition of claim 16.

23. The method of claim 22, wherein the depression is major depressive disorder (MDD) or treatment-resistant depression (TRD).

24. A method of treating an anxiety disorder in a subject in need thereof, comprising administering to the subject a therapeutically effective amount of a composition of claim 16.

25. The method of claim 24, wherein the anxiety disorder is generalized anxiety disorder.

* * * * *

UNITED STATES PATENT AND TRADEMARK OFFICE
CERTIFICATE OF CORRECTION

PATENT NO. : 11,845,736 B2
APPLICATION NO. : 17/959256
DATED : December 19, 2023
INVENTOR(S) : Srinivas Rao et al.

It is certified that error appears in the above-identified patent and that said Letters Patent is hereby corrected as shown below:

In the Claims

At Column 95, Claim number 1, Line number 53, shows:
--$R_u$ and $R_{12}$ together with the atoms to which...--
Should show:
--$R_{11}$ and $R_{12}$ together with the atoms to which...--

Signed and Sealed this
Fourteenth Day of May, 2024

Katherine Kelly Vidal
*Director of the United States Patent and Trademark Office*